(12) United States Patent
Yan et al.

(10) Patent No.: US 10,023,889 B2
(45) Date of Patent: Jul. 17, 2018

(54) MICROBIAL APPROACH FOR THE PRODUCTION OF 5-HYDROXYTRYPTOPHAN

(71) Applicant: UNIVERSITY OF GEORGIA RESEARCH FOUNDATION, INC., Athens, GA (US)

(72) Inventors: Yajun Yan, Bogart, GA (US); Yuheng Lin, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 15/310,040

(22) PCT Filed: May 14, 2015

(86) PCT No.: PCT/US2015/030811
§ 371 (c)(1),
(2) Date: Nov. 9, 2016

(87) PCT Pub. No.: WO2015/175793
PCT Pub. Date: Nov. 19, 2015

(65) Prior Publication Data
US 2017/0240939 A1 Aug. 24, 2017

Related U.S. Application Data

(60) Provisional application No. 61/994,413, filed on May 16, 2014.

(51) Int. Cl.
| | | |
|---|---|---|
| *C12N 1/20* | (2006.01) | |
| *C12P 13/22* | (2006.01) | |
| *C12N 9/02* | (2006.01) | |
| *C12N 9/88* | (2006.01) | |
| *C12N 9/06* | (2006.01) | |
| *A23L 2/52* | (2006.01) | |
| *A23K 20/10* | (2016.01) | |

(52) U.S. Cl.
CPC ............ *C12P 13/227* (2013.01); *A23K 20/10* (2016.05); *A23L 2/52* (2013.01); *C12N 9/0028* (2013.01); *C12N 9/0071* (2013.01); *C12N 9/88* (2013.01); *C12Y 105/01034* (2013.01); *C12Y 114/16001* (2013.01); *C12Y 402/01096* (2013.01)

(58) Field of Classification Search
CPC ..................... C12P 13/227; C12Y 114/16001
USPC ....................................................... 435/252.3
See application file for complete search history.

(56) References Cited

U.S. PATENT DOCUMENTS

| 5,756,345 A | 5/1998 | Camakaris et al. |
| 2009/0311760 A1 | 12/2009 | Wery et al. |
| 2014/0370557 A1 | 12/2014 | Yan et al. |

FOREIGN PATENT DOCUMENTS

| CN | 102453691 B | 5/2012 |
| WO | WO 2013/112873 A2 | 8/2013 |
| WO | WO 2013/127914 A1 | 9/2013 |
| WO | WO 2015/175793 A1 | 11/2015 |

OTHER PUBLICATIONS

Kino et al. [Journal of Bioscience and Bioengineering, vol. 108 No. 3, 184-189, 2009].*
Hara and Kino [AMB Express 2013, 3:70, pp. 1-7].*
International Patent Application No. PCT/US2015/030811, filed May 14, 2015; International Search Report and Written dated Aug. 26, 2015; 9 pages.
International Patent Application No. PCT/US2015/030811, filed May 14, 2015; International Preliminary Report on Patentability dated Dec. 1, 2016; 6 pages.
American Type Culture Collection, Product Sheet, "ATTC No. 31884," organism: *Escherichia coli* (Migula) Castellani and Chalmers; designation: NST 74 [online]; Manassas, VA [retrieved on Dec. 21, 2017] from the Internet. Retrieved from the Internet:<URL: https://www.atcc.org/Products/All/31884.aspx#documentation>; 2 pgs.
6,7-Dimethyl-5,6,7,8-tetrahydropterin . hydrochloride ALX-440-034. Product Data Sheet [online]. ENZO Life Sciences, Inc. Dec. 14, 2017; [retrieved on Jan. 26, 2018]. Retrieved from the Internet: <URL: www.enzolifesciences.com/fileadmin/reports/Datasheet-ALX-440-034.pdf>.
Ajikumar et al., "Isoprenoid Pathway Optimization for Taxol Precursor Overproduction in *Escherichia coli*" Science, Oct. 1, 2010; 330(6000):70-4.
Anthony et al., "Optimization of the mevalonate-based isoprenoid biosynthetic pathway in *Escherichia coli* for production of the anti-malarial drug precursor amorpha-4,11-diene" Metab Eng, Jan. 2009; 11(1):13-9. Epub Aug. 12, 2008.
Attele et al., "Treatment of insomnia: an alternative approach" Altern Med Rev, Jun. 2000; 5(3):249-59. VA [retrieved on Dec. 21, 2017] from the Internet. Retrieved from the Internet:<URL: http://www.altmedrev.com/publications/5/3/249.pdf > 11 pages.
Birdsall "5-Hydroxytryptophan: a clinically-effective serotonin precursor" Altern. Med. Rev. 1998; 3(4):271-80.
Byerley et al., "5-Hydroxytryptophan: a review of its antidepressant efficacy and adverse effects" J Clin Psychopharmacol, Jun. 1987; 7(3):127-37.
Cao et al., "Phylogenetic analysis and evolution of aromatic amino acid hydroxylase" FEBS Lett, Dec. 1, 2010; 584(23):4775-82. Epub Nov. 10, 2010.
Cangiano et al., "Effects of oral 5-hydroxy-tryptophan on energy intake and macronutrient selection in non-insulin dependent diabetic patients" Int J Obes Relat Metab Disord, Jul. 1998; 22(7):648-54.

(Continued)

Primary Examiner — Tekchand Saidha
(74) Attorney, Agent, or Firm — Mueting, Raasch & Gebhardt, P.A.

(57) ABSTRACT

5-hydroxytryptophan (5-HTP), a precursor of serotonin, is produced in a microbial host cell. A modified bacterial phenylalanine 4-hydroxylase (P4H) catalyzes the tryptophan 5-hydroxylation reaction. Optionally the host cell includes a cofactor regeneration mechanism, allowing continuous production of 5-HTP without supplementation of exogenous cofactors.

21 Claims, 15 Drawing Sheets

(56) References Cited

OTHER PUBLICATIONS

Caruso et al., "Double-blind study of 5-hydroxytryptophan versus placebo in the treatment of primary fibromyalgia syndrome" J Int Med Res, May-Jun. 1990;18(3):201-9.

Ceci et al., "The effects of oral 5-hydroxytryptophan administration on feeding behavior in obese adult female subjects" J Neural Transm, 1989; 76(2):109-17.

ChEBI, "ChEBI:71177—tetrahydromonapterin" Submitted by Eugeni Belda [retrieved on Jan. 31, 2018]. Retrieved from the Internet: <URL: <http://www.ebi.ac.uk/chebi/searchId.do?chebiId=CHEBI:71177>. Hastings et al., "The ChEBI reference database and ontology for biologically relevant chemistry: enhancements for 2013" Nucleic Acids Res, Jan. 1, 2013; 41(Database issue):D456-D63. Epub Nov. 24, 2012. 1 page.

Collier et al., "Serotonin as a homeostatic regulator of lactation" Domest Anim Endocrinol, Aug. 2012; 43(2):161-70. Epub Apr. 19, 2012.

Curcio et al., "The Potential Role of 5-Hydroxytryptophan for Hot Flash Reduction: A Hypothesis" Altern Med Rev. Sep. 2005; 10(3):216-21.

Datsenko et al., "One-step inactivation of chromosomal genes in Escherichia coli K-12 using PCR products" Proc Natl Acad Sci USA, Jun. 6, 2000; 97(12):6640-5.

Daubner et al., "Site-directed mutagenesis of serine 40 of rat tyrosine hydroxylase. Effects of dopamine and cAMP-dependent phosphorylation on enzyme activity" J Biol Chem, Jun. 25, 1992; 267(18):12639-46.

DeGaris et al. "Milk fever in dairy cows: a review of pathophysiology and control principles" Apr. 2008; Vet J, 176(1):58-69. Epub Mar. 7, 2008.

Ekstrom et al., "Crystallization and X-ray analysis of a bacterial non-haem iron-containing phenylalanine hydroxylase from the Gram-negative opportunistic pathogen Pseudomonas aeruginosa" Acta Crystallogr D Biol Crystallogr, Jul. 2003; 59(Pt 7):1310-2. Epub Jun. 27, 2003.

Erlandsen et al., "Structural comparison of bacterial and human iron-dependent phenylalanine hydroxylases: similar fold, different stability and reaction rates" J Mol Biol, Jul. 12, 2002; 320(3):645-61.

Fitzpatrick, "Mechanism of aromatic amino acid hydroxylation" Biochemistry, Dec. 9, 2003; 42(48):14083-91.

Freedman, "Treatment of menopausal hot flashes with 5-hydroxytryptophan" Maturitas, Apr. 2010; 65(4):383-5.

Goff et al., "Milk fever control in the United States" Acta Vet Scand Suppl, 2003; 97:145-7.

Gong et al., "The mechanism of tryptophan induction of tryptophanase operon expression: tryptophan inhibits release factor-mediated cleavage of TnaC-peptidyl-tRNA(Pro)" Proc Natl Acad Sci USA, Jul. 31, 2001; 98(16):8997-9001. Epub Jul. 24, 2001.

Hara et al., "Enhanced synthesis of 5-hydroxy-l-tryptophan through tetrahydropterin regeneration" AMB Express, 2013; 3(1):70. 7 pages. Epub Dec. 9, 2013.

Hastings et al., "The ChEBI reference database and ontology for biologically relevant chemistry: enhancements for 2013" Nucleic Acids Res, Jan. 1, 2013; 41(Database issue):D456-D63. Epub Nov. 24, 2012.

Hernandez et al., "The bovine mammary gland expresses multiple functional isoforms of serotonin receptors" J Endocrinol, Oct. 2009; 203(1):123-31. Epub Aug. 4, 2009.

Hernandez, L., "Calcium Homeostasis in Transition Dairy Cattle," Grant Abstract, Project No. WIS01618 [online]. National Institute of Food and Agriculture, project dates Sep. 1, 2011 to Aug. 31, 2013 [retrieved on Dec. 21, 2017]. Retrieved from the Internet:<URL: https://reeis.usda.gov/web/crisprojectpages/0227299-calcium-homeostasis-in-transition-dairy-cattle.html>; 4 pgs.

Higgins et al., "Expression and purification of recombinant human tyrosine hydroxylase as a fusion protein in Escherichia coli" Protein Expr Purif, Aug. 2012; 84(2):219-23. Epub Jun. 1, 2012.

Horseman et al., "Serotonin: a local regulator in the mammary gland epithelium" Annu Rev Anim Biosci, Feb. 2014; 2:353-74. Epub Nov. 14, 2013.

Huang et al., "Caffeic acid production enhancement by engineering a phenylalanine over-producing Escherichia coli strain" Biotechnol Bioeng, Dec. 2013; 110(12):3188-96. Epub Jul. 11, 2013.

Huang et al., "Production of tyrosine through phenylalanine hydroxylation bypasses the intrinsic feedback inhibition in Escherichia coli" J Ind Microbiol Biotechnol, Apr. 2015; 42(4):655-9. Epub Feb. 3, 2015.

Jury et al., "Enhanced responsiveness to selective serotonin reuptake inhibitors during lactation" PLoS One, Feb. 17, 2015; 10(2):e0117339. eCollection 2015.

Kino et al., "Enhancement of L-tryptophan 5-hydroxylation activity by structure-based modification of L-phenylalanine 4-hydroxylase from Chromobacterium violaceum" J Biosci Bioeng, Sep. 2009; 108(3):184-9.

Leonard et al., "Combining metabolic and protein engineering of a terpenoid biosynthetic pathway for overproduction and selectivity control" Proc Natl Acad Sci USA, Aug. 3, 2010; 107(31):13654-9.

Lim et al., "High-Yield Resveratrol Production in Engineered Escherichia coli" Appl Environ Microbiol, May 2011; 77(10):3451-60. Epub Mar. 25, 2011.

Lin et al., "Biosynthesis of caffeic acid in Escherichia coli using its endogenous hydroxylase complex" Microb Cell Fact, Apr. 4, 2012; 11:42.

Lin et al., "Microbial biosynthesis of the anticoagulant precursor 4-hydroxycoumarin" Nat Commun, 2013; 4:2603. Epub Oct. 16, 2013.

Lin et al., "Extending shikimate pathway for the production of muconic acid and its precursor salicylic acid in Escherichia coli" Metab Eng, May 2014; 23:62-9. Epub Feb. 25, 2014.

Lin et al., "Engineering Bacterial Phenylalanine 4-Hydroxylase for Microbial Synthesis of Human Neurotransmitter Precursor 5-Hydroxytryptophan" ACS Synth. Biol., Jul. 18, 2014; 3(7), pp. 497-505. Epub Jun. 30, 2014.

Marcheschi et al., "Protein engineering for metabolic engineering: current and next-generation tools" Biotechnol J, May 2013; 8(5):545-55. Epub Apr. 16, 2013.

Marshall et al., "Serotonin and serotonin transport in the regulation of lactation" J Mammary Gland Biol Neoplasia, Mar. 2014; 19(1):139-46. Epub Oct. 18, 2013.

Martinez et al., "A structural approach into human tryptophan hydroxylase and its implications for the regulation of serotonin biosynthesis" Curr Med Chem, Jul. 2001; 8(9):1077-91.

McKinney et al., "Expression and purification of human tryptophan hydroxylase from Escherichia coli and Pichia pastoris" Protein Expr Purif, Feb. 2004; 33(2):185-194.

Moneva et al., "Study on the Metabolic Implication of Supplemental Tryptophan in Exposed to Stress Chickens" Bulgarian J Ag Sci, 2008; 14(4):424-31.

Mora-Pale et al., "Biochemical strategies for enhancing the in vivo production of natural products with pharmaceutical potential" Curr Opin Biotechnol, Feb. 2014; 25:86-94. Epub Oct. 29, 2013.

Nakata et al., "Phenylalanine hydroxylase from Chromobacterium violaceum. Purification and characterization" J Biol Chem, Mar. 25, 1979; 254(6):1829-33.

Onishi et al., "Cloning and Expression of Chromobacterium violaceum Phenylalanine Hydroxylase in Escherichia coli and Comparison of Amino Acid Sequence with Mammalian Aromatic Amino Acid Hydrolases" J Biol Chem, Oct. 5, 1991; 266(28):18454-9.

Pai et al., "The type 7 serotonin receptor, 5-HT 7, is essential in the mammary gland for regulation of mammary epithelial structure and function" Biomed Res Int, 2015; 2015:364746. Epub Jan. 18, 2015.

Pribat et al., "FolX and FolM are essential for tetrahydromonapterin synthesis in Escherichia coli and Pseudomonas aeruginosa" J Bacteriol, Jan. 2010; 192(2):475-82.

Puttini et al., "Primary fibromyalgia syndrome and 5-hydroxy-L-tryptophan: a 90-day open study" J Int Med Res, Apr. 1992; 20(2):182-9.

Renson et al., "Hydroxylation of Tryptophan by Phenylalanine Hydroxylase" J Biol Chem, Jul. 7, 1962; 237(7):2261-4.

(56) References Cited

OTHER PUBLICATIONS

Ribeiro, "L-5-Hydroxytryptophan in the prophylaxis of chronic tension-type headache: a double-blind, randomized, placebo-controlled study. For the Portuguese Head Society" Jun. 2000; 40(6):451-6.

Ro et al., "Production of the antimalarial drug precursor artemisinic acid in engineered yeast" Nature, Apr. 13, 2006; 440(7086):940-3.

Satoh et al., "Engineering of L-tyrosine oxidation in *Escherichia coli* and microbial production of hydroxytyrosol" Metab Eng, Nov. 2012; 14(6):603-10. Epub Aug. 29, 2012.

Shen et al., "Inhibition of acetate accumulation leads to enhanced production of (R,R)-2,3-butanediol from glycerol in *Escherichia coli*" J Ind Microbiol Biotechnol, Nov. 2012; 39(11):1725-9. Epub Jul. 26, 2012.

Simat and Steinhart, "Oxidation of Free Tryptophan and Tryptophan Residues in Peptides and Proteins" J Agric Food Chem, Feb. 16, 1998; 46(2):490-8.

Song et al., "PhhB, a Pseudomonas aeruginosa homolog of mammalian pterin 4a-carbinolamine dehydratase/DCoH, does not regulate expression of phenylalanine hydroxylase at the transcriptional level" J Bacteriol, May 1999; 181(9):2789-96.

Tamura et al., "MEGA5: molecular evolutionary genetics analysis using maximum likelihood, evolutionary distance, and maximum parsimony methods" Mol Biol Evol, Oct. 2011; 28(10):2731-9. Epub May 4, 2011.

Teigen et al., "Selectivity and affinity determinants for ligand binding to the aromatic amino acid hydroxylases" Curr Med Chem, 2007; 14(4):455-67.

Thomas et al., "Circadian rhythm of tryptophan hydroxylase activity in chicken retina" Cell Mol Neurobiol, Oct. 1991; 11(5):511-27.

Turner et al., "Serotonin a la carte: supplementation with the serotonin precursor 5-hydroxytryptophan" Pharmacol. Ther, Mar. 2006; 109(3):325-38. Epub Jul. 14, 2005.

Wang et al., "Genetic engineering of *Escherichia coli* to enhance production of L-tryptophan" Appl Microbiol Biotechnol, Sep. 2013; 97(17):7587-96. Epub Jun. 18, 2013.

World Health Organization (WHO), Depression: Fact Sheet [online] Feb. 2017 [retrieved on Dec. 26, 2017]. Retrieved from the Internet: <URL: www.who.int/mediacentre/factsheets/fs369/en/>. 4 pages.

Zhang et al., "Expanding metabolism for total biosynthesis of the nonnatural amino acid L-homoalanine" Proc Natl Acad Sci USA, Apr. 6, 2010; 107(14):6234-9.

Zhao et al., "Pseudomonas aeruginosa possesses homologues of mammalian phenylalanine hydroxylase and 4 alpha-carbinolamine dehydratase/DCoH as part of a three-component gene cluster" Proc Natl Acad Sci USA, Feb. 15, 1994; 91(4):1366-70.

Zhao et al., "Development of L-tryptophan production strains by defined genetic modification in *Escherichia coli*" J Ind Microbiol Biotechnol, Dec. 2011; 38(12):1921-9. Epub May 4, 2011.

Zoidakis et al., "Role of the second coordination sphere residue tyrosine 179 in substrate affinity and catalytic activity of phenylalanine hydrolase" J Biol Inorg Chem, 2004; 9:289-96. Epub Mar. 4, 2004.

* cited by examiner (A)

*Pseudomonas aeruginosa* (PaP4H) Protein Sequence

MKTTQYVARQPDDNGFIHYPETEHQVWNTLITRQLKVIEGRAC
QEYLDGIEQLGLPHERIPQLDEINRVLQATTGWRVARVPALIP
FQTFFELLASQQFPVATFIRTPEELDYLQEPDIFHEIFGHCPL
LTNPWFAEFTHTYGKLGLKASKEERVFLARLYWMTIEFGLVET
DQGKRIYGGGILSSPKETVYSLSDEPLHQAFNPLEAMRTPYRI
DILQPLYFVLPDLKRLFQLAQEDIMALVHEAMRLGLHAPLFPP
KQAA*

(B)

*Pseudomonas fluorescens* (PfP4H) Protein Sequence

MKQTQYVAREPDAQGFIDYPPEEHAVWNTLITRQLKVIEGRAC
QEYLDGIDKLGLPHDRIPQLGEINKVLGETTGWQVARVPALIP
FQTFFELLASKRFPVATFIRTREELDYLQEPDIFHEIFGHCPL
LTNPWFAEFTHTYGKLGLQATKEERVYLARLYWMTIEFGLVDT
PAGRRIYGGGILSSPKETVYSLSEEPEHQAFDPLEAMRTPYRI
DILQPIYFTLPNLKRLFDLAHEDIMALVHQGMQLGLHAPKFPP
KPKAA*

Pseudomonas putida (PpP4H) Protein Sequence

MKQTQYVAREPDAHGFIDYPQQEHAVWNTLITRQLKVIEGRAC
QEYLDGIDQLKLPHDRIPQLGEINKVLGATTGWQVARVPALIP
FQTFFELLASKRFPVATFIRTPEELDYLQEPDIFHEIFGHCPL
LTNPWFAEFTHTYGKLGLAATKEQRVYLARLYWMTIEFGLMET
AQGRKIYGGGILSSPKETVYSLSDEPEHQAFDPIEAMRTPYRI
DILQPVYFVLPNMKRLFDLAHEDIMGMVHKAMQLGLHAPKFPP
KVAA*

(D)

Ralstonia eutropha (ReP4H) Protein Sequence

MSIATATEAPGAFQGTLTDKLKEQFDAGLLSGQELRPDFTIAQ
PVHRYTSTDHAIWRKLYERQAAMLQGRVSDEFLQGLATLGMDK
DRVPDFDQLNETLMRATGWQVVAVPGLVPDQVFFEHLANRRFP
ASWWMRKPEQLDYLQEPDCFHDVFGHVPLLINPVFADYMEAYG
KGGLKANGLGALDMLSRLYWYTVEFGLIRTAQGLRIYGAGILS
SQGESIYSLDSASPNRIGFDVRRIMRTRYRIDTFQKTYFVIDS
FEQLFDATRPDFAPLYEELRAQPTLGAGDVAPGDQVLNVGTRE
GWADTEDI*

*Xanthomonas campeteris* (XcP4H) Protein Sequence

```
PaP4H    1   MKTTQ                        YVARQ---PD  DNGFIHYPETEHQVWNTLITRQLKVIEGRACQEYLDGIEQLGLPHERIPQLDEINRVL    70
PfP4H    1   MKQTQ                        YVARE---PD  AQGFIDYPPEEHAVWNTLITRQLKVIEGRACQEYLDGIDKLGLPHDRIPQLGEINKVL    70
PpP4H    1   MKQTQ                        YVARE---PD  AHGFIDYPQQEHAVWNTLITRQLKVIEGRACQEYLDGIDQLKLPHDRIPQLGEINKVL    70
ReP4H    1   MSIAT[23]LLSGQelrPD[4]-QPVHRYTSTDHAIWRKLYERQAAMLQGRVSDEFLQGLATLGMDKDRVPDFDQLNETL    99
XcP4H    1   MNTA-[12]YV------PV[6]EQPWDGYSADDHATWGTLYRRQRALLVGRACDEFLQAQDAMGMDDTQIPRFDALNAVL    84

PaP4H   71   QATTGWRVARVPA LIPFQTFFEELLASQQFPVATFIRTPEELDYLQEPDIFHEIFGHCPLLTNPWFAEFTHTYGKLGLKAS   150
PfP4H   71   GETTGWQVARVPA LIPFQTFFEELLASKRFPVATFIRTREELDYLQEPDIFHEIFGHCPLLTNPWFAEFTHTYGKLGLQAT   150
PpP4H   71   GATTGWQVARVPA LIPFQTFFEELLASKRFPVATFIRTPEELDYLQEPDIFHEIFGHCPLLTNPWFAEFTHTYGKLGLAAT   150
ReP4H  100   MRATGWQVVAVPG LVPDQVFFEHLANRRFPASWWMRKPEQLDYLQEPDCFHDVFGHVPLLINPVFADYMEAYGKGGLKAN   179
XcP4H   85   QATTGWTLVGVEQ L_PELDFFDHLANRRFPVTWWIRRPDQIDYIAEPDLFHDLFGHVPLLMNPLFADFMQAYGRGGVKAH   164

PaP4H  151   ---KEERVFLARLYW MTIEFGLVETDQGKRIYGGGILSSPKETVYSLSD-EPLHQAFNPLEAMRTF YRIDILQPLYFVLP   226
PfP4H  151   ---KEERVYLARLYW MTIEFGLVDTPAGRRIYGGGILSSPKETVYSLSE-EPEHQAFDPLEAMRTF YRIDILQPIYFTLP   226
PpP4H  151   ---KEQRVYLARLYW MTIEFGLMETAQGRKIYGGGILSSPKETVYSLSD-EPEHQAFDPIEAMRTF YRIDILQPVYFVLP   226
ReP4H  180   glg--ALDMLSRLYW YTVEFGLIRTAQGLRIYGAGILSSQGESIYSLDSaSPNRIGFDVRRIMRTR YRIDTFQKTYFVID   257
XcP4H  165   gigPDALQNLTRLYW YTVEFGLIATPQGLRIYGAGIVSSKGESLHSLESaAPNRVGFDLQRVMRTR YRIDSFQKTYFVID   244

PaP4H  227   DLKRLFQLAQEDIMALVHEAMRLGLHAPLFPPKQ-AA*                                  263
PfP4H  227   NLKRLFDLAHEDIMALVHQGMQLGLHAPKFPPKPKAA*                                  264
PpP4H  227   NMKRLFDLAHEDIMGMVHKAMQLGLHAPKFPPKV-AA*                                  263
ReP4H  258   SFEQLFDATRPDFAPLYEELRA----QPTLGAGDVAPG[19]                              310
XcP4H  245   SFTQLMDATAPDFTPIYAALAQ----QPQVPAGEVLAT[19]                              297
```

Fig. 5
(G)

```
Homo_sapiens_T5H2           MQPAAMESSKYWARRGFSLDSAVPEEHQLLGSSTLMKENSGRNDEGNKCSSKREA-ATESGKTAVVFSLKEV
Mus_musculus_T5H2           MQPAAMESSKYWARRGISLDSAVPEDHQLLGSLIQRK--AIKSDKKSGKEPGNGD-TIESSKTAVVFSLKEV
Gallus_gallus_T5H2          MQPAAMNESSKYWARRGFSLDSALPEERP--GGLINESSSGKNEDKGNKGNGESVSEGGKRAVVFSLKEV
Bos_taurus_T5H1             ------------------------------------------------MIEDNKEMK-----DHSERGRATLIFSLKEV
Homo_sapiens_T5H1           ------------------------------------------------MIEDNKEMK-----CHELERGRALIFSLKEV
Mus_musculus_T5H1           ------------------------------------------------MIEDNKEMKN--KCHSSERGRVTLIFSLKEV
Gallus_gallus_T5H1          ------------------------------------------------MIEDNKEMK-----DHAPERGREAIFSLKEV
Homo_sapiens_P4H            -------------------------MSTAVLENFSLD5ELLSDFVGQEHSIEDNCNQNGAISLIFSLKEEV
Oryctolagus_cuniculus_P4H   -------------------------MSAVVLENGSLSRKFSDFGQEDSIEDNSNEMSAISLIFSLKEEV
Mus_musculus_P4H            -------------------------MSAVVLENGVLSRKLSDFGQEDSIEDNSNQNGAVSLIFSLKEEV
Bos_taurus_P4H              -------------------------MSALVLESRALGRKLSDFGQEDSIEGMSDQN--AVSLIFSLKEEV
Gallus_gallus_P4H           -------------------------MDAQHCRMN------GDSEQESTVTERRSNKGVISLIFSLKEEV
Xanthomonas_campestris_P4H  ----------------------------------------------------------------------
                            ........|....|....|....|....|....|....|....|....|....|....|....|....|
                                     10         20         30         40         50         60        70

Homo_sapiens_T5H2           GGLVKALRLFEKRPVAVHIESRKSKERRSEVETFVDCECGKTEFNELIQILLKFQTTYVLMPENIWTHEEE-L
Mus_musculus_T5H2           GGLVKALRLFEKRPVAVHIESRKSKERRSEVETFVDCECGKTEFNELIQILLKFQTTVVMLPFSIWTEEED-L
Gallus_gallus_T5H2          GGLVKALRLFEKRPVAVHIESRRGKRRSEVEIFVDCECGKTEFNELIQILLKFQTNIVSIMPEDNIWTDED-L
Bos_taurus_T5H1             GSLIKALKIFEKHVPNLLAIESRKSKRRSEFEIFVDCNIMRQLNDIFHILKSHNLLSVLPDMFTLKEDG-M
Homo_sapiens_T5H1           GSLIKALKIFEKHVANILAIESRSKERMSEFEIFVDCEIMREQLNDIFHLLKSHATVLSVILDMFTLKDG-M
Mus_musculus_T5H1           GSLIVKALKLPQEKHVNLVHIESRKSKRMSEFEIFVDCDISRRQLNDIFPLLESSHATVLSVDSPDQLTAKEDV-M
Gallus_gallus_T5H1          GSLVKALRLPFQEKHVNLVHIESRKSKRRMSEFEIFVDCDSNRQLNDIFVQILRSHVSIVSNETEHFNVQRDGDM
Homo_sapiens_P4H            GALAKVIRLFEENDINLTHIESRFSRLRKDEFFFYLD--RRSLPAIENIIKIIRRDIGATVHELSRDKKKD-
Oryctolagus_cuniculus_P4H   GALARVIRLFENDINLTHIESRFSRLRKDDEFFYLD---RRSMPAIEDIIGILROFDIGATVHELSPDKKKD-
Mus_musculus_P4H            GALAKVIRLFEEADINLTHIESRFSPLINRDEMEFFYLD--RRSKPVLGSIIKSLIKSLRNDIGATVHELSPDKKKN-
Bos_taurus_P4H              GALAKVIRLFEEADINLTHIESRFSRLRKDQEFFFTLH---QRSVPALANIIKLRNDIGATVHELSIVNETKRKD-M
Gallus_gallus_P4H           GALAKVIRFEKGINLHTIESRFSRLINRDDEFFIMLH---GRNVPALDIKIKSLRNDIGVTVHELSATKKKD-
Xanthomonas_campestris_P4H  MDTAPREVEN---------------------------------------------------QLTDRG-----
                            ........|....|....|....|....|....|....|....|....|....|....|....|....|
                                     90        100        110        120        130        140       150
```

*Fig. 5*
(G)
(cont.)

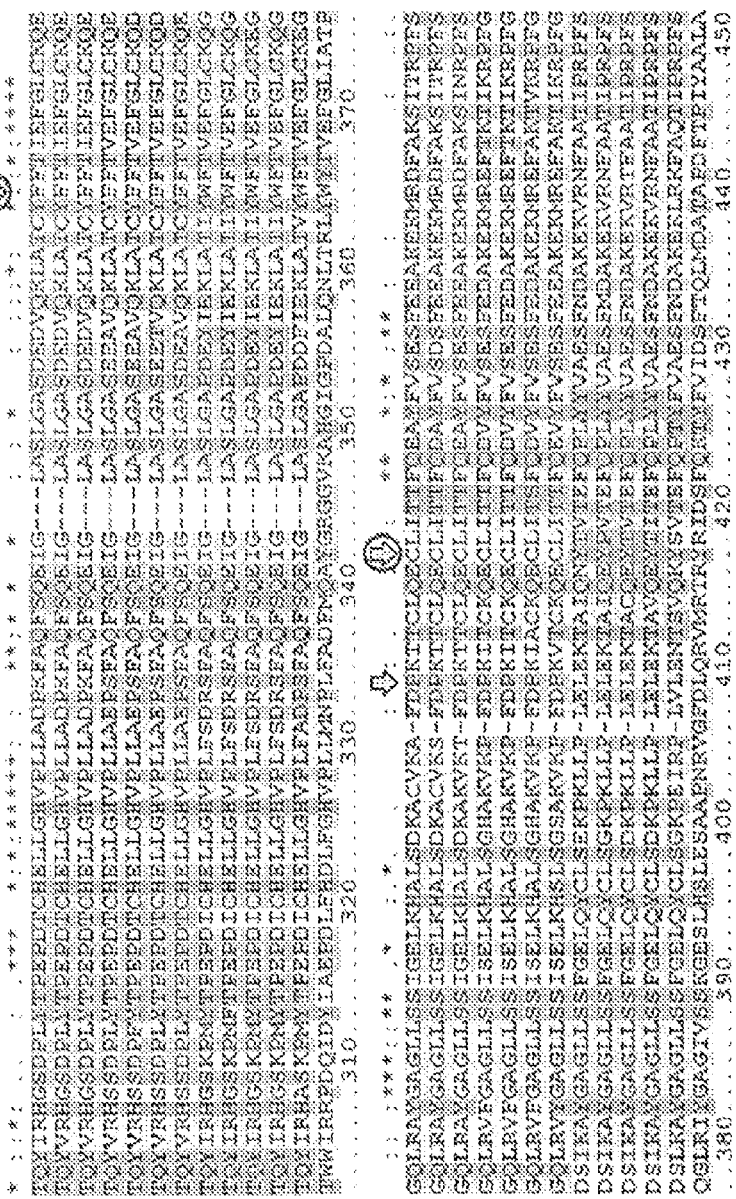
Fig. 5 (G) (cont.)

Fig. 5 (G) (cont.)

```
Homo_sapiens_T5H2              VIENPHKQSIEILKDIRSIENVVQDLRSDINIVCDALNKMRQYLSI----            490
Mus_musculus_T5H2              VYFNPNYQSIEILKDIRSIEMVVQDLRSDINIVCDAIMKMRQYLGI----            488
Gallus_gallus_T5H2             VYFNPHYQIETILKDTRSIENVVQDLRSDINIVCDALSKMNRYLGI----            489
Bos_taurus_T5H1                VKNNPNYPSIQILKDTRITSAMELQHELDVVSDALAKVSRQLSI-----            444
Homo_sapiens_T5H1              VKNDPIYRSIQILKDTKSITSAMELQHDIDVVSDALAKVSRKDSI-----           444
Mus_musculus_T5H1              LKNNPVYKSVVQLADTKSIASVVNELRYDLDVISDALARVTRWPSV----           447
Gallus_gallus_T5H1             VKNDPIYQSVQILADTKSIASVVNELRHELDIYSDALSKMGKQLEV----           445
Homo_sapiens_P4H               VRNDPIYTQRIEVLDNTQLKILADSINSEIGILCSALQKIK--------             452
Oryctolagus_cuniculus_P4H      VRIDPIYTQRIEILDNTQLKILADSINSEVGILCNALQKNKSEAIERIGLSIDHC       466
Mus_musculus_P4H               VRIDPIYTQRVEVLDNTQLKILADSINSEVGILCHALQKIKS--------            453
Bos_taurus_P4H                 VHIDPIYTQRIEVLDNTQLKILADSISSEVEILCSALQMIK--------             451
Gallus_gallus_P4H              VRNNPIYTQRIEVLDMAKQLKNLADTINSMGILCNALQKIK--------             446
Xanthomonas_Campestris_P4H     Q--QPQVPAGEVLATDHVLQRGSGEGWTRDGDV---------------              296
                                    460       470       480       490       500
```

MICROBIAL APPROACH FOR THE PRODUCTION OF 5-HYDROXYTRYPTOPHAN

This application is the National Stage of International Application No. PCT/US2015/030811, filed May 14, 2015, which claims the benefit of U.S. Provisional Application Ser. No. 61/994,413, filed May 16, 2014, each of which is incorporated herein by reference in its entirety.

SEQUENCE LISTING

This application contains a Sequence Listing electronically submitted via EFS-Web to the United States Patent and Trademark Office as an ASCII text file entitled "23502480201_ST25.txt" having a size of 8 kilobytes and created on May 13, 2015. The information contained in the Sequence Listing is incorporated by reference herein.

BACKGROUND

Depression is a common mental disorder that threatens millions of people over the world. A deficit of the neurotransmitter serotonin in the central nervous system (CNS) is thought to be an important physiological factor for depression. 5-Hydroxytryptophan (5-HTP) is the direct biosynthetic precursor to serotonin in humans and animals. It has been shown to be clinically effective in treating depression with relatively few side effects. In most European countries, 5-HTP is a commonly prescribed drug for multiple treatment purposes; while in North America market it is sold as an "over-the-counter" dietary supplement.

In addition to depression, 5-HTP has been shown to be effective in treating insomnia, fibromyalgia, obesity, cerebellar ataxia, chronic headaches, etc. (Birdsall, Altern. Med. Rev. 1998; 3(4):271-280), as evidenced by studies conducted in the past two decades indicating that 5-HTP may have positive effects in the treatment of disorders such as fibromyalgia (Caruso et al., J Int Med Res. 1990; 18:201-209; Puttini et al., J Int Med Res. 1992; 20:182-189), insomnia (Attele et al., Ahern Med Rev. 2000; 5(3):249-259), migraines and headaches (Ribeiro, 2000 June; 40(6):451-6), eating disorders such as polyphagia (Cangiano et al., Int J Obes Relat Metab Disord. 1998; 22:648-654; Ceci et al., J Neural Transm. 1989; 76:109-117) as an aid in the management of obesity and diabetes, and hot flashes (Curcio et al., Ahern Med Rev. 2005; 10(3):216-21; Freedman, Maturitas. 2010 April; 65(4):383-5).

5-HTP is also considered as a potential feed additive for farm animals, as either a preventative of, or therapeutic agent against, mastitis in cattle (Jury et al., PLoS One. 2015 Feb. 17; 10(2):e0117339; Pai et al., Biomed Res Int. 2015; 2015:364746; Horseman et al., Annu Rev Anim Biosci. 2014 February 2:353-74), and in the regulation of lactation function in mammals (Marshall et al., J Mammary Gland Biol Neoplasia. 2014 March; 19(1):139-46; Collier et al., Domest Anim Endocrinol. 2012 August; 43(2):161-70; Hernandez et al., J Endocrinol. 2009 October; 203(1):123-31), thus having great potential to increase milk production by said animals. In certain avians (e.g., chickens) 5-HTP appears to be associated with the regulation of circadian cycle (Thomas et al., Cell. Mol. Neurobiol. 1991, 11(5):511-527) and other positive health effects (Moneva et al., Bulgarian J. Ag Sci. 2008 14(4):424-431) with positive impact in the animal growth and productivity.

Currently, 5-HTP is produced through extraction from the seeds of *Griffonia simplicifolia*, a woody climbing shrub grown in Africa. The season- and region-dependent supply of the raw materials has limited its cost-effective production and broad clinical applications. In addition, *Griffonia* derived 5-HTP has been contaminated with a compound called Peak X, leading the USDA to briefly remove the supplement from shelves in the US.

The current bulk wholesale price for 5-HTP ranges from 400 to 1000 USD/kg. Despite the current high production cost and limited supply, the global market of 5-HTP is still about 120,000 kg (bulk value 50-100 million dollars) with an annual growth rate of about 7%. The 5-HTP end products are even more expensive, and the retail market values of the end products are much higher.

In 2012, North America represented about 48% of the market followed by Europe and Asia Pacific with the major market segment being human nutritional supplement. Emerging market segments (e.g., animal nutrition, human therapeutic co-adjuvant) are likely to grow at rates much higher than those predicted for the over-the-counter human nutritional supplement.

SUMMARY OF THE INVENTION

The present invention provides compounds, compositions, and methods useful for microbial production of 5-hydroxytryptophan (5-HTP), a precursor of serotonin (5-hydroxytryptamine). A host cell is metabolically engineered to express a non-naturally occurring enzyme that catalyzes the conversion of tryptophan to 5-HTP via 5-hydroxylation of tryptophan. A preferred host cell is one that overproduces that starting material, tryptophan. Optionally, the host cell is further engineered to include a cofactor regeneration mechanism, allowing continuous production of 5-HTP without supplementation with exogenous cofactors. The present invention can result in improved titers of 5-HTP and permits low-cost, large scale production without the need for supplementation with precursors or coenzymes.

In one aspect, the invention includes a genetically engineered microbial cell, such as a bacterial or yeast cell, which includes a bacterial phenylalanine-4-hydroxylase enzyme (P4H) that has been modified to show increased affinity for tryptophan compared to the corresponding wild-type P4H. The modified bacterial enzyme can be based on or derived from, for example, a P4H from *Pseudomonas, Chromobacterium, Ralstonia*, or *Xanthomonas*. In one embodiment, the modified bacterial P4H contains an amino acid mutation at any one, any two, or all three of amino acid positions 98, 179, and 231 of *Xanthomonas campestris* P4H, or at any one, any two, or all three corresponding amino acid positions in a bacterial P4H enzyme from another species, preferably a bacterial species (see, e.g., FIG. 5F). Examples of amino acid mutations include any one, any two, or all three mutations selected from the group consisting of L98Y, W179F and Y231C (numbered according to the *X. campestris* P4H amino acid sequence). An exemplary modified phenylalanine 4-hydroxylase (P4H) is an *X. campestris* phenylalanine 4-hydroxylase that incorporates at least the mutation W179F. Optionally, the modified bacterial P4H further includes at least one additional mutation, which additional mutation is at a position corresponding to any one, any two, or all three of amino acid positions 85, 223 and 282 of *X. campestris* P4H, or any one, any two, or all three corresponding amino acid positions in a bacterial P4H enzyme from another species, preferably a bacterial species.

Optionally, the genetically engineered bacterial or yeast cell is a cell that has been genetically engineered to overproduce or accumulate tryptophan.

Optionally, the genetically engineered bacterial or yeast cell includes a cofactor recycling system that includes at least one of a pterin-4α-carbinolamine dehydratase enzyme (PCD) and a dihydromonapterin reductase enzyme (DHMR). Preferably, the cell includes both a pterin-4α-carbinolamine dehydratase enzyme (PCD) and a dihydromonapterin reductase enzyme (DHMR). In one embodiment, the dihydromonapterin reductase (DHMR) is encoded by the *E. coli* gene folM.

The genetically engineered bacterial or yeast cell can contain one or more plasmids encoding any or all of the modified P4H, PCD and/or DHMR enzymes. The enzymes may be encoded by separate plasmids, or two or more enzymes may be encoded by the same plasmid. In some embodiments, the genetically engineered bacterial or yeast cell contains a first plasmid that includes a polynucleotide operably encoding the modified bacterial P4H, and one or both of a pterin-4α-carbinolamine dehydratase (PCD) and a dihydromonapterin reductase (DHMR). The first plasmid can be a low, medium or high copy number plasmid, and is preferably a medium copy number plasmid. Optionally, the genetically engineered cell contains a second plasmid that includes a polynucleotide operably encoding all or a portion of a trp operon, so as to cause the overproduction and/or accumulation of the substrate tryptophan. The second plasmid can be a low, medium, or high copy number plasmid, and is preferably low copy number plasmid. In one embodiment, the trp operon or portion thereof can include a mutation S40F in the TrpE gene. In some embodiments, the genetically engineered bacterial cell does not contain a tetrahydrobiopterin (BH4) cofactor. In other embodiments, the genetically engineered bacterial cell contains an endogenous tetrahydrobiopterin (BH4). Additionally or alternatively, the genetically engineered bacterial cell can contain an endogenous tetrahydromonapterin (MH4) cofactor.

Exemplary genetically engineered bacterial cells include a genetically engineered *Escherichia coli* cell, a genetically engineered *Bacillus subtilis* cell, or a genetically engineered *Corynebacterium glutamicum* cell.

Methods of making and using the genetically engineered cells are also included in the invention.

In another aspect, the invention includes a method of making 5-hydroxytryptophan (5-HTP). The method involves culturing a genetically engineered microbial cell of the invention, preferably a genetically engineered bacterial cell, under conditions and for a time sufficient to produce 5-HTP. Optionally, the 5-HTP can be isolated and/or purified. The method can further include incorporating the 5-HTP into a food product. The food product can be fit for human consumption and/or it can be an animal feed or a beverage. The method can include packaging the 5-HTP or food product for sale and optionally providing instructions for use of the 5-HTP or food product as a food additive, a food supplement, or a nutraceutical. In one embodiment, the food additive, food supplement, or nutraceutical is packaged for use as an animal feed or beverage.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

FIG. 5 shows (A), the amino acid sequence of P4H from *Pseudomonas aeruginosa* (SEQ ID NO:2) (B), the amino acid sequence of P4H from *Pseudomonas fluorescens* (SEQ ID NO:3); (C), the amino acid sequence of P4H from *Pseudomonas putida* (SEQ ID NO:4); (D), the amino acid sequence of P4H from *Ralstonia eutropha* (SEQ ID NO:5); (E), the amino acid sequence of P4H from *Xanthomonas campestris* (SEQ ID NO:1), wherein for (A) through (E), * indicates termination of a protein sequence; (F), an amino acid sequence alignment of P4H enzymes from *P. aeruginosa* (SEQ ID NO:2), *P. fluorescens* (SEQ ID NO:3), *P. putida* (SEQ ID NO:4), *R. eutropha* (SEQ ID NO:5) and *X. campestris* (SEQ ID NO:1), wherein the brackets [ ] indicate the number of amino acids omitted from the graphical depiction of the sequence in order to facilitate alignment, including the termination designator * at the end of the sequence, and wherein candidate mutation sites are indicated at L98, W179, and Y231 (boxed residues), numbered according to the *X. campestris* P4H sequence; and (G), an amino acid sequence alignment of animal AAAHs *Homo sapiens* T5H2 (SEQ ID NO:6), *Mus musculus* T5H2 (SEQ ID NO:7), *Gallus gallus* T5H2 (SEQ ID NO:8), *Bos taurus* T5H1 (SEQ ID NO:9), *Homo sapiens* T5H1 (SEQ ID NO:10), *Mus musculus* T5H1 (SEQ ID NO:11), *Gallus gallus* T5H1 (SEQ ID NO:12), *Homo sapiens* P4H (SEQ ID NO:13), *Oryctolagus cuniculus* P4H (SEQ ID NO:14), *Mus musculus* P4H (SEQ ID NO:15), *Bos taurus* P4H (SEQ ID NO: 16), *Gallus gallus* P4H (SEQ ID NO:17); and XcP4H (SEQ ID NO:1); the circled arrows indicate candidate mutation sites at L98, W179, and Y231 as in (F); the uncircled arrows indicate additional candidate mutation sites at amino acid positions corresponding to *X. campestris* positions Q85, L223, and L282.

DETAILED DESCRIPTION OF ILLUSTRATIVE EMBODIMENTS

Figure 1:
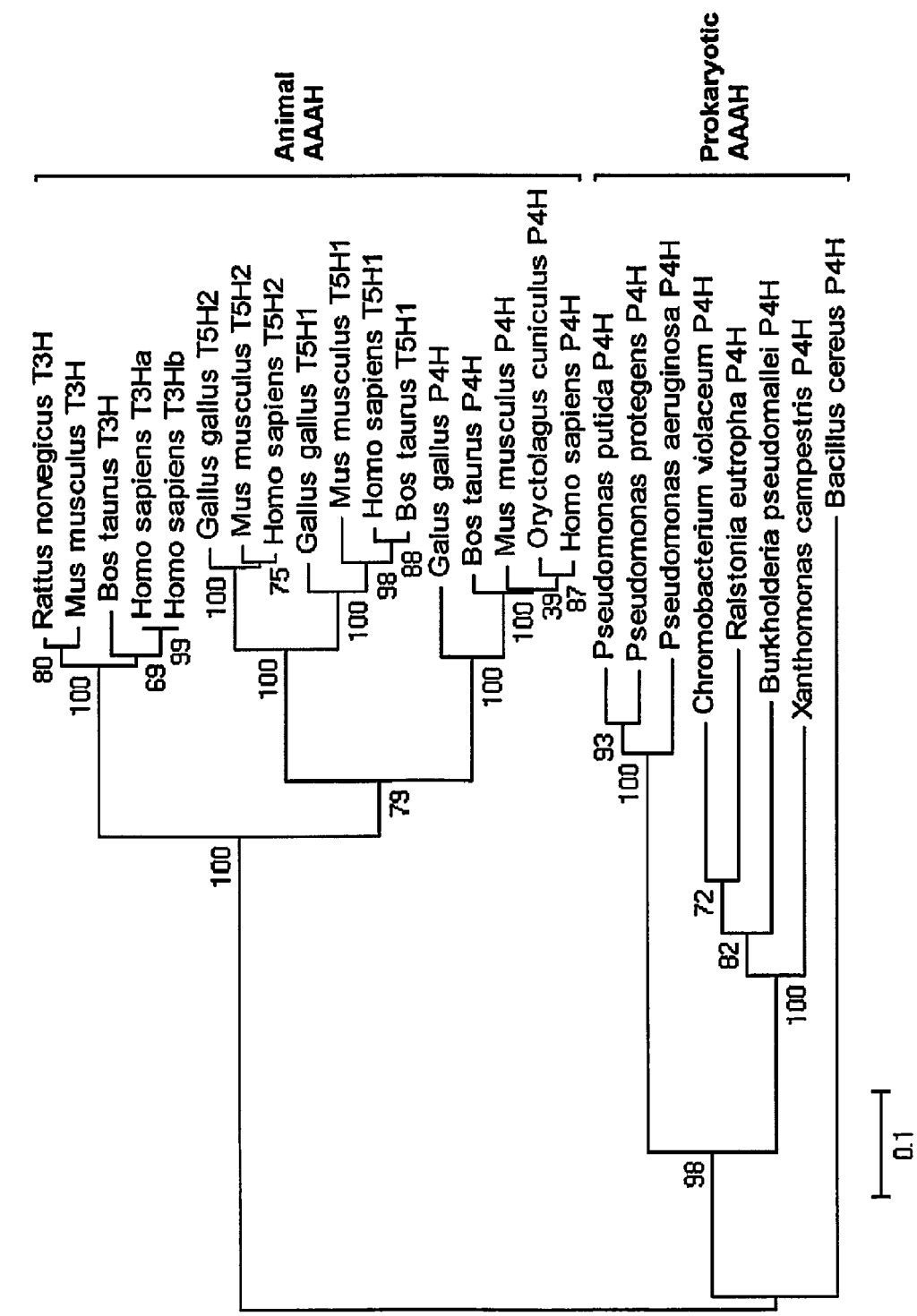
FIG. 1 shows the phylogenetic relationship of prokaryotic phenylalanine 4-hydroxylases (P4Hs) and animal aromatic amino acid hydroxylases (AAAHs); the protein sequence alignment was performed using ClustalX 2.1; the phylogenetic tree was constructed with MEGA 5.02 by using the neighbor-joining method; the bootstrapping method was used for phylogeny test (1000 replications); the numbers associated with the branches refer to the bootstrap values representing the substitution frequencies per amino acid residue.

The present invention provides compounds, compositions, and methods useful for microbial production of 5-hydroxytryptophan (5-HTP). The invention involves metabolically engineering a microbial host cell to express a non-naturally occurring hydroxylase enzyme, preferably a hydroxylase that is of microbial origin, that catalyzes the conversion of tryptophan to 5-HTP via 5-hydroxylation of tryptophan. Genetically engineered cells are referred to herein as "metabolically engineered" cells when the genetic engineering is directed to disruption or alteration of a metabolic pathway so as to cause a change in the cell's metabolism.

A preferred microbial host cell is one that overproduces that starting material, tryptophan. Optionally, the microbial host cell is further engineered to include a cofactor regeneration mechanism, allowing continuous production of 5-HTP without supplementation of exogenous cofactors.

Microbial enzymes that catalyze the conversion of tryptophan to 5-HTP via 5-hydroxylation of tryptophan (referred to as tryptophan hydroxylase, "TPH" or "T5H" enzymes) are not known. Some animals possess a tryptophan hydroxylase capable of catalyzing this reaction (utilizing a pterin cofactor, typically tetrahydrobiopterin, also known as "BH4"); however, due to factors such as low solubility, low stability, and inefficient or absent post-translational modification mechanisms, expression of a eukaryotic 5-hydroxylase in microbial systems has proven problematic. Some microbes possess a 4-hydroxylase that catalyzes the conversion of phenylalanine to tyrosine ("P4H" enzymes), but this enzyme possesses little or no 5-hydroxolase activity for the substrate tryptophan.

This unique biotechnological production process of the present invention combines protein engineering and metabolic engineering to achieve microbial production of 5-HTP. Protein engineering, for example site-directed mutagenesis, is employed to produce an effective, non-naturally occurring hydroxylase enzyme that effectively catalyzes the conversion of tryptophan to 5-HTP, using site-directed mutation of a naturally occurring microbial enzyme, such as a phenylalanine-4-hydroxylase (P4H). The mutated naturally occurring microbial enzyme is referred to herein as a "modified" enzyme, for example, a modified bacterial phenylalanine-4-hydroxylase (P4H). A modified enzyme that is "derived from" a particular organism means a modified enzyme that has been created by mutating the amino acid sequence of the wild-type enzyme produced by that organism, for example by way of one or more site mutations at specified amino acid positions. This engineered or "modified" microbial-origin enzyme is better suited for use in a microbial host cell than its eukaryotic counterparts. Metabolic engineering is used to alter one or more metabolic pathway involved in the production or accumulation of tryptophan within the cell, and/or to incorporate a heterologous cofactor regeneration system into the host cell. Bacterial cofactors that can be recycled by way of a heterologous cofactor regeneration system include tetrahydropterins such as tetrahydromonapterin (MH4) and tetrahydrobiopterin (BH4). Incorporation of a tetrahydromonapterin (MH4) cofactor regeneration system into an *E. coli* cell, for example, allows the use of the endogenous *E. coli* MH4 as an efficient hydrogen donor.

The present invention provides a cost-effective microbial process for the efficient production of 5-HTP from inexpensive carbon sources such as tryptophan and glucose. This technology is expected to facilitate creation of a biocatalytic platform to convert cheap feedstock to the high purity product 5-HTP, which will dramatically lower its production cost compared with the conventional extraction approach, greatly improve its availability to the less well-treated patients, and further expand its market.

Host Cell

The invention makes possible the production of 5-HTP in a host cell, preferably a microbial host cell such as a bacterial or yeast cell. Exemplary bacterial host cells include *Escherichia coli*, *Bacillus* spp., such as *B. subtilis*, *Lactobacillus* spp., such as *L. acidophilus*, *Bifidobacteria* and *Corynebacterium* spp., such as *C. glutamicum*. Exemplary yeast cells include yeasts from the genus *Saccharomyces* (e.g., *S. cerevisiae*) and the genus *Pichia*. Yeast cells may contain an endogenous cofactor, BH4; in some embodiments, a BH4 cofactor recycling system is introduced into the host yeast cell, in addition to or instead of the MH4 cofactor recycling system described herein.

In a preferred embodiment, the invention provides for the introduction of bacterial P4H activity into a bacterial cell, for example *E. coli* or *B. subtilis* (which have not been shown to contain a native NH enzyme) via the introduction of a modified bacterial P4H from a different microbe (for example, and without limitation, *Pseudomonas*, *Chromobacterium*, *Ralstonia*, or *Xanthomonas*), which modified enzyme advantageously and surprisingly is able to utilize an endogenous *E. coli* cofactor, MH4 (typically, the pterin cofactor BH4 is associated with AAAH enzymes) In another preferred embodiment, the *E. coli* cell is further engineered to contain a recycling system to recycle MH4 as described herein.

Optionally, the host cell is genetically engineered to increase the amount of tryptophan in the cell, i.e., to overproduce and/or accumulate tryptophan, the starting material for the biosynthesis of 5-HTP. Overproduction or accumulation of tryptophan can be achieved through a variety of methods. In one embodiment, overproduction or accumulation of tryptophan can be achieved by knocking out one or more enzymes involved in tryptophan degradation. For example, the amount of tryptophan in a cell can be increased by knocking out the gene for tryptophanase (tnaA), a protein reported to catalyze the degradation of tryptophan and 5-HTP. Alternatively or additionally, pheA, pheLA, and/or tyrA can be downregulated or knocked out to increase the amount of tryptophan in a cell.

In another embodiment, tryptophan overproduction or accumulation can be achieved by increasing the biosynthesis of tryptophan. For example, the host cell can be engineered to overexpress the trp operon or portions thereof. A gene product, such as an enzyme or regulatory protein, is "overexpressed" in a metabolically engineered cell when the gene product is expressed in the metabolically engineered cell at a level higher than the level at which it is expressed in a comparable wild-type cell. In cells that do not endogenously express a particular gene product, any level of expression of that gene product in the cell is deemed an "overexpression" of that gene product for purposes of the present invention. Typically, as a means to overexpress one or more gene products from the trp operon, additional copies of the trp operon are introduced into the cell on a plasmid, cosmid or other DNA or RNA vector. In one embodiment, the host cell is engineered to overexpress the complete trp operon, including trpEDCBA. In another embodiment, the host cell is engineered to overexpress only portion of the trp operon, for example op ED or trpE.

Optionally, the op operon is engineered to reduce or eliminate feedback inhibition. For example, a mutation at amino acid position S40, such as the mutation S40F, can incorporated into TrpE to reduce or eliminate feedback inhibition.

In another embodiment, tryptophan overproduction or accumulation can be achieved altering the host cell's endogenous tryptophan expression. For example, tryptophan overproduction or accumulation can be achieved by altering expression of, downregulating or inactivating the tryptophan transcriptional repressor protein (TrpR).

In another embodiment, tryptophan overproduction or accumulation can be achieved by overproducing a precursor to tryptophan biosynthesis, such as chorismate. A host cell can be engineered to express or overexpress one or more enzymes that increase chorismate availability. Several rate limiting steps in the production of chorismate are known and can be manipulated to result in a microbe that produces more chorismate. Enzymes that increase carbon flow toward chorismate include, for example, shikimate kinase, phosphoenolpyruvate synthase, transketolase, and 3-deoxy-D-arabino-heptulosonate-7-phosphate synthase, preferably feedback-inhibition-resistant 3-deoxy-D-arabino-heptulosonate-7-phosphate synthase, 3-dehydroquinate synthase, 3-dehydroquinate dehydratase, shikimate dehydrogenase, 3-phosphoshikimate-1-carboxyvinyltransferase, and chorismate synthase. Examples of enzymes include, but are not limited to, AroL, AroF, AroH, AroG, PpsA, and TktA. In some embodiments, one or more of the AroL, AroF, AroH, AroG enzymes may be in the form of feedback-inhibition-resistant (fbr) enzymes. Exemplary polynucleotides which encode preferred enzymes are aroL, ppsA, tktA, and aroG$^{fbr}$, respectively. In one embodiment, an *E. coli* host cell can express aroL, ppsA, tktA, and aroG$^{fbr}$ to increase chorismate availability. Exemplary enzymes are also described in Lin et al., *Metab Eng.* 2014, 23:62-9; Lin et al., *Nat. Commun.* 2013, 4:2603; and US Patent Application Publication No. 2014/0370557, published Dec. 18, 2014; each of which is incorporated by reference herein.

In another embodiment, tryptophan overproduction or accumulation can be achieved by inactivation of the tryptophan transcriptional repressor protein (TrpR). In yet another embodiment, tryptophan overproduction or accumulation can be achieved by inactivation of the transcriptional regulator protein TyrR.

Any known method for overproduction or accumulation of tryptophan can be used, including, for example, the methods described in U.S. Pat. No. 5,756,345 and Chinese Patent CN 102453691 B; see also Zhao et al., *J. Ind. Microbiol. Biotechnol.,* 2011, 39:1921-1929.

Optionally, one or more overproduction or accumulation techniques can be combined. For example, the tryptophan-degradation pathway can be knocked out, and the host cell can overexpress the entire trp operon. As another example, the host cell can overexpress the entire trp operon as well as one or more enzymes to increase the production of the tryptophan precursor chorismate. When the host cell is engineered to express or overexpress a plurality of enzymes, a single exogenous construct, such as a plasmid, can be utilized, or multiple exogenous constructs, such as plasmids, can be utilized, as described in more detail herein. Alternatively or additionally, genetic engineering can be accomplished using chromosomal additions, deletions, or mutations.

Engineered Hydroxylase

In the present invention, a modified bacterial hydroxylase, rather than a eukaryotic hydroxylase (see, e.g., WO2013127914A1), is advantageously utilized to catalyze the conversion of tryptophan to 5-HTP. The use of a modified bacterial hydroxylase in a bacterial host cell permits the use of endogenous bacterial cofactors, which may include MH4 and/or BH4, and can avoid limitations associated with the use of eukaryotic enzymes including low solubility, low stability, and inefficient or absent post-translational modification mechanisms and/or cofactors (see, e.g., McKinney et al. (2004), Protein Expr. Purif. 33(2):185-194; Martinez et al. (2001) Curr. Med. Chem. 8(9):1077-1091). In contrast to animal 5-hydroxylases that have been truncated to improve solubility (see, e.g., WO2013/127914 A1), the modified bacterial 4-hydroxylases of the present invention demonstrate increased catalytic efficiency.

Naturally occurring bacterial phenylalanine 4-hydroxylases (P4H) have little activity towards tryptophan. The invention involves the expression in the host cell of a bacterial hydroxylase, preferably a 4-hydroxylase, more preferably a phenylalanine 4-hydroxylase, that has been modified to increase its 5-hydroxylase activity toward the substrate tryptophan. Preferably, the modification is achieved through site-directed mutagenesis. Not all bacteria contain P4H enzymes, but any bacterial P4H enzyme can be modified according the invention to increase its activity toward tryptophan. Suitable bacterial P4H enzymes that can be modified according to the invention to increase their activity toward tryptophan include, without limitation, P4H enzymes from *Pseudomonas, Chromobacterium, Ralstonia, Burkolderia, Xanthomonas, Bacillus, Stenotrophomonas, Arenimonas, Lysobacter, Dyella, Rhodanobacter, Cupriavi-* dus, Sphingobium, Polaromonas, Micavibrio, Caulobacter, and the like. Exemplary species include *C. violaceum, P. putida, P. protegens, P. aeruginosa, R. eutropha, B. pseudomallei, X. campestris*, and *B. cereus*. Preferred bacterial P4H enzymes include those from *Pseudomonas aeruginosa* (PaP4H), *Pseudomonas putida* (PpP4H), *Pseudomonas fluorescens* (PfP4H), *Ralstonia eutropha* (ReP4H), and *Xanthomonas campestris* (XcP4H). A preferred bacterial P4H enzyme is XcP4H. Bacterial P4H may be encoded by the gene phhA.

Figure 5:
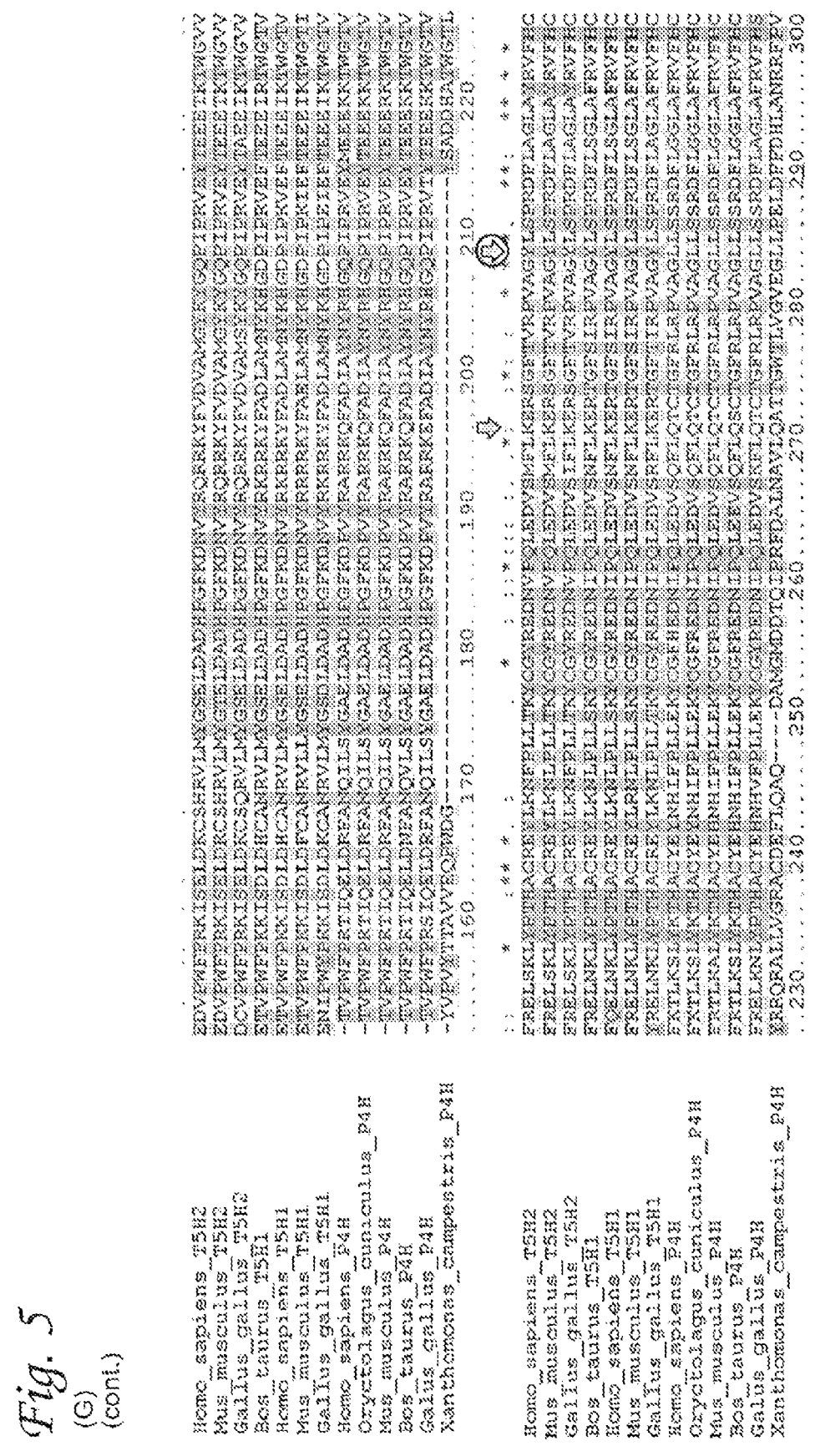

The bacterial P4H enzyme is mutated at one more residues to produce a modified P4H enzyme with greater activity toward tryptophan. As an example, XcP4H can be mutated at residues W179, L98, Y231, Q85, L223, and/or L282. In one embodiment, XcP4H is mutated at residues W179, L98, and Y231. In other embodiments, XcP4H is mutated only at a single residue, for example only at residue W179, only at residue L98, or only at residue Y231. In other embodiments, XcP4H is mutated at two or more residues, for example, residues W179 and L98; or at W179 and Y231; or at L98 and Y231. In a preferred embodiment, W179 is replaced with the amino acid phenylalanine (F). In another embodiment, L98 is replaced with tyrosine (Y). In yet another embodiment, Y231 is replaced with cysteine (C). In one embodiment, XcP4H includes mutations at each of the following residues: W179F, L98Y, and Y231C. In other embodiments, XcP4H contains the following mutations: W179F and L98Y; or W179F and Y231C; or L98Y and Y231C. One or more corresponding residues in bacterial P4H enzymes PaP4H, PpP4H, PfP4H, and ReP4H (see, e.g., FIG. 5F) or any other microbial or animal P4H enzyme (see, e.g., FIG. 5G) could also be mutated at one or more corresponding amino acid positions to produce the modified P4H enzyme with enhanced preference for tryptophan. Preferably, a bacterial P4H enzyme (exemplified by the sequences in FIG. 5F) is modified to produce the modified P4H enzyme. However, animal enzymes can also be used. FIG. 5G shows exemplary animal P4H and T5H amino acid sequences aligned with bacterial P4H from *Xanthomonas campestris*; amino acid positions corresponding to XcP4H positions W179, L98Y, and Y231C are indicated with circled arrows, and amino acid positions corresponding to XcP4H positions Q85, L223, and L282 are indicated with uncircled arrows. Any one, some or all of these positions are candidates for mutation to produce a modified P4H enzyme of the invention.

Cofactor Recycling

Optionally, the invention further provides for the increased production of and/or recycling of a cofactor for the modified P4H enzyme. The cofactor can be a pterin, such as a tetrahydropterin exemplified by tetrahydrobiopterin (BH4) or tetrahydomonapterin (MH4). Preferably, the cofactor used by the modified P4H enzyme is endogenous to the host cell. In a preferred embodiment, the cofactor is a bacterial MH4, for example *E. coli* MH4.

Advantageously, a cofactor regeneration mechanism can be introduced into the host cell to facilitate recycling of the endogenous pterin cofactor (e.g. MH4 or BH4) and thereby promote increased overproduction or accumulation of 5-HTP. To this end, the host cell is preferably engineered to express a pterin 4a-carbinolamine dehydratase (PCD), a dihydromonapterin reductase (DHMR), or both, so as to allow recycling of the MH4 or BH4 pterin cofactor used by the P4H enzyme. The PCD and/or DHMR enzymes can be native to the host cell (in which case the cell is engineered to overexpress the enzyme) or they can be heterologous (foreign) to the host cell. In some embodiments, one of the enzymes is native, and the other is foreign. Preferably the enzymes are bacterial enzymes, although they may be eukaryotic. A preferred PCD is from *P. aeruginosa*, but a suitable PCD can be obtained from any convenient prokaryote or eukaryote, preferably a bacterium or yeast having an endogenous P4H enzyme. A preferred DHMR is form *E. coli*, but a suitable DHMR can be obtained from any prokaryote or eukaryote.

Plasmids

The modified bacterial P4H, the optional enzymes involved in recycling its cofactor, and the optional trp operon, or portions of the trp operon, as well as any other enzymes of interest, can be expressed or overexpressed in the host cell through the introduction of one or more plasmids containing polynucleotide sequences that operably encoding the enzyme(s). Suitable exemplary plasmids are described in Example I and include but are not limited to pZE12-luc, pCS27, and pSA74. A person having skill in the art will appreciate that additional plasmids with different promoters, antibiotic resistance, and origins of replication (ori) can also be used.

Additionally, it should be noted that any or all of the nucleotide sequences that operably encode the enzymes described herein can instead be genomically integrated into the bacterial genome, if desired, using well-known genetic engineering techniques and protocols.

The plasmid can be a high-copy number, a medium copy-number, or a low-copy number plasmid. While the boundaries associated with the art-recognized designations "high," "medium" and "low" copy number are indistinct and may in practice overlap, in general a high copy number plasmid is characterized by copy numbers within a cell of, for example, greater than 50 or 60 copies, a medium copy number plasmid is characterized by copy numbers within a cell of, for example, between 10 and 60 copies (e.g., 15-20 copies), and a low copy number plasmid is characterized by copy numbers within a cell of, for example, fewer than 10 or 15 copies (e.g., 3-8 copies). Plasmids pZE12-luc, pCS27, pSA74 exemplify high-, medium- and low-copy number plasmids, respectively. In some embodiments, pZE12-luc has a copy number of about 60-70, pCS27 has a copy number of about 15-20, and pSA74 has a copy number of about 5-10.

Expression of P4H, preferably a modified bacterial P4H, can be achieved by introducing into the host cell a plasmid containing phhA encoding the modified P4H, preferably phhA that has been mutated to encode a modified P4H with greater activity toward the substrate tryptophan, as described herein. The phhA that encodes the modified P4H can be obtained from any suitable organism, such as, for example and without limitation, *P. aeruginosa* (FIG. 5A, SEQ ID NO:2), *P. fluorescens* (FIG. 5B, SEQ ID NO:3), *P. putida* (FIG. 5C, SEQ ID NO:4), *R. eutropha* (FIG. 5D, SEQ ID NO:5) and *X. campestris* (FIG. 5E, SEQ ID NO:1), as described herein.

Expression of one or more enzymes involved in cofactor recycling, such as PCD and/or DHMR, can be achieved by introducing into the host cell a plasmid containing, for example, phhB (encoding PCD from, for example, *P. aeruginosa*) and/or folM (encoding DHMR from, for example, *E. coli*). Polynucleotide sequences encoding PCD and DHMR can be obtained from any suitable organism; for example, they can be obtained from a microorganism that endogeneously expresses P4H.

In one embodiment, phhA (mutated to encode a modified P4H with greater activity toward tryptophan), phhB, and folM are cloned into two or more separate plasmids. In a preferred embodiment, phhA (mutated as described), phhB, and folM are cloned into the same plasmid. Preferably, the genes are cloned into a medium-copy number plasmid, for example, pCS27, although high copy number and low copy number plasmids can be used.

The trp operon, or portions of the trp operon, can also be expressed or overexpressed in the host cell by means of a plasmid. The trp operon can include mutations, including but not limited to, mutation S40F in TrpE. In an exemplary embodiment, the trp operon including mutation S40F is cloned into a low copy number plasmid, such as pSA74 to make pSA-TrpEDCBA, although medium copy number and high copy number plasmids may be used.

Method of Making 5-HTP

Microbial host cells expressing the modified bacterial P4H and other features as described herein, such as a cofactor recycling system and/or tryptophan overproduction or accumulation, can advantageously be grown in a medium containing a simple carbon source such as glucose or glycerol. Other suitable carbon sources include xylose, arabinose, and other renewable sugars, such as sugars present in a plant or lignocellulosic hydrolysate. Optionally, the medium is supplemented with tryptophan. In order to optimize cell growth and production efficiency, the host cells can be incubated at a temperature, including but not limited to 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C. In one embodiment, the host cells are incubated at 30° C. In an alternative embodiment, the host cells are incubated at 37° C. Glucose is preferably used as carbon source for cell growth and maintenance (e.g., 0.1-100 g/L); optionally, citrate can be added to promote cell growth increase the titer (e.g., 0.1-100 g/L); optionally, other growth supplements such as tryptone can be added.

Optionally, 5-HTP is isolated from the host cell. The isolated 5-HTP may be purified. The purified 5-HTP may be used as the starting material for other chemical or enzymatic reactions to produce other biochemicals of interest, such as melatonin.

Optionally, the isolated 5-HTP is incorporated into a food product as a food additive, food supplement, or nutraceutical. For example, the isolated 5-HTP can be incorporated into an animal feed, such as feed for domestic or farm animals. Supplementation with 5-HTP can have beneficial effects relating to calcium metabolism and is especially suitable for pregnant and lactating farm animals such as cows. The method of making 5-HTP therefore optionally includes packaging and/or marketing the 5-HTP as an animal food supplement, additive or nutraceutical, as well as incorporating the 5-HTP into a food product such as an animal feed or beverage.

Advantageously, in host cells that have been engineered to contain the cofactor recycling system as described herein, there is no need to supplement with expensive pterin coenzymes or precursors; the cells can utilize simple renewable carbon sources. The method thus holds great potential for scale-up production of 5-HTP.

The present invention is illustrated by the following examples. It is to be understood that the particular examples, materials, amounts, and procedures are to be interpreted broadly in accordance with the scope and spirit of the invention as set forth herein.

EXAMPLES

Example I. Engineering Bacterial Phenylalanine 4-Hydroxylase for Microbial Synthesis of Human Neurotransmitter Precursor 5-Hydroxytryptophan 5-Hydroxytryptophan (5-HTP) is a clinically effective drug against depression, insomnia, obesity, cerebellar ataxia, chronic headaches, etc. It is only commercially produced by the extraction from the seeds of *Griffonia simplicifolia* due to lack of synthetic methods. Here, we report the efficient microbial production of 5-HTP via combinatorial protein and metabolic engineering approaches. Instead of using the less tractable animal tryptophan 5-hydroxylase, we attempted to modify a bacterial phenylalanine 4-hydroxylase (P4H) to alter its substrate specificity. First we reconstituted and screened prokaryotic phenylalanine 4-hydroxylase (P4H) activity in *Escherichia coli*. Then, we used sequence and structure-based protein engineering to dramatically shift its substrate preference, allowing for efficient conversion of tryptophan into 5-HTP. Importantly, *E. coli* endogenous tetrahydromonapterin (MH4) was able to be utilized as the coenzyme, when a foreign MH4 recycling mechanism was introduced. Whole-cell bioconversion enabled the high-level production of 5-HTP (1.1-1.2 g l$^{-1}$) from tryptophan in shake flasks. Metabolic engineering efforts were further made to achieve the de novo 5-HTP biosynthesis from glucose. See Lin et al., ACS Synth. Biol., 2014, 3(7), pp 497-505. This process does not require the supplementation of expensive pterin coenzymes or precursors, and is able to utilize renewable carbon sources. This work not only holds great scale-up potential but also demonstrates a strategy to expand native metabolism of microorganisms.

Introduction

The World Health Organization (WHO) reported that depression is a common mental disorder affecting more than 350 million people globally. It results in around one million suicides per year. Unfortunately, over 50% of sufferers over the world (over 90% in some regions) have never received medical treatment[1]. Alterations in serotonin (5-hydroxytryptamine) metabolism were thought to be an important physiological factor for depression[2]. Dysfunction of the serotonergic mechanism in the central nervous system (CNS) has been implicated in the etiology of depression[3]. However, supply of serotonin via oral administration is not clinically effective against depression because it cannot pass through the brain-blood barrier. Unlike the conventional antidepressants (e.g. selective serotonin re-uptake inhibitors) acting on minimizing serotonin loss, 5-hydroxytryptophan (5-HTP) functions as the direct precursor to increase serotonin supply. Orally administered 5-HTP can easily pass through the blood-brain barrier without requiring transport molecules. Then it can be efficiently converted into serotonin in the CNS by endogenous decarboxylase[3,4]. Detailed clinical trials have demonstrated its efficacy in alleviating depression symptoms. Meanwhile, the therapeutic administration of 5-HTP has been shown to be effective in treating insomnia, fibromyalgia, obesity, cerebellar ataxia, and chronic headaches[4]. Importantly, relatively few adverse effects are associated with its use in treatment[2]. In most European countries, 5-HTP is a commonly prescribed drug for multiple treatment purposes; while in North America it is sold as an "over-the-counter" dietary supplement.

Due to the difficulty in regio-selective hydroxylation of tryptophan via chemical approaches, the commercial production of 5-HTP relies only on the isolation from the seeds of *Griffonia simplicifolia*, a woody climbing shrub grown in West and Central Africa[3,4]. The season- and region-dependent supply of the raw materials has been largely limiting its cost-effective production and broad clinical applications. The recent development of metabolic engineering and protein engineering in combination with fundamental genetics, biochemistry and bioinformatics is providing new strategies to synthesize natural and non-natural molecules using microbial systems. On the basis of accumulated knowledge on natural biosynthetic mechanisms of target products, especially the genetic and biochemical information of the involved enzymes, heterologous enzymatic reactions can be reconstituted, modified and optimized in genetically superior microbial hosts to achieve efficient production of pharmaceutically important compounds that are scarce in nature[5-11].

5-HTP is natively produced in humans and animals from L-tryptophan by the action of tryptophan 5-hydroxylase (T5H) and then converted to the neurotransmitter serotonin under normal physiological conditions[4]. T5Hs belong to the class of pterin-dependent aromatic amino acid hydroxylases (AAAHs) that also include two other subgroups: phenylalanine 4-hydroxylases (P4Hs) and tyrosine 3-hydroxylases (T3Hs). AAAHs were broadly identified and extensively studied in animals due to their close relationship with human diseases such as phenylketonuria, Parkinson's disease, and neuropsychiatric disorders[12]. These enzymes consist of three domains that are the N-terminal regulatory domain, the central catalytic domain, and the C-terminal domain involved in tetramer formation, and usually utilize tetrahydrobiopterin (BH4) as the coenzyme (or co-substrate)[13]. Animal T5Hs were proved to be unstable and hard to be functionally expressed in a microbial host[14,15]. A very recent patent reported the use of truncated T5H1 from *Oryctolagus cuniculus*, which produced up to 0.9 mM (equivalent to 198 mg l$^{-1}$) of 5-HTP from tryptophan in *Escherichia coli*. To supply the pterin coenzyme, the animal BH4 biosynthetic pathway coupled with a regeneration system including a total of five enzymes was required to be co-expressed in *E. coli*[16]. However, the production efficiency is still not satisfying for scale-up production.

A few AAAHs were also found in bacteria such as *Pseudomonas* and *Chromobacterium* species[17,18]. So far, all of them were identified as P4Hs with little activity for tryptophan hydroxylation; but such activity was reported to be improved in vitro when mutations were introduced into the P4H from *Chromobacterium violaceum*[19]. Prokaryotic P4Hs consist of only one domain corresponding to the catalytic domain of animal AAAHs[13]. Recent experimental evidence indicated that bacterial P4Hs may utilize tetrahydromonapterin (MH4) instead of BH4 as the native pterin coenzyme[20], since BH4 does not naturally occur in most bacteria. Interestingly, MH4 is the major form of pterin in *E. coli*, although its function is still unknown. In this work, we report the reconstitution of bacterial P4H activity in *E. coli* through utilization and recycling of its endogenous MH4. Combined bioprospecting and protein engineering approaches enabled the development of the P4H mutants that are highly active on converting tryptophan to 5-HTP, which allowed the establishment of an efficient 5-HTP production platform via further metabolic engineering efforts. This de novo process does not require supplementation of expensive pterin co-factors or precursors but only utilizes renewable simple carbon sources, which holds great potential for scale-up production of 5-HTP in microorganisms.

Results and Discussion

Phylogenetic Analysis of Aromatic Amino Acid Hydroxylases (AAAHs).

Compared with animal AAAHs that include three subgroups, their prokaryotic counterparts were all identified or annotated as P4H only. Previous biochemical and structural studies revealed that in addition to the central catalytic domain, animal AAAHs usually consist of two additional domains that are the N-terminal regulatory domain and the C-terminal domain involved in tetramer formation; while prokaryotic AAAHs (e.g. the P4H from *C. violaceum*) are monomers with only one single domain that shares moderate sequence similarity (about 30%) with the catalytic domains of animal AAAHs[21]. To explore the evolutionary relationship among AAAHs, 25 amino acid sequences from both prokaryotes and animals were randomly selected and a phylogenetic tree was constructed using MEGA 5.02 based on the neighbor joining method (FIG. 1)[22]. The tree reflects a considerable evolutionary separation between prokaryotic and animal AAAHs. The three subfamilies (P4Hs, T5Hs, and T3Hs) of animal AAAHs are distinctly separated as well, among which P4Hs show closer phylogenetic relationship with T5Hs than with T3Hs. These results are consistent with a previous phylogenetic study on AAAHs[23].

Considering the phylogenetic evidence in combination with the development of functional diversity, we inferred that the animal AAAHs were evolved from prokaryotic P4Hs through duplication and divergence. Therefore, we hypothesized that even after a long-term evolution process, prokaryotic and animal P4Hs may still share some conserved amino acid residues that determine their substrate preference towards phenylalanine. Meanwhile, animal P4Hs and T5Hs share high sequence similarity, suggesting that the interchange of substrate preference from phenylalanine to tryptophan may only involve the substitution of a small number of residues. Based on these hypotheses, we speculated that by performing a comprehensive alignment analysis of the sequences of animal AAAHs and prokaryotic P4Hs, we may be able to identify the substrate-determining residues from the latter group and artificially evolve them into T5Hs.

Bio-Prospecting and Reconstitution of Prokaryotic P4Hs in *E. coli*.

Figure 2:
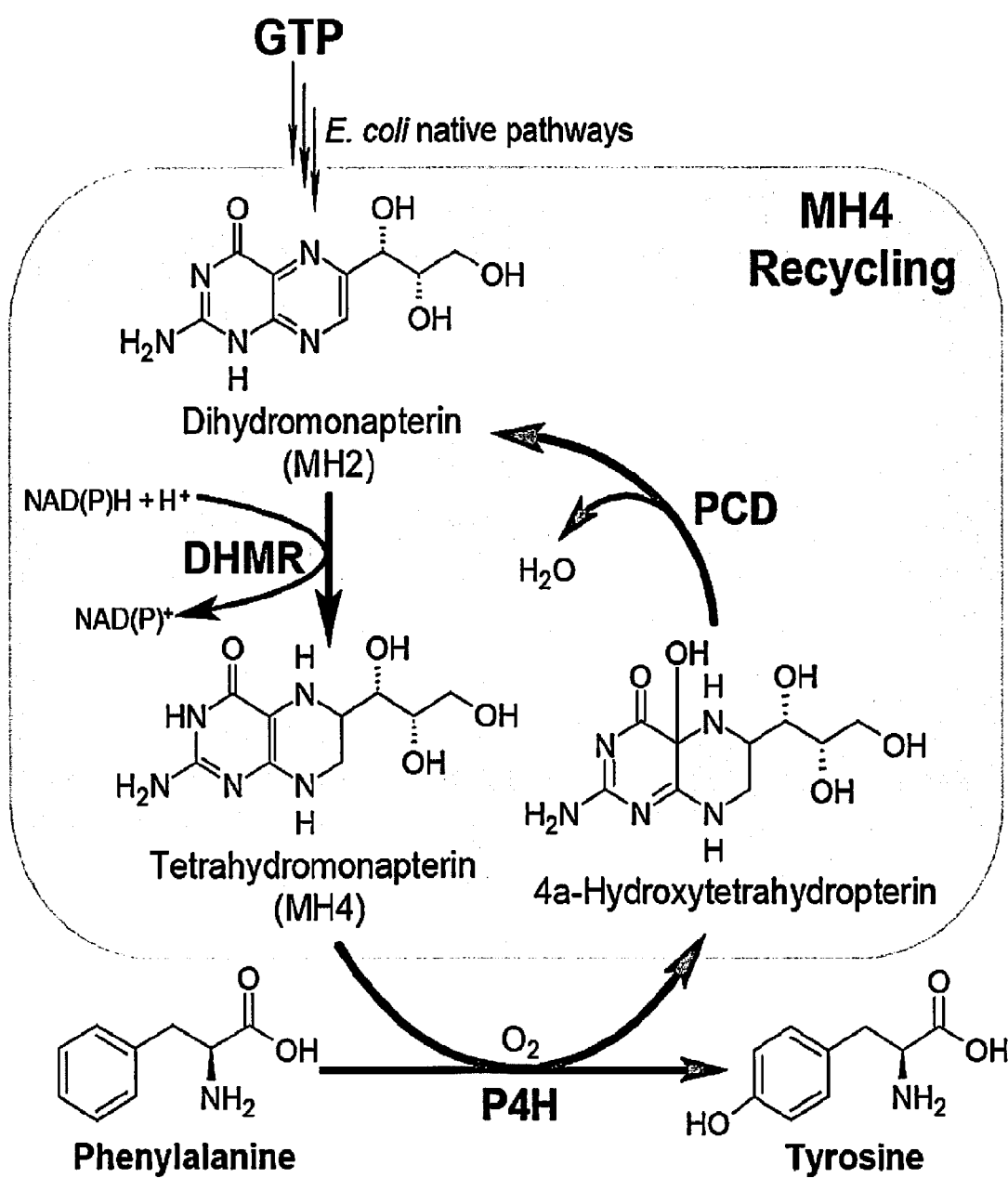
FIG. 2 shows (A) reconstitution of prokaryotic P4H activity in *E. coli*; wherein the black- and grey-colored arrows indicate the *E. coli* native pathways and heterologous reactions, respectively; bold arrows refer to the over-expressed steps; the introduced MH4 recycling system is indicated by the grey-colored box, and abbreviations are as follows: GTP, guanosine-5'-triphosphate; PCD, pterin-4α-carbinolamine dehydratase; DHMR, dihydromonapterin reductase; P4H, phenylalanine 4-hydroxylase; and (B) introduction of modified bacterial P4H activity into the *E. coli* cell of (A), further allowing for the de novo production of 5-hydroxytryptophan (5-HTP) from simple carbon sources, such as sugars.
Figure 2:
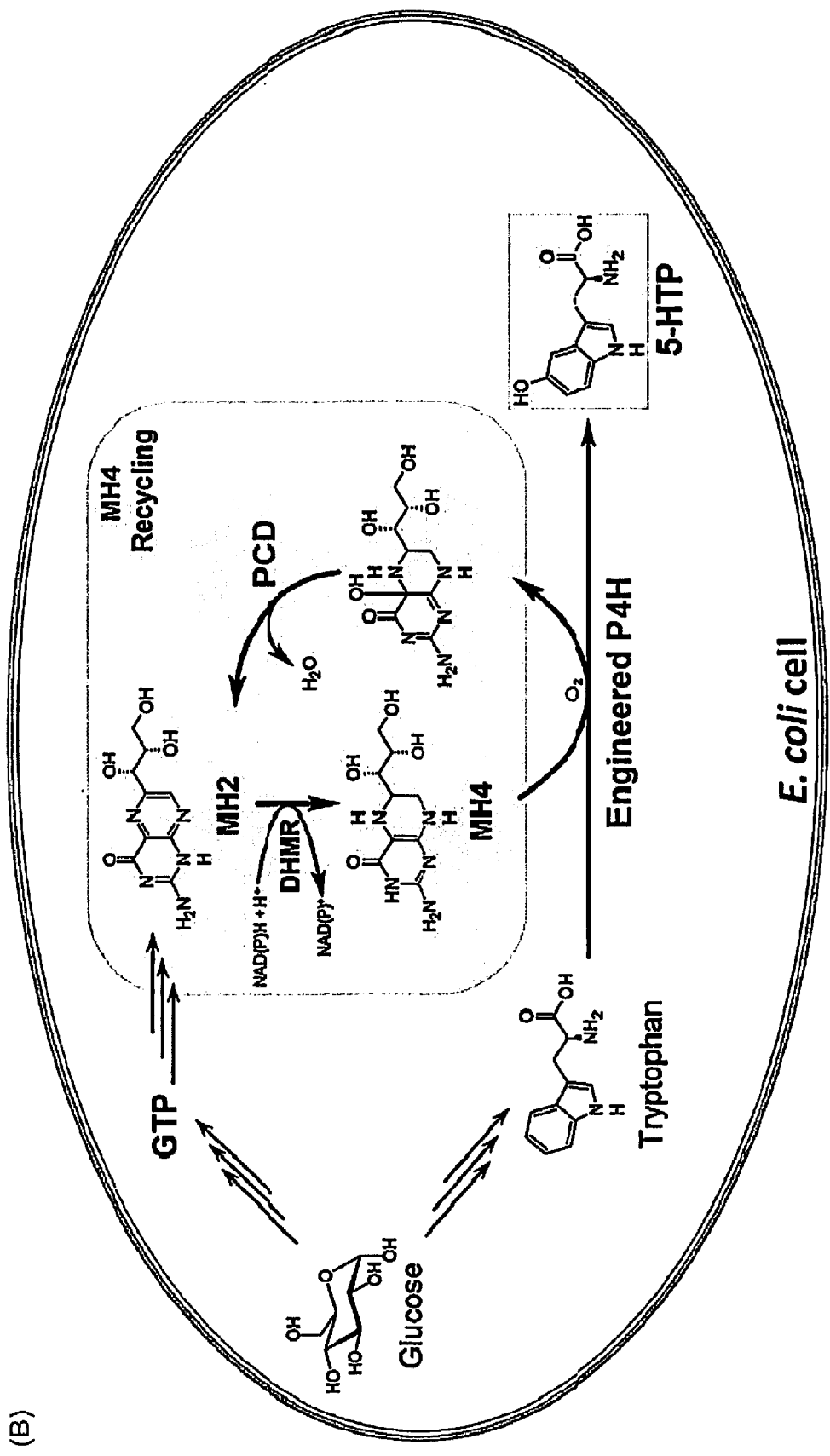

Before exploring the substrate-determining amino acid residues, we picked five P4Hs from different microorganisms (*P. aeruginosa, Pseudomonas putida, Pseudomonas fluorescence, Ralstonia eutropha* and *Xanthomonas campestris*) to verify and compare their activities and substrate preferences, since most of the prokaryotic P4Hs are still putative enzymes without experimental confirmation of their function. The P4H from *P. aeruginosa* (PaP4H) was previously identified in vitro and its crystal structure has been resolved[24]. Some genetic and biochemical evidence suggested that PaP4H utilizes MH4 instead of BH4 as the native pterin coenzyme[20]. Thus, we first selected it as a prototype to establish its in vivo activity in *E. coli*, since MH4 is the major pterin produced by *E. coli* (FIG. 2). To achieve the expression of PaP4H, its gene phhA was amplified from the genomic DNA of *P. aeruginosa* and cloned into a high-copy number plasmid under the control of an IPTG-inducible promoter $P_LlacO1$. The resulting expression vector pZE-PaphhA was introduced into *E. coli* strain BW25113ΔtnaA (abbreviated as BWΔtnaA). Since tryptophanase encoded by tnaA was reported to catalyze the degradation of tryptophan and 5-HTP[25], the gene was knocked out from all the strains used in this study. We observed that the cell growth of BWΔtnaA carrying pZE-PaphhA was significantly retarded. Its $OD_{600}$ values only reached 0.8-1.0 after 8-hour cultivation, dramatically lower than those of the control strain (BWΔtnaA carrying an empty vector) with $OD_{600}$ values at 5.5-6.0. A similar effect was also observed in a previous study[26]. When the cells were incubated with phenylalanine (500 mg l$^{-1}$), almost no hydroxylated product (tyrosine) was detected. Indeed, *P. aeruginosa* possesses a pterin 4a-carbinolamine dehydratase (PCD, encoded by phhB) responsible for the regeneration of dihydromonapterin (MH2) which can be further reduced to MH4. But *E. coli* does not have such a mechanism natively. To establish an artificial MH4 recycling system (FIG. 2), phhB from *P. aeruginosa* and folM from *E. coli* (encoding dihydromonapterin reductase, DHMR) were co-expressed along with the phhA using the vector pZE-PaABM. Interestingly, the *E. coli* strain harboring this vector dramatically improved cell viability which was comparable with the control strain. Its $OD_{600}$ values reached 4.5-5.5 after cultivation for 8 hours. When these cells were collected and incubated with phenylalanine, a large amount of tyrosine was produced at a rate of 83.50 $\mu M/h/OD_{600}$, as was shown in the in vivo assays (Table 1). These results indicated that introduction of the MH4 recycling system not only restored the cell growth but also enabled the *E. coli* strain to convert phenylalanine to tyrosine. Moreover, this strain was also capable of converting tryptophan into 5-HTP (Table 1), although the production rate (0.19 $\mu M/h/OD_{600}$) was much lower, only equivalent to 0.23% of that towards phenylalanine.

TABLE 1

In vivo activities of P4Hs from different microorganisms

| Source of P4H | In vivo activity[a] ($\mu M/h/OD_{600}$) | | Preference (Phe:Trp) |
|---|---|---|---|
| | Phenylalanine | Tryptophan | |
| *Pseudomonas aeruginosa* | 83.50 ± 16.00 | 0.19 ± 0.02 | 439.5 |
| *Pseudomonas putida* | 76.32 ± 10.02 | 0.12 ± 0.03 | 636.0 |
| *Pseudomonas fluorescence* | 82.47 ± 12.05 | 0.20 ± 0.05 | 412.4 |
| *Ralstonia eutropha* H16 | 73.33 ± 4.63 | 1.22 ± 0.04 | 60.1 |
| *Xanthomonas campestris* | 97.40 ± 4.42 | 2.91 ± 0.21 | 33.5 |

[a]All data are reported as mean ± s.d. from three independent experiments.

On this basis, another four P4Hs were also tested by replacing the PaP4H gene on pZE-PaABM with their respective genes. As shown in Table 1, all the identified P4Hs showed high activity and strong substrate preference towards phenylalanine in *E. coli*. Among them, the P4H from *X. campestris* (XcP4H) exhibited the highest activity towards both phenylalanine and tryptophan. The three from *pseudomonas* species showed the most similar catalytic properties, which is consistent with their close phylogenetic relationship. Therefore, we confirmed that all the tested P4Hs can function well by utilizing the *E. coli* endogenous pterin coenzyme MH4 in the presence of a recycling system.

Modification of the XcP4H Substrate Preference Through Protein Engineering.

Figure 3:
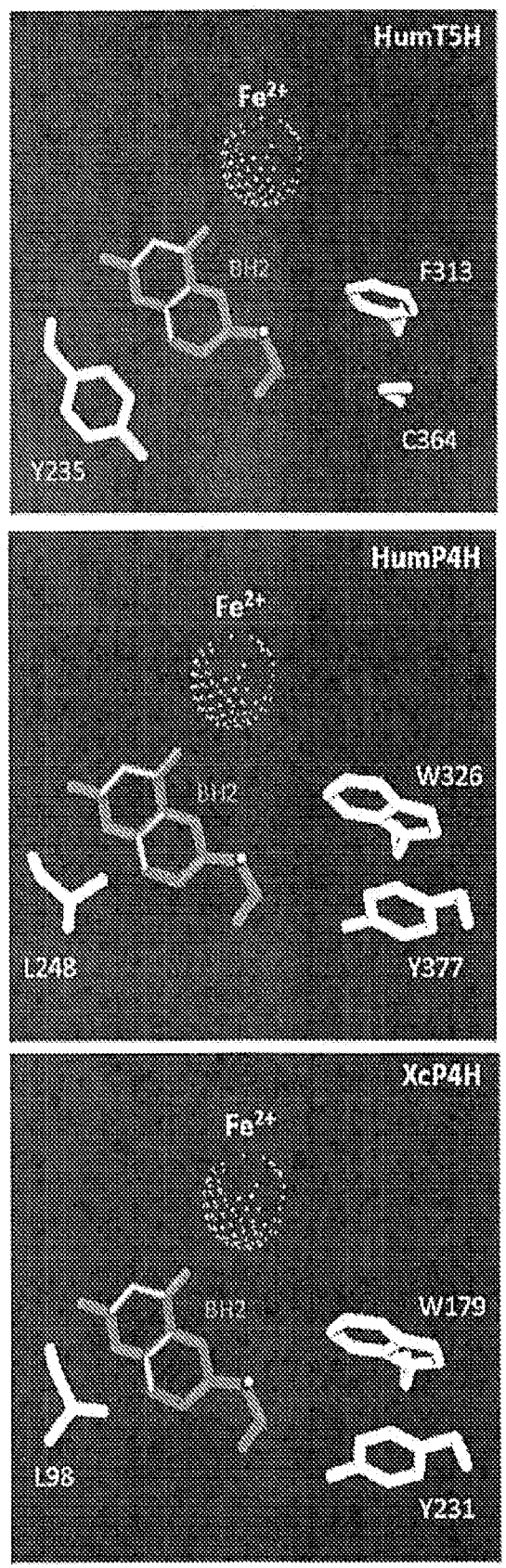
FIG. 3 shows modification of XcP4H via protein engineering; (A), comparative illustration of the positions of the 3 critical residues (L98, W179 and Y231) in the structures of XcP4H, the P4H from human (HumP4H; PDB entry 1MMK) and the T5H1 from human (HumT5H; PDB entry 3HF6); (B), in vivo activities of wild type XcP4H and its mutants, wherein grey- and black-colored bars indicate the activities towards tryptophan and phenylalanine, respectively; (C), whole-cell bioconversion of tryptophan into 5-HTP, wherein solid and dotted lines indicate the time courses of 5-HTP production and cell density, respectively, and black- and grey-colored lines indicate the profiles at 30 and 37° C., respectively, and wherein all data are reported as mean±s.d. from three independent experiments and error bars are defined as s.d.
Figure 3:
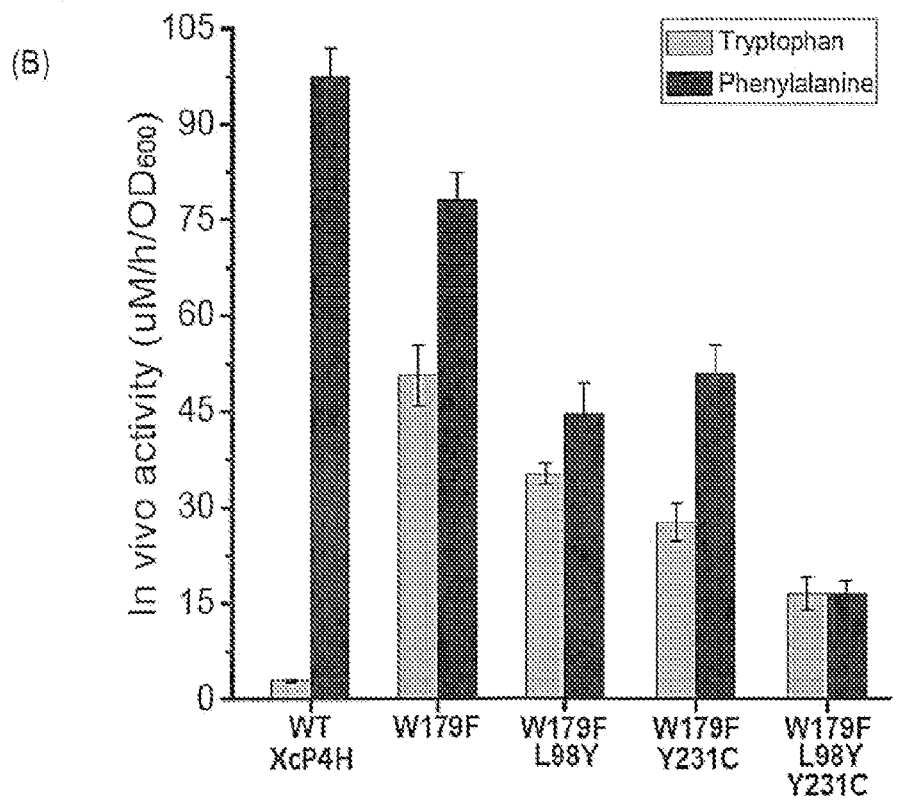
Figure 3:
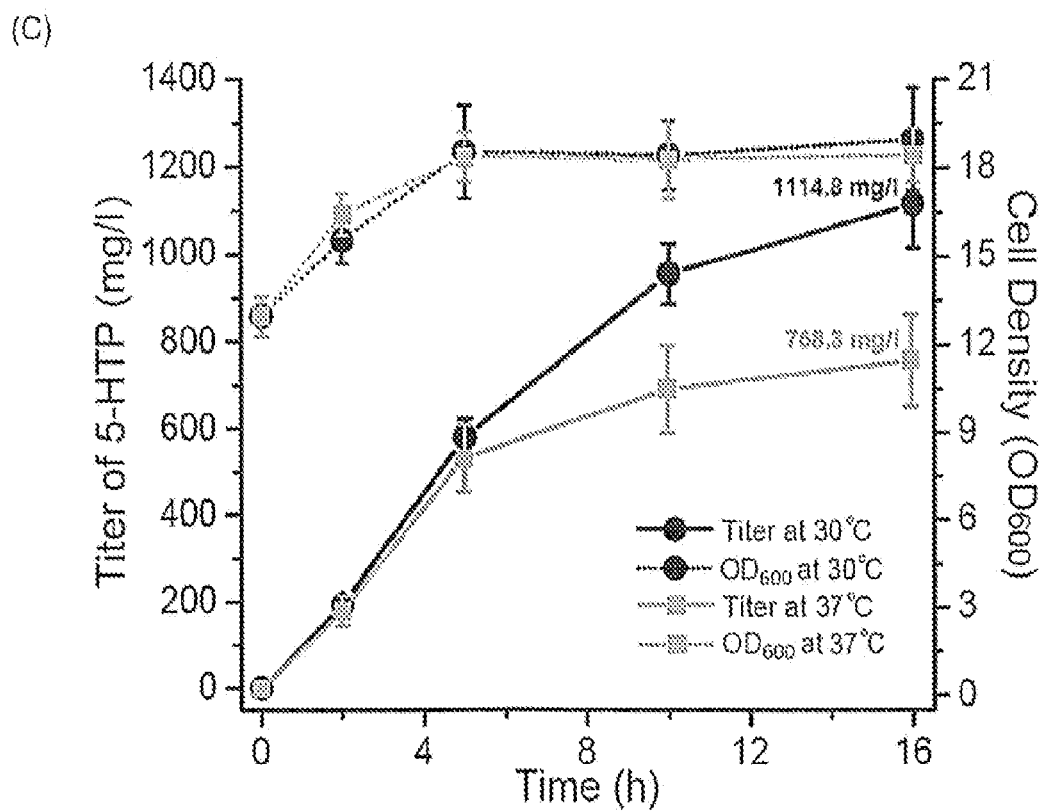

XcP4H was selected for protein engineering due to its superior catalytic potential. To investigate the substrate-determining amino acid residues, its sequence was aligned with animal P4Hs and T5Hs. Comparison of the sequences of only animal P4Hs and T5Hs led to the identification of a number of residues that are conserved within each group but varied between groups. However, when these residues were aligned with the XcP4H sequence, only six of them were found to be conserved in P4Hs and probably critical to the substrate selectivity, which are Q85, L98, W179, L223, Y231, and L282, numbered according to the numbering system for *X. campestris* (FIG. 5G, six arrows). To further investigate their locations in the enzyme structure, a homology model was built using the crystal structure of the P4H from *C. violaceum* (PDB code 3TK2) as a template. The conserved residues were well aligned with those in the crystal structures of the human P4H (PDB code 1MMK) and T5H1 (PDB code 3HF6), indicating the reliability of the model. In this structure, W179 is located inside the catalytic pocket just at the predicted phenylalanine binding site, while L98 and Y231 are near the entrance to the pocket, which are closer to the coenzyme MH4 binding site (FIG. 3A). However, Q85, L223 and L282 are not located near the catalytic pocket, suggesting these residues are less relevant to the enzyme's substrate selection. Therefore, we selected W179, L98 and Y231 as the targets for further mutation analysis. We hypothesized that if these residues were replaced with their respective residues in T5Hs that are F, Y and C, respectively, the mutants might exhibit stronger preference towards tryptophan. As a result, the W179F mutant of XcP4H exhibited a 17.4-fold increase in tryptophan hydroxylation activity compared with the wild-type (WT) enzyme; meanwhile its activity towards phenylalanine decreased by about 20%. The substrate preference towards phenylalanine over tryptophan was shifted from 33.5 to 1.5 (Table 2). When the mutations L98Y or Y231C were combined with W179F, the substrate preference further shifted towards tryptophan, although their activities towards tryptophan were not as high as that of W179F alone. The triple mutant showed almost the same preference towards the two substrates (FIG. 3B). As mentioned, L98 and Y231 are closer to the MH4 binding site, suggesting that these two residues might not contribute to the aromatic amino acid substrate selection.

TABLE 2

In vivo activities and substrate preferences of XcP4H mutants

| XcP4H mutants | Substrate | | | | Preference (Phe:Trp) |
|---|---|---|---|---|---|
| | Phenylalanine | | Tryptophan | | |
| | In vivo activity[b] ($\mu M/h/OD_{600}$) | R.A.[a] (%) | In vivo activity ($\mu M/h/OD_{600}$) | R.A. (%) | |
| WT | 97.40 ± 4.42 | 100 | 2.91 ± 0.21 | 100 | 33.5 |
| W179F | 78.05 ± 4.34 | 80 | 50.60 ± 4.72 | 1739 | 1.5 |
| W179F/L98Y | 44.49 ± 4.95 | 46 | 35.13 ± 1.67 | 1207 | 1.3 |
| W179F/Y231C | 50.92 ± 4.36 | 52 | 27.71 ± 2.99 | 952 | 1.8 |
| W179F/L98Y/Y231C | 16.56 ± 1.86 | 17 | 16.58 ± 2.59 | 570 | 1.0 |

[a]R.A., relative activity, setting the R.A. of WT XcP4H as 100%
[b]All data are reported as mean ± s.d. from three independent experiments.

To further explore the potential of XcP4H mutant W179F for whole-cell biocatalysis, feeding experiments were conducted by incubating pre-cultured E. coli cells harboring pZE-XcABMW179F (initial $OD_{600}$=12-13) with 2.0 g $l^{-1}$ of tryptophan. As shown in FIG. 3C, the initial conversion rates were similar at 30 and 37° C., although the cells grew slightly faster at 37° C. However, the production efficiency at 30° C. became obviously higher after 5 hours. By the end of 16 hours, the cultures at 30 and 37° C. accumulated 1114.8 and 758.3 mg $l^{-1}$ of 5-HTP at the expense of 1503.2 and 1417.1 mg $l^{-1}$ tryptophan, respectively. Meanwhile, we observed that the color of the cultures gradually turned dark after 5 hours, especially at 37° C., probably due to the oxidation of 5-HTP and tryptophan under aerobic conditions.

De Novo Microbial Synthesis of 5-HTP Via Metabolic Engineering.

Figure 4:
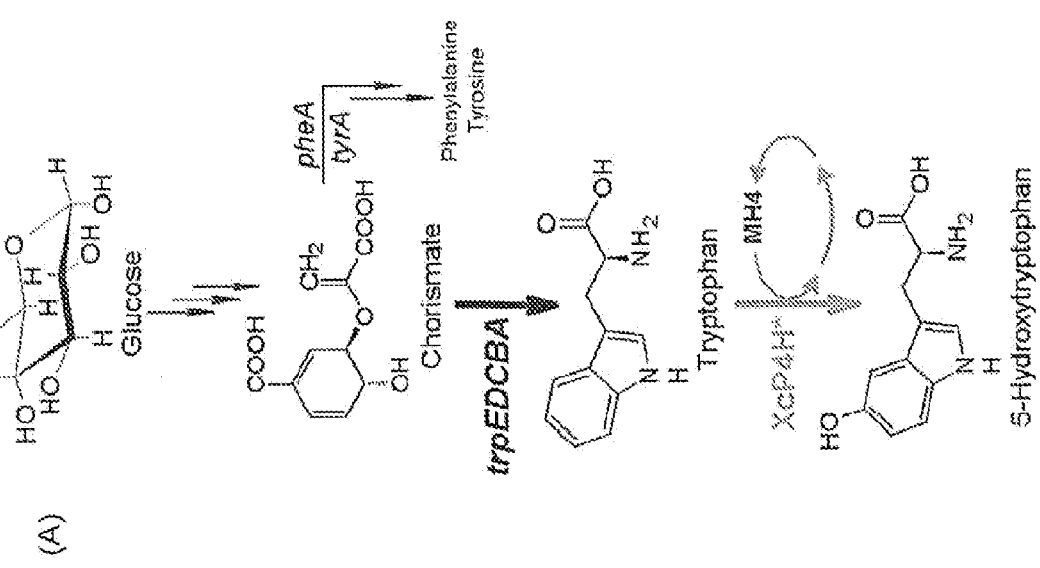
FIG. 4 shows de novo production of 5-HTP from glucose; (A), schematic presentation of the complete 5-HTP biosynthetic pathway wherein the black- and grey-colored arrows indicate the *E. coli* native pathways and heterologous reactions, respectively; (B), production of tryptophan from glucose at 30 and 37° C., wherein data are reported as mean±s.d. from two independent experiments; (C), profiles of cell growth and 5-HTP production from glucose of two host strains BWΔtnaA (grey) and QH4ΔtnaA (black), wherein all data are reported as mean±s.d. from three independent experiments and error bars are defined as s.d.
Figure 4:
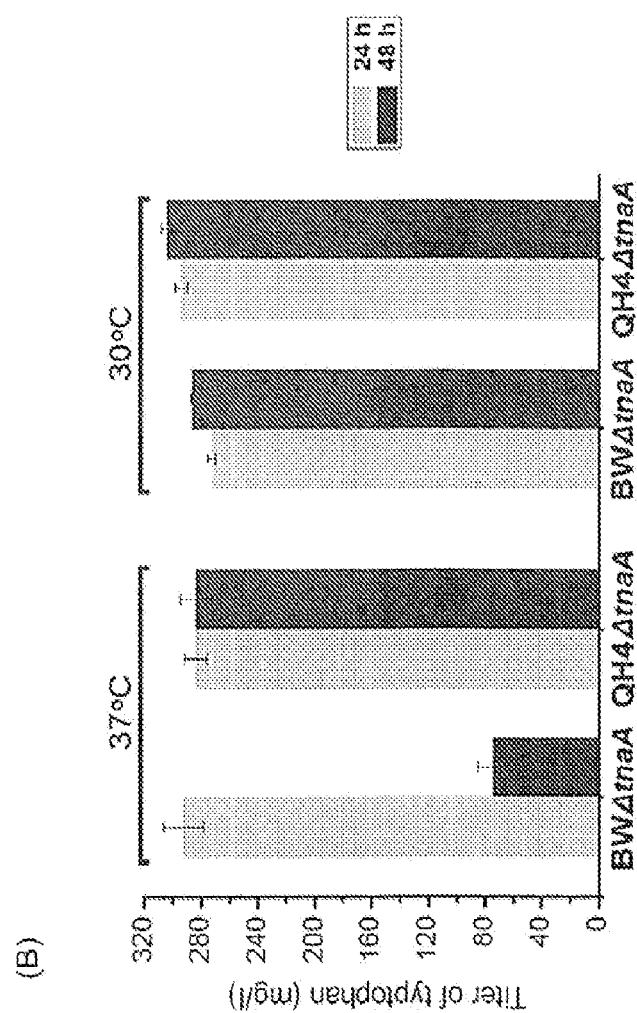
Figure 4:
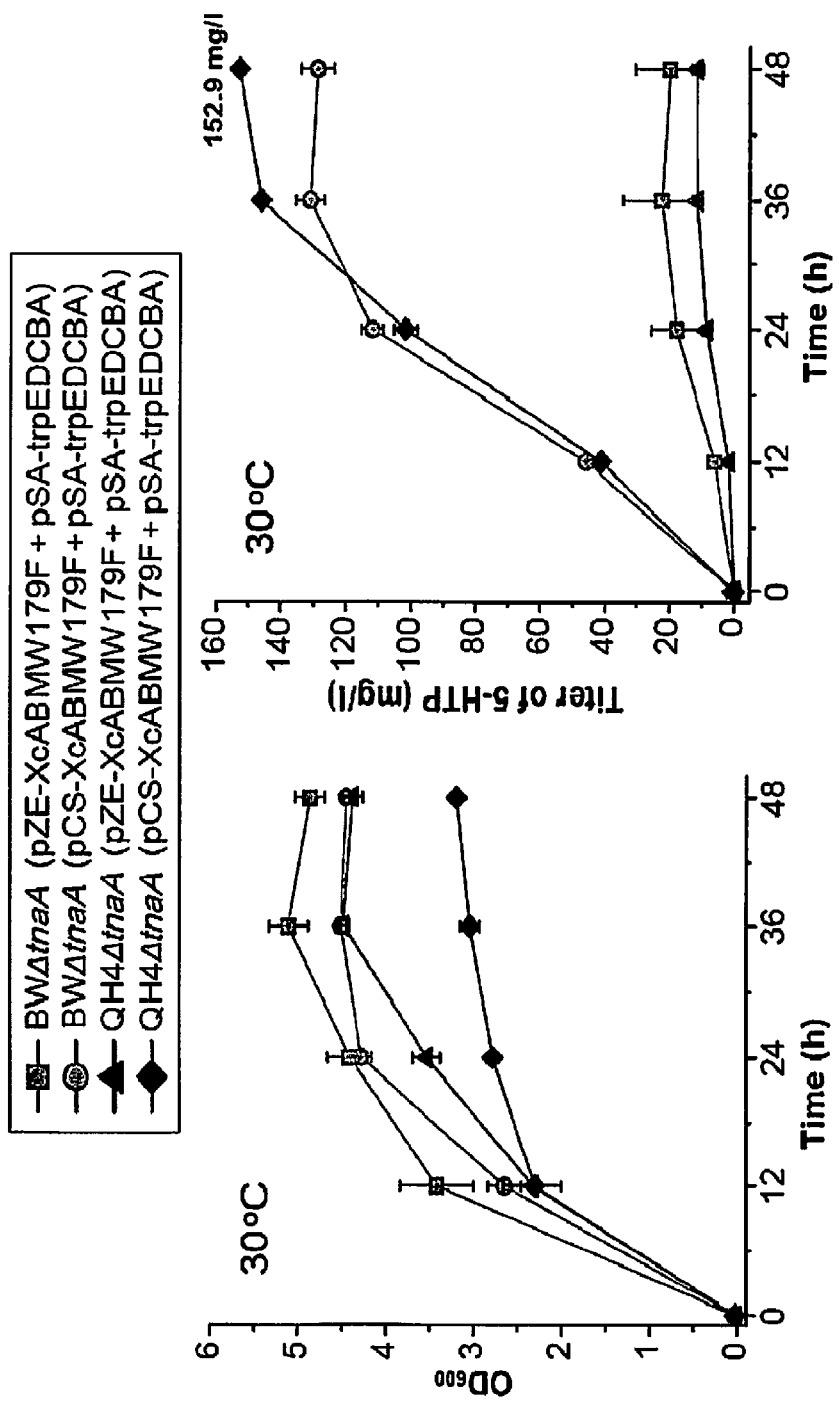

After achieving the efficient bioconversion of tryptophan to 5-HTP, we proceeded with the construction of a 5-HTP producing strain which allows the utilization of endogenous tryptophan generated from simple carbon sources (FIG. 4A). Our first attempt was focused on the construction of a tryptophan overproducer. In E. coli, tryptophan biosynthesis is branched from the shikimate pathway at chorismate by the action of the trp regulon (FIG. 4A) and negatively regulated by tryptophan transcriptional repressor (TrpR) in response to intracellular tryptophan levels. To circumvent the intrinsic regulation at the transcription level, the complete trp operon including trpEDCBA was cloned into a low-copy plasmid under the control of an IPTG inducible promoter. Meanwhile, to eliminate the feed-back inhibition effect, a mutation S40F was incorporated into TrpE according to a previous study[27], resulting in plasmid pSA-TrpEDCBA. When the plasmid was introduced into E. coli BWΔtnaA, the resulting strain produced 292.2 mg $l^{-1}$ of tryptophan at 37° C. after 24-hour cultivation; however, the titers dramatically decreased after 48 h (74.4 mg $l^{-1}$) probably due to oxidative degradation[28]. This problem was solved when the growth temperature was changed to 30° C. (FIG. 4B). In addition to BWΔtnaA, we also attempted to use QH4ΔtnaA as the host for boosting carbon flux through the shikimate pathway, because QH4 is a derivative of the well-developed phenylalanine overproducer ATCC31884 with pheLA and tyrA disrupted and has been successfully engineered for the enhanced production of caffeic acid, salicylic acid and muconic acid in our previous studies[29,30]. However, in this study, QH4ΔtnaA harboring pSA-TrpEDCBA did not significantly improve the production of tryptophan but showed slightly improved titers at 30° C. compared with the BWΔtnaA host. By the end of 48 h, up to 304.4 mg $l^{-1}$ of tryptophan was produced (FIG. 4B). The control strain QH4ΔtnaA without the over-expression of the trp operon did not accumulate tryptophan at either temperature.

As the tryptophan production and the bioconversion of tryptophan to 5-HTP were achieved and 30° C. worked better for both cases, our further efforts were directed to the establishment of de novo biosynthesis of 5-HTP at this temperature by integrating the two modules. When pZE-XcABMW179F was co-transferred together with pSA-TrpEDCBA into E. coli BWΔtnaA and QH4ΔtnaA, the generated strains only produced 19.9 and 11.5 mg $l^{-1}$ of 5-HTP, respectively, without accumulating tryptophan in the cultures. Apparently, the introduction of the 5-hydroxylation reaction using a high-copy number plasmid exerted negative influence on the carbon flow through tryptophan compared with their parent strains. We speculated that the excessive expression of the XcP4H mutant with the MH4 recycling system might have resulted in metabolic imbalance and disturbed carbon flux towards tryptophan. To test this hypothesis, we cloned the coding sequences of XcP4H mutant W179F, PCD and DHMR into a medium-copy-number plasmid instead of the high-copy-number one, yielding plasmid pCS-XcABMW179F. Interestingly, we observed dramatic improvement on 5-HTP production for both BWΔtnaA and QH4ΔtnaA harboring pCS-XcABMW179F; by the end of 48 hours, the two strains produced 128.6 and 152.9 mg $l^{-1}$ of 5-HTP, respectively (FIG. 4C), at the expense of 8.5 and 9.7 g $l^{-1}$ of glucose consumption, respectively. Meanwhile, we detected the accumulation of tryptophan at the concentrations of 166.3 and 339.7 mg $l^{-1}$ for the two strains, indicating that the carbon flux towards tryptophan was fully recovered. Other by-products were also detected as depicted in Table 3. The 5-HTP producing strains followed growth-dependent production patterns (FIG. 4C).

TABLE 3

Intermediates and by-products produced by 5-HTP producing strains

| Host strain[a] | Biomass ($OD_{600}$) | Tyrosine (mg/L) | Tryptophan (mg/L) | Acetate (g/L) | Pyruvate (g/L) |
| --- | --- | --- | --- | --- | --- |
| $BW_{\Delta tnaA}$ | 4.44 ± 0.02 | 52.30 ± 0.36 | 166.29 ± 1.52 | 2.72 ± 0.00 | 1.41 ± 0.06 |
| $QH4_{\Delta tnaA}$ | 3.19 ± 0.05 | 34.85 ± 3.34 | 339.68 ± 18.15 | 1.55 ± 0.22 | 2.11 ± 0.27 |

[a]Both host strains containing plasmid pSA-TrpEDCBA and pCS-XcABMW179F.
[b]All data are reported as mean ± s.d. from 3 independent experiments. Error bars are defined as s.d.

Discussion.

The high price of medication has become a major burden of families over the world. High price indeed deprives the low-income population of access to the use of some drugs that are hard to obtain and expensive. The causes of this issue are either the low efficiency in isolating these pharmaceuticals from natural sources or the high cost for their chemical synthesis. Microbial biosynthesis and biocatalysis provide a facile and eco-friendly way for the production of pharmaceutically valuable compounds. The development of metabolic engineering and synthetic biology tools enables tailored assembly of heterologous and artificial pathways in desirable host strains for the biosynthesis of target products[31].

Lack of suitable enzymes is one of the most frequently encountered problems in pathway engineering in microbes. Functional expression of eukaryotic enzymes is often problematic due to their low solubility, low stability and/or requirements for post-translational modification. For example, the tryptophan 5-hydroxylation reaction has been understood for a long time and many T5Hs has been identified and characterized from human and animals. However, animal AAAHs were hard to be expressed in *E. coli* in a soluble and stable form[14,32]. In addition, their activities are usually regulated by phosphorylation as well as their products[33]. Although the use of truncated or fusion proteins can help obtain soluble and active enzymes[32], the catalytic efficiency seems still low in the production of 5-HTP in *E. coli* using truncated animal T5Hs[16]. In recent years, protein engineering has become a potent tool for enzyme modification in order to obtain desired catalytic properties[34]. In our study, a highly active P4H that utilizes MH4 was successfully engineered to catalyze the tryptophan 5-hydroxylation reaction. Another group recently reported 5-HTP production in *E. coli* with a mutant P4H from *C. violaceum*[35]. However, its function had to completely rely on the supplementation of exogenous pterin coenzyme 6,7-dimethyl-5,6,7,8-tetrahydropterine hydrochloride[35], which is disadvantageous in terms of economic viability.

Self-supply or regeneration of cofactors (including coenzymes and co-substrates) is one of the greatest advantages for whole-cell biosynthesis and biocatalysis. In *E. coli* host, many of such molecules can be natively generated along with cell growth, such as $FMN/FMNH_2$, $FAD/FADH_2$, $NAD(P)^+/NAD(P)H$, coenzyme A, acetyl-CoA, malonyl-CoA, MH4, etc. Although it is more convenient and economical to utilize these endogenous cofactors, sometimes heterologous enzymes require the cofactor(s) not produced by the host strain. To solve such a problem, one approach is to supplement exogenous cofactors into the culture medium. But it should be noted that most of the cofactors such as tetrahydropterine are so expensive that the supplementation of them is not economically viable for commercial production. Another approach is to introduce the cofactor biosynthetic and/or regeneration mechanism(s) into the host strain. As in the study using animal T5H to produce 5-HTP, a BH4 biosynthetic pathway starting from GTP was introduced into *E. coli*[16]. Meanwhile, a BH4 regeneration system was necessary to achieve continuous production. Recently, an interesting study reported that the mouse T3H can also utilize *E. coli* MH4 in the presence of a BH4 regeneration system, although the efficiency was proved to be low[36]. In this work, with minimal modifications of the host strains' metabolism, the prokaryotic P4Hs and the mutants were able to utilize and recycle *E. coli* endogenous MH4 and NAD(P)H (FIGS. 2A and B).

Conclusion.

This work simultaneously solved two problems in the biological production of 5-HTP, which are related to enzyme compatibility and cofactor self-supply. To our knowledge, the titer of 5-HTP (1.1-1.2 g $l^{-1}$) generated from tryptophan in this work is significantly higher than those in previous studies, showing great scale-up potential. Moreover, this work also demonstrates the de novo production of 5-HTP without needing to supplement precursors and coenzymes. Since the high-level production of tryptophan (up to 48.7 g $l^{-1}$) has already been achieved in *E. coli*[37], introduction and optimization of the 5-hydroxylation reaction into tryptophan overproducers is expected to result in efficient and low-cost production of 5-HTP.

Materials and Methods

Experimental Materials.

*E. coli* XL1-Blue was employed as the host strain for cloning and plasmid propagation; *E. coli* BW25113ΔtnaA was used as the host strain for in vivo enzyme assays, feeding experiments, and de novo production of tryptophan and 5-HTP. QH4 was previously constructed with the disruption of pheLA and tyrA from a phenylalanine producer *E. coli* ATCC31884[29]. Luria-Bertani (LB) medium containing 10 g $l^{-1}$ tryptone, 5 g $l^{-1}$ yeast extract, and 10 g $l^{-1}$ NaCl was used for cell cultivation and enzyme expression. M9 minimal medium containing 5 g $l^{-1}$ glycerol, 6 g $l^{-1}$ $Na_2HPO_4$, 0.5 g $l^{-1}$ NaCl, 3 g $l^{-1}$ $KH_2PO_4$, 1 g $l^{-1}$ $NH_4Cl$, 246.5 mg $l^{-1}$ $MgSO_4.7H_2O$, 14.7 mg $l^{-1}$ $CaCl_2$ and 27.8 mg $l^{-1}$ $FeSO_4.7H_2O$, was used for in vivo assays of P4Hs. Modified M9 (M9Y) medium was used for de novo production of tryptophan and 5-HTP. M9Y medium contains 10 g $l^{-1}$ glucose, 6 g $l^{-1}$ $Na_2HPO4$, 0.5 g $l^{-1}$ NaCl, 3 g $l^{-1}$ $KH_2PO_4$, 1 g $l^{-1}$ $NH_4Cl$, 246.5 mg $l^{-1}$ $MgSO_4.7H_2O$, 14.7 mg $l^{-1}$ $CaCl_2.2H_2O$, 27.8 mg $l^{-1}$ $FeSO_4.7H_2O$, 2 g $l^{-1}$ yeast extract and 2 g $l^{-1}$ sodium citrate dihydrate. When necessary, kanamycin, ampicillin and/or chloramphenicol were supplemented to the media at the final concentration of 50, 100 and 34 mgl$^{-1}$, respectively. pZE12-luc, pCS27, pSA74 are high-, medium- and low-copy number plasmids[30], respectively, which were used for expressing enzymes in *E. coli*. Details of the strains and plasmids used in this study are depicted in Table 4.

TABLE 4

Strains and plasmids used in this study

| Strain | Genotype | Source |
| --- | --- | --- |
| XL1-Blue | recA1 endA1 gyrA96 thi-1 hsdR17 supE44 relA1 lac [F' proAB lacI$^q$ZΔM15 Tn10 (Tet$^r$)] | Stratagene |
| JW3686-7 | F–, Δ(araD-araB)567, ΔlacZ4787(::rrnB-3), λ-, rph-1, ΔtnaA739::kan, Δ(rhaD-rhaB)568, hsdR514 | CGSC |
| QH4 | *E. coli* ATCC31884 with pheLA and tyrA disrupted | (28) |
| BW25113ΔtnaA | JW3686-7 with kan deleted | This study |
| QH4 | QH4 with tnaA deleted | This study |

| Plasmids | Description | Reference |
| --- | --- | --- |
| pZE12-luc | $P_L$lacO1, colE ori, luc, Amp$^r$ | (29) |
| pCS27 | $P_L$lacO1, P15A ori, Kan$^r$ | (29) |
| pSA74 | $P_L$lacO1, pSC101 ori, Cm$^r$ | (29) |
| pZE-PaphhA | pZE12-luc containing phhA from *P. aeruginosa* PAO1 | This study |
| pZE-PaABM | pZE12-luc containing phhA andn phhB from *P. aeruginosa* PAO1, and folM from *E. coli* MG1655 | This study |
| pZE-PfABM | pZE12-luc containing phhA from *P. fluorescens* Migula, phhB from *P. aeruginosa* PAO1, and folM from *E. coli* MG1655 | This study |

TABLE 4-continued

Strains and plasmids used in this study

| | | |
|---|---|---|
| pZE-PpABM | pZE12-luc containing phhA from *P. putida* KT244Q, phhB from *P. aeruginosa* PAO1, and folM from *E. coli* MG1655 | This study |
| pZE-ReABM | pZE12-luc containing phhA folM from *R. eutropha* H16, phhB from *P. aeruginosa* PAO1, and folM from *E. coli* MG1655 | This study |
| pZE-XcABM | pZE12-luc containing phhA from *X. campestris* ATCC 33913, phhB from *P. aeruginosa* PAO1, and folM from *E. coli* MG1655 | This study |
| pZE-XcABMW179F | pZE-XcABM with mutation W179F on the P4H | This study |
| pSA-XcABM2Ma | pZE-XcABM with mutations W179F and L98Y on the P4H | This study |
| pZE-XcABM2Mb | pZE-XcABM with mutations W179F and Y231C on the P4H | This study |
| pZE-XcABM3M | pZE-XcABM with mutations W179F, L98Y and Y231C on the P4H | This study |
| pCS-XcABMW179F | pCS27 containing phhA (W179F) from *X campestris* ATCC 33913, phhB from *P. aeruginosa* PAO1, and folM from *E. coli* MG1655 | This study |
| pSA-TrpEDCBA | pSA74 containing trpEDCBA with S40F on TrpE | This study |

DNA Manipulation.

*E. coli* strain BW25113 ΔtnaA::kan (JW3686-7) was purchased from Coli Genetic Stock Center (CGSC). The kanamycin resistant marker was deleted according to the reported protocol[38]. Deletion of the tnaA gene from QH4 was performed using the reported Red disruption method[38]. Plasmid pZE-PaphhA was constructed by inserting the amplified phhA gene from *Pseudomonas aeruginosa* into pZE12-luc using restriction sites Acc65I and XbaI. pZE-PaABM was constructed by inserting phhA and phhB from *P. aeruginosa* and folM from *E. coli* into pZE12-luc via multi-piece ligation using Acc65I/NdeI, NdeI/HindIII and HindIII/XbaI. pZE-PpABM, pZE-PfABM, pZE-ReABM and pZE-XcABM were constructed using the same approach with the respective phhA genes in place of the phhA gene from *P. aeruginosa*. pSA-trpEDCBA was constructed by inserting the DNA fragment of trpEDCBA from *E. coli* into pSA74 using Acc65I and BamHI. Site-directed mutagenesis was conducted by overlap PCR. Plasmids pZE-XcABMW179F, pZE-XcABM2Ma, pZE-XcABM2 Mb, pZE-XcABM3M were constructed by replacing the wild type phhA gene from *X. campestris* with the respective mutant genes (Table 4)

Construction of Phylogenetic Tree and Homology Modeling.

The AAAH sequences were randomly selected from GenBank using "phenylalanine 4-hydroxylase", "tyrosine 3-hydroxylase" and "tryptophan 5-hydroxylase" as the searching keywords. The alignment of the AAAH amino acid sequences was conducted by using ClustalX 2.1. The phylogenetic tree was constructed by Molecular Evolutionary Genetics Analysis (MEGA) version 5.02 using the neighbor joining method[22]. Bootstrapping test was performed to evaluate the reliability (1000 replicates). All other used parameters were the default of the software. The homology model of XcP4H was built with the SWISS-MODEL online server by using the crystal structure of the P4H from *C. violaceum* (PDB code 3TK2) as a template.

In Vivo Assays of Wild-Type and Mutant P4Hs.

*E. coli* BW25113ΔtnaA carrying pZE-PaABM was inoculated in 50 ml of LB liquid medium containing 0.5 mM of IPTG and 100 µgml$^{-1}$ of ampicillin, and grown aerobically at 37° C. for about 8 h till OD$_{600}$ reached 4.5-5.5. Then the cells were harvested, and re-suspended in the M9 minimal medium (OD$_{600}$=4.5-5.5). After adaption for 20 min, phenylalanine or tryptophan was added into the cell suspension to a final concentration of 500 mg l$^{-1}$. At the same time, 1 mM of ascorbic acid was added to avoid the product oxidation. The flasks were incubated with shaking (300 rpm) at 37° C. for 1 h. Subsequently, samples were taken by removing cell pellets and the products (tyrosine and tryptophan) were quantitatively measured with HPLC. The same method was used to measure the in vivo activities of other P4Hs and XcP4H mutants. The in vivo activities of P4Hs were expressed as µM/min/OD$_{600}$.

Bioconversion of Tryptophan to 5-HTP.

*E. coli* strain BW25113ΔtnaA was transformed with plasmid pZE-XcABMW179F. Single colonies were inoculated into 50 ml LB medium containing 0.5 mM of IPTG and grown aerobically at 37° C. for about 8 h till OD$_{600}$ reached around 5.0. Then cells were harvested, re-suspended in 20 ml of M9Y medium (at OD$_{600}$=12-13) containing 2 g l$^{-1}$ of tryptophan and left to grow at 30 and 37° C. Samples were taken at 2 h, 5 h, 10 h and 16 h. The concentrations of produced 5-HTP were analyzed by HPLC.

De Novo Production of Tryptophan and 5-HTP.

Overnight LB cultures of the producing strains were inoculated at 2% into the M9Y medium containing appropriated antibiotics and cultivated at 30 and 37° C. with shaking at 300 rpm. IPTG was added to the cultures to a final concentration of 0.5 mM at 0 h. Samples were taken every 12 hours. The OD$_{600}$ values were measured and the concentrations of the products, intermediates and by-products were analyzed by HPLC.

HPLC Analysis.

L-tyrosine (from SIGMA ALDRICH), L-tryptophan (from SIGMA ALDRICH) and 5-HTP (from Acros Organics) were used as standards. Both the standards and samples were quantified by HPLC (Dionex Ultimate 3000 installed with an Ultimate 3000 Photodiode Array Detector and a reverse phase ZORBAX SB-C18 column). A gradient elution method was used according to our previous study[39]. Quantification of tryptophan, tyrosine and 5-HTP was based on the peak areas at specific wavelength (276 nm). Glucose, acetate and pyruvate were quantified using a previously described method[40].

REFERENCES

1. WHO. (2012) World Health Organization Fact Sheet on Depression, http://www.who.int/mediacentre/factsheets/fs369/en/index.html.

2. Byerley, W. F., Judd, L. L., Reimherr, F. W., and Grosser, B. I. (1987) 5-Hydroxytryptophan: a review of its antidepressant efficacy and adverse effects, *J. Clin. Psychopharmacol.* 7, 127-137.
3. Turner, E. H., Loftis, J. M., and Blackwell, A. D. (2006) Serotonin a la carte: supplementation with the serotonin precursor 5-hydroxytryptophan, *Pharmacol. Ther.* 109, 325-338.
4. Birdsall, T. C. (1998) 5-Hydroxytryptophan: a clinically-effective serotonin precursor, *Altern. Med. Rev.* 3, 271-280.
5. Ajikumar, P. K., Xiao, W. H., Tyo, K. E. J., Wang, Y., Simeon, F., Leonard, E., Mucha, O., Phon, T. H., Pfeifer, B., and Stephanopoulos, G. (2010) Isoprenoid Pathway Optimization for Taxol Precursor Overproduction in *Escherichia coli*, *Science* 330, 70-74.
6. Leonard, E., Ajikumar, P. K., Thayer, K., Xiao, W. H., Mo, J. D., Tidor, B., Stephanopoulos, G., and Prather, K. L. J. (2010) Combining metabolic and protein engineering of a terpenoid biosynthetic pathway for overproduction and selectivity control, *Proc. Natl. Acad. Sci. U.S.A.* 107, 13654-13659.
7. Anthony, J. R., Anthony, L. C., Nowroozi, F., Kwon, G., Newman, J. D., and Keasling, J. D. (2009) Optimization of the mevalonate-based isoprenoid biosynthetic pathway in *Escherichia coli* for production of the anti-malarial drug precursor amorpha-4,11-diene, *Metab. Eng.* 11, 13-19.
8. Ro, D. K., Paradise, E. M., Ouellet, M., Fisher, K. J., Newman, K. L., Ndungu, J. M., Ho, K. A., Eachus, R. A., Ham, T. S., Kirby, J., Chang, M. C., Withers, S. T., Shiba, Y., Sarpong, R., and Keasling, J. D. (2006) Production of the antimalarial drug precursor artemisinic acid in engineered yeast, *Nature* 440, 940-943.
9. Zhang, K., Li, H., Cho, K. M., and Liao, J. C. (2010) Expanding metabolism for total biosynthesis of the nonnatural amino acid L-homoalanine, *Proc. Natl. Acad. Sci. U.S.A.* 107, 6234-6239.
10. Lim, C. G., Fowler, Z. L., Hueller, T., Schaffer, S., and Koffas, M. A. G. (2011) High-Yield Resveratrol Production in Engineered *Escherichia coli*, *Appl. Environ. Microbiol.* 77, 3451-3460.
11. Lin, Y., Shen, X., Yuan, Q., and Yan, Y. (2013) Microbial biosynthesis of the anticoagulant precursor 4-hydroxycoumarin, *Nat. Commun.* 4, 2603.
12. Teigen, K., McKinney, J. A., Haavik, J., and Martinez, A. (2007) Selectivity and affinity determinants for ligand binding to the aromatic amino acid hydroxylases, *Curr. Med. Chem.* 14, 455-467.
13. Fitzpatrick, P. F. (2003) Mechanism of aromatic amino acid hydroxylation, *Biochemistry (Mosc.)* 42, 14083-14091.
14. McKinney, J., Knappskog, P. M., Pereira, J., Ekern, T., Toska, K., Kuitert, B. B., Levine, D., Gronenborn, A. M., Martinez, A., and Haavik, J. (2004) Expression and purification of human tryptophan hydroxylase from *Escherichia coli* and *Pichia pastoris*, *Protein Expr. Purif.* 33, 185-194.
15. Martinez, A., Knappskog, P. M., and Haavik, J. (2001) A structural approach into human tryptophan hydroxylase and its implications for the regulation of serotonin biosynthesis, *Curr. Med. Chem.* 8, 1077-1091.
16. Knight, E. M., Zhu, J., Förster, J., and Luo, H. (2013) Microorganisms for the production of 5-hydroxytryptophan; Int'l. Pat. Pub. WO2013/127914 A1, Jun. 9, 2013, Microorganisms for the production of 5-hydroxytryptophan.
17. Nakata, H., Yamauchi, T., and Fujisawa, H. (1979) Phenylalanine hydroxylase from *Chromobacterium violaceum*. Purification and characterization, *J. Biol. Chem.* 254, 1829-1833.
18. Zhao, G., Xia, T., Song, J., and Jensen, R. A. (1994) *Pseudomonas aeruginosa* possesses homologues of mammalian phenylalanine hydroxylase and 4 alpha-carbinolamine dehydratase/DCoH as part of a three-component gene cluster, *Proc. Natl. Acad. Sci. U.S.A.* 91, 1366-1370.
19. Kino, K., Hara, R., and Nozawa, A. (2009) Enhancement of L-tryptophan 5-hydroxylation activity by structure-based modification of L-phenylalanine 4-hydroxylase from *Chromobacterium violaceum*, *Journal of bioscience and bioengineering* 108, 184-189.
20. Pribat, A., Blaby, I. K., Lara-Nunez, A., Gregory, J. F., 3rd, de Crecy-Lagard, V., and Hanson, A. D. (2010) FolX and FolM are essential for tetrahydromonapterin synthesis in *Escherichia coli* and *Pseudomonas aeruginosa*, *J. Bacteriol.* 192, 475-482.
21. Erlandsen, H., Kim, J. Y., Patch, M. G., Han, A., Volner, A., Abu-Omar, M. M., and Stevens, R. C. (2002) Structural comparison of bacterial and human iron-dependent phenylalanine hydroxylases: similar fold, different stability and reaction rates, *J. Mol. Biol.* 320, 645-661.
22. Tamura, K., Peterson, D., Peterson, N., Stecher, G., Nei, M., and Kumar, S. (2011) MEGA5: molecular evolutionary genetics analysis using maximum likelihood, evolutionary distance, and maximum parsimony methods, *Mol. Biol. Evol.* 28, 2731-2739.
23. Cao, J., Shi, F., Liu, X., Huang, G., and Zhou, M. (2010) Phylogenetic analysis and evolution of aromatic amino acid hydroxylase, *FEBS Lett.* 584, 4775-4782.
24. Ekstrom, F., Stier, G., Eaton, J. T., and Sauer, U. H. (2003) Crystallization and X-ray analysis of a bacterial non-haem iron-containing phenylalanine hydroxylase from the Gram-negative opportunistic pathogen *Pseudomonas aeruginosa*, *Acta Crystallogr. D Biol. Crystallogr.* 59, 1310-1312.
25. Gong, F., Ito, K., Nakamura, Y., and Yanofsky, C. (2001) The mechanism of tryptophan induction of tryptophanase operon expression: tryptophan inhibits release factor-mediated cleavage of TnaC-peptidyl-tRNA(Pro), *Proc. Natl. Acad. Sci. U.S.A.* 98, 8997-9001.
26. Song, J., Xia, T., and Jensen, R. A. (1999) PhhB, a *Pseudomonas aeruginosa* homolog of mammalian pterin 4a-carbinolamine dehydratase/DCoH, does not regulate expression of phenylalanine hydroxylase at the transcriptional level, *J. Bacteriol.* 181, 2789-2796.
27. Zhao, Z. J., Zou, C., Zhu, Y. X., Dai, J., Chen, S., Wu, D., Wu, J., and Chen, J. (2011) Development of L-tryptophan production strains by defined genetic modification in *Escherichia coli*, *J. Ind. Microbiol. Biotechnol.* 38, 1921-1929.
28. Simat, T. J., and Steinhart, H. (1998) Oxidation of Free Tryptophan and Tryptophan Residues in Peptides and Proteins, *J. Agric. Food Chem.* 46, 490-498.
29. Huang, Q., Lin, Y., and Yan, Y. (2013) Caffeic acid production enhancement by engineering a phenylalanine over-producing *Escherichia coli* strain, *Biotechnol. Bioeng.* 110, 3188-3196.
30. Lin, Y., Sun, X., Yuan, Q., and Yan, Y. (2014) Extending shikimate pathway for the production of muconic acid and its precursor salicylic acid in *Escherichia coli*, *Metab. Eng.* 23C, 62-69.
31. Mora-Pale, M., Sanchez-Rodriguez, S. P., Linhardt, R. J., Dordick, J. S., and Koffas, M. A. (2014) Biochemical 32. Higgins, C. A., Vermeer, L. M., Doom, J. A., and Roman, D. L. (2012) Expression and purification of recombinant human tyrosine hydroxylase as a fusion protein in *Escherichia coli*, *Protein Expr. Purif.* 84, 219-223.

33. Daubner, S. C., Lauriano, C., Haycock, J. W., and Fitzpatrick, P. F. (1992) Site-directed mutagenesis of serine 40 of rat tyrosine hydroxylase. Effects of dopamine and cAMP-dependent phosphorylation on enzyme activity, *J. Biol. Chem.* 267, 12639-12646.

34. Marcheschi, R. J., Gronenberg, L. S., and Liao, J. C. (2013) Protein engineering for metabolic engineering: current and next-generation tools, *Biotechnol. J.* 8, 545-555.

35. Hara, R., and Kino, K. (2013) Enhanced synthesis of 5-hydroxy-1-tryptophan through tetrahydropterin regeneration, *AMB Express* 3, 70.

36. Satoh, Y., Tajima, K., Munekata, M., Keasling, J. D., and Lee, T. S. (2012) Engineering of L-tyrosine oxidation in *Escherichia coli* and microbial production of hydroxytyrosol, *Metab. Eng.* 14, 603-610.

37. Wang, J., Cheng, L. K., Wang, J., Liu, Q., Shen, T., and Chen, N. (2013) Genetic engineering of *Escherichia coli* to enhance production of L-tryptophan, *Appl. Microbiol. Biotechnol.* 97, 7587-7596.

38. Datsenko, K. A., and Wanner, B. L. (2000) One-step inactivation of chromosomal genes in *Escherichia coli* K-12 using PCR products, *Proc. Natl. Acad. Sci. U.S.A.* 97, 6640-6645.

39. Lin, Y., and Yan, Y. (2012) Biosynthesis of caffeic acid in *Escherichia coli* using its endogenous hydroxylase complex, *Microb Cell Fact*11, 42.

40. Shen, X., Lin, Y., Jain, R., Yuan, Q., and Yan, Y. (2012) Inhibition of acetate accumulation leads to enhanced production of (R,R)-2,3-butanediol from glycerol in *Escherichia coli*, *J. Ind. Microbiol. Biotechnol.* 39, 1725-1729.

Example II. 5-Hydroxytryptophan as an Animal Feed Supplement

Milk fever (also called periparturient hypocalcemia) is a metabolic disorder frequently occurring among farm animals around calving period. About 0-10% of dairy cows experience milk fever (clinical hypocalcaemia), while this number can increase to 25% in calving cows (DeGaris et al. 2008, Vet. J. 176, 58-69). Moreover, a majority of dairy cows exhibit different degrees of subclinical hypocalcaemia. Milk fever results in substantial economic losses to dairy farmers, including cow deaths (about 5% of affected cows), reduction in the productive lifespan (3.4 years for each affected cow), decrease in milk production, deterioration in reproductive performance, and costs on prevention and treatment of this disease. On average, the total loss related to milk fever is estimated to be $334 per incidence (Goff et al., 2003, Acta Vet. Scand. Suppl. 97, 145-147). The Food and Agriculture Organization of the United Nations (FAO) has reported that in 2011 there were 260 million dairy cows in the world (World Dairy Cow Number, 2014, available on the worldwide web at dairyco.org.uk/market-information/farming-data/cow-numbers/World-cow-numbers/#.VH0dds6wXxr). Accordingly, the estimated loss caused by milk fever is about $4.34 billion globally (assuming the incidence of severe milk fever is 5%). In contrast, the cows that went through the transition period free of disease usually show a much higher chance to have productive lactation periods, as well as better reproductive performance (Hernandez, 2011, Calsium Homeostasis in Transition Dairy Cattle, available on the worldwide web at reeis.usda.gov/web/crisprojectpages/0227299-calcium-homeostasis-in-transition-dairy-cattle.html.

Extensive studies have shown that elevation of serotonin level during the dry period can increase calcium levels and prevent milk fever. Current practices mainly focus on the manipulation of dietary cation-anion difference in dry cow diets. However, these diets are unpalatable to the animals and also very costly (Id.). Therefore, it is desirable to develop new strategies to control milk fever that are both palatable to the animals and inexpensive for large-scale practice. A recent USDA-funded study entitled "Calcium Homeostasis in Transition Dairy Cattle" revealed that supplementation of 5-HTP resulted in increased calcium mobilization in animals transitioning from pregnancy to lactation, a mechanism that can prevent milk fever effectively (Id.). Horseman et al. claim that 5-HTP supplementation is efficient for the prevention and/or treatment of periparturient hypocalcemia in lactating female mammals (WO2013112873 A2). It should be noted that milk fever occurs among not only cows but also many other farm mammals. However, the high cost and limited supply of the 5-HTP produced by current botanical extraction prevent its use in farm animal feed. Our new technology will reduce the production cost by up to 90%, which would make it economically viable to use 5-HTP as an animal feed additive or supplement in order to prevent milk fever.

The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

In the event that any inconsistency exists between the disclosure of the present application and the disclosure(s) of any document incorporated herein by reference, the disclosure of the present application shall govern.

All headings are for the convenience of the reader and should not be used to limit the meaning of the text that follows the heading, unless so specified.

The complete disclosures of all patents, patent applications including provisional patent applications, publications including patent publications and nonpatent publications, and electronically available material (including, for example, nucleotide sequence submissions in, e.g., Gen- Bank and RefSeq, and amino acid sequence submissions in, e.g., SwissProt, PIR, PRF, PDB, and translations from annotated coding regions in GenBank and RefSeq) cited herein are incorporated by reference

What is claimed is:

1. A genetically engineered bacterial cell comprising a modified bacterial phenylalanine-4-hydroxylase (P4H) that catalyzes the 5-hydroxylation of tryptophan in the presence of a tetrahydromonapterin (MH4) cofactor, wherein the modified P4H comprises a P4H from *Xanthomonas campestris* having an amino acid mutation at any one, any two, or all three of amino acid positions 98, 179, and 231 of SEQ ID NO: 1, or a modified P4H from *Pseudomonas* or *Ralstonia*, selected from the group consisting of: a P4H from *P. aeruginosa* comprising an amino acid mutation at any one, any two, or all three of amino acid positions 84, 162, and 213 of SEQ ID NO: 2, a P4H from *P. putida* having an amino acid mutation at any one, any two, or all three of amino acid positions 84, 162, and 213 of SEQ ID NO: 3, a P4H from *P. fluorescence* comprising an amino acid mutation at any one, any two, or all three of amino acid positions 84, 162, and 213 of SEQ ID NO: 4, or a P4H from *R. eutropha* H16 comprising an amino acid mutation at any one, any two, or all three of amino acid positions 113, 192, and 244 of SEQ ID NO: 5.

2. The genetically engineered bacterial cell of claim 1 which is genetically engineered to overproduce or accumulate tryptophan.

3. The genetically engineered bacterial cell of claim 1 further comprising a cofactor recycling system comprising at least one of a pterin-4a-carbinolamine dehydratase (PCD) and a dihydromonapterin reductase (DHMR).

4. The genetically engineered bacterial cell of claim 3 comprising a dihydromonapterin reductase encoded by the *E. coli* gene folM.

5. The genetically engineered bacterial cell of claim 1 wherein the modified bacterial P4H is derived from a *Pseudomonas, Ralstonia,* or *Xanthomonas*.

6. The genetically engineered bacterial cell of claim 1 wherein the modified P4H is selected from the group consisting of
  (i) a P4H from *X. campestris*, comprising SEQ ID NO:1 modified by any one, any two, or all three amino acid mutations selected from the group consisting of L98Y, W179F and Y231C;
  (ii) a P4H from *P. aeruginosa* comprising SEQ ID NO:2 modified by any one, any two, or all three amino acid mutations selected from the group consisting of L84Y, W162F, and Y213C;
  (ii) a P4H from *P. puticia* comprising SEQ ID NO:3 modified by any one, any two, or all three amino acid mutations selected from the group consisting of L84Y, W162F, and Y213C;
  (iv) a P4H from *P. fluorescence* comprising SEQ ID NO:4 modified by any one, any two, or all three amino acid mutations selected from the group consisting of L84Y, W162F, and Y213C; and
  (v) a P4H from *R. eutropha* H16 comprising SEQ ID NO:5 modified by any one, any two, or all three amino acid mutations selected from the group consisting of L113Y, W192F, and Y244C.

7. The genetically engineered bacterial cell of claim 1 wherein the modified bacterial P4H further comprise at least one further mutation, said further mutation at any one, any two, or all three of amino acid positions 85, 223 and 282 of *X. campestris* P4H (SEQ ID NO: 1).

8. The genetically engineered bacterial cell of claim 1 comprising a first plasmid comprising a polynucleotide operably encoding (a) the modified bacterial P4H and (b) at least one of a pterin-4a-carbinolamine dehydratase (PCD) and a dihydromonapterin reductase (DHMR).

9. The genetically engineered bacterial cell of claim 8 further comprising a second plasmid comprising a polynucleotide operably encoding all or a portion of a trp operon.

10. The genetically engineered bacterial cell of claim 9 wherein the trp operon or portion thereof comprises a mutation S40F in TrpE.

11. The genetically engineered bacterial cell of claim 1 which is an *Escherichia coli* cell, a *Bacillus subtilis* cell, or a *Corynebacterium glutamicum* cell.

12. The genetically engineered bacterial cell of claim 1 which does not comprise a tetrahydrobiopterin (BH4) cofactor.

13. The genetically engineered bacterial cell of claim 1 which comprises an endogenous tetrahydrobiopterin (BH4) cofactor.

14. The genetically engineered bacterial cell of claim 1 which comprises an endogenous tetrahydromonapterin (MH4) cofactor.

15. A method of making 5-hydroxytryptophan (5-HTP) comprising:
   culturing the genetically engineered bacterial cell of claim 1 and for a time sufficient to produce 5-HTP; and
   isolating the 5-HTP.

16. The method of claim 15 further comprising purifying the 5-HTP.

17. The method of claim 15 further comprising incorporating the 5-HTP into a food product.

18. The method of claim 17 wherein the food product is an animal feed or beverage.

19. The method of claim 15 further comprising packaging the 5-HTP for sale.

20. The method of claim 19 further comprising providing instructions for use of the 5-HTP as a food additive, a food supplement, or a nutraceutical.

21. The method of claim 19 wherein the 5-HTP is packaged for use as an animal feed or beverage.

* * * * *

SEQUENCE LISTING

```
<160> NUMBER OF SEQ ID NOS: 17

<210> SEQ ID NO 1
<211> LENGTH: 296
<212> TYPE: PRT
<213> ORGANISM: Xanthomonas campestris

<400> SEQUENCE: 1

Met Asn Thr Ala Pro Arg Arg Val Glu Asn Gln Leu Thr Asp Lys Gly
1               5                   10                  15

Tyr Val Pro Val Tyr Thr Thr Ala Val Val Glu Gln Pro Trp Asp Gly
            20                  25                  30

Tyr Ser Ala Asp Asp His Ala Thr Trp Gly Thr Leu Tyr Arg Arg Gln
        35                  40                  45

Arg Ala Leu Leu Val Gly Arg Ala Cys Asp Glu Phe Leu Gln Ala Gln
    50                  55                  60

Asp Ala Met Gly Met Asp Asp Thr Gln Ile Pro Arg Phe Asp Ala Leu
65                  70                  75                  80

Asn Ala Val Leu Gln Ala Thr Thr Gly Trp Thr Leu Val Gly Val Glu
                85                  90                  95

Gly Leu Leu Pro Glu Leu Asp Phe Phe Asp His Leu Ala Asn Arg Arg
            100                 105                 110

Phe Pro Val Thr Trp Trp Ile Arg Arg Pro Asp Gln Ile Asp Tyr Ile
        115                 120                 125

Ala Glu Pro Asp Leu Phe His Asp Leu Phe Gly His Val Pro Leu Leu
    130                 135                 140

Met Asn Pro Leu Phe Ala Asp Phe Met Gln Ala Tyr Gly Arg Gly Gly
145                 150                 155                 160

Val Lys Ala His Gly Ile Gly Pro Asp Ala Leu Gln Asn Leu Thr Arg
                165                 170                 175

Leu Tyr Trp Tyr Thr Val Glu Phe Gly Leu Ile Ala Thr Pro Gln Gly
            180                 185                 190

Leu Arg Ile Tyr Gly Ala Gly Ile Val Ser Ser Lys Gly Glu Ser Leu
        195                 200                 205

His Ser Leu Glu Ser Ala Ala Pro Asn Arg Val Gly Phe Asp Leu Gln
    210                 215                 220

Arg Val Met Arg Thr Arg Tyr Arg Ile Asp Ser Phe Gln Lys Thr Tyr
225                 230                 235                 240

Phe Val Ile Asp Ser Phe Thr Gln Leu Met Asp Ala Thr Ala Pro Asp
                245                 250                 255

Phe Thr Pro Ile Tyr Ala Ala Leu Ala Gln Gln Pro Gln Val Pro Ala
            260                 265                 270

Gly Glu Val Leu Ala Thr Asp His Val Leu Gln Arg Gly Ser Gly Glu
        275                 280                 285

Gly Trp Ser Arg Asp Gly Asp Val
    290                 295

<210> SEQ ID NO 2
<211> LENGTH: 262
<212> TYPE: PRT
<213> ORGANISM: Pseudomonas aeruginosa

<400> SEQUENCE: 2

Met Lys Thr Thr Gln Tyr Val Ala Arg Gln Pro Asp Asp Asn Gly Phe
```

```
  1               5                  10                 15
Ile His Tyr Pro Glu Thr Glu His Gln Val Trp Asn Thr Leu Ile Thr
                 20                 25                 30
Arg Gln Leu Lys Val Ile Glu Gly Arg Ala Cys Gln Glu Tyr Leu Asp
                 35                 40                 45
Gly Ile Glu Gln Leu Gly Leu Pro His Glu Arg Ile Pro Gln Leu Asp
         50                 55                 60
Glu Ile Asn Arg Val Leu Gln Ala Thr Thr Gly Trp Arg Val Ala Arg
 65                 70                 75                 80
Val Pro Ala Leu Ile Pro Phe Gln Thr Phe Phe Glu Leu Leu Ala Ser
                 85                 90                 95
Gln Gln Phe Pro Val Ala Thr Phe Ile Arg Thr Pro Glu Glu Leu Asp
                100                105                110
Tyr Leu Gln Glu Pro Asp Ile Phe His Glu Ile Phe Gly His Cys Pro
                115                120                125
Leu Leu Thr Asn Pro Trp Phe Ala Glu Phe Thr His Thr Tyr Gly Lys
        130                135                140
Leu Gly Leu Lys Ala Ser Lys Glu Arg Val Phe Leu Ala Arg Leu
145                150                155                160
Tyr Trp Met Thr Ile Glu Phe Gly Leu Val Glu Thr Asp Gln Gly Lys
                165                170                175
Arg Ile Tyr Gly Gly Gly Ile Leu Ser Ser Pro Lys Gly Thr Val Tyr
        180                185                190
Ser Leu Ser Asp Glu Pro Leu His Gln Ala Phe Asn Pro Leu Glu Ala
                195                200                205
Met Arg Thr Pro Tyr Arg Ile Asp Ile Leu Gln Pro Leu Tyr Phe Val
        210                215                220
Leu Pro Asp Leu Lys Arg Leu Phe Gln Leu Ala Gln Glu Asp Ile Met
225                230                235                240
Ala Leu Val His Glu Ala Met Arg Leu Gly Leu His Ala Pro Leu Phe
                245                250                255
Pro Pro Lys Gln Ala Ala
        260

<210> SEQ ID NO 3
<211> LENGTH: 263
<212> TYPE: PRT
<213> ORGANISM: Pseudomonas fluorescens

<400> SEQUENCE: 3

Met Lys Gln Thr Gln Tyr Val Ala Arg Glu Pro Asp Ala Gln Gly Phe
 1               5                  10                 15
Ile Asp Tyr Pro Pro Glu Glu His Ala Val Trp Asn Thr Leu Ile Thr
                 20                 25                 30
Arg Gln Leu Lys Val Ile Glu Gly Arg Ala Cys Gln Glu Tyr Leu Asp
                 35                 40                 45
Gly Ile Asp Lys Leu Gly Leu Pro His Asp Arg Ile Pro Gln Leu Gly
         50                 55                 60
Glu Ile Asn Lys Val Leu Gly Glu Thr Thr Gly Trp Gln Val Ala Arg
 65                 70                 75                 80
Val Pro Ala Leu Ile Pro Phe Gln Thr Phe Phe Glu Leu Leu Ala Ser
                 85                 90                 95
Lys Arg Phe Pro Val Ala Thr Phe Ile Arg Thr Arg Glu Glu Leu Asp
                100                105                110
```

Tyr Leu Gln Glu Pro Asp Ile Phe His Glu Ile Phe Gly His Cys Pro
115                 120                 125

Leu Leu Thr Asn Pro Trp Phe Ala Glu Phe Thr His Thr Tyr Gly Lys
130                 135                 140

Leu Gly Leu Gln Ala Thr Lys Glu Glu Arg Val Tyr Leu Ala Arg Leu
145                 150                 155                 160

Tyr Trp Met Thr Ile Glu Phe Gly Leu Val Asp Thr Pro Ala Gly Arg
                165                 170                 175

Arg Ile Tyr Gly Gly Gly Ile Leu Ser Ser Pro Lys Glu Thr Val Tyr
            180                 185                 190

Ser Leu Ser Glu Glu Pro Glu His Gln Ala Phe Asp Pro Leu Glu Ala
        195                 200                 205

Met Arg Thr Pro Tyr Arg Ile Asp Ile Leu Gln Pro Ile Tyr Phe Thr
    210                 215                 220

Leu Pro Asn Leu Lys Arg Leu Phe Asp Leu Ala His Glu Asp Ile Met
225                 230                 235                 240

Ala Leu Val His Gln Gly Met Gln Leu Gly Leu His Ala Pro Lys Phe
                245                 250                 255

Pro Pro Lys Pro Lys Ala Ala
            260

<210> SEQ ID NO 4
<211> LENGTH: 262
<212> TYPE: PRT
<213> ORGANISM: Pseudomonas putida

<400> SEQUENCE: 4

Met Lys Gln Thr Gln Tyr Val Ala Arg Glu Pro Asp Ala His Gly Phe
1               5                   10                  15

Ile Asp Tyr Pro Gln Gln Glu His Ala Val Trp Asn Thr Leu Ile Thr
                20                  25                  30

Arg Gln Leu Lys Val Ile Glu Gly Arg Ala Cys Gln Glu Tyr Leu Asp
            35                  40                  45

Gly Ile Asp Gln Leu Lys Leu Pro His Asp Arg Ile Pro Gln Leu Gly
        50                  55                  60

Glu Ile Asn Lys Val Leu Gly Ala Thr Thr Gly Trp Gln Val Ala Arg
65                  70                  75                  80

Val Pro Ala Leu Ile Pro Phe Gln Thr Phe Phe Glu Leu Leu Ala Ser
                85                  90                  95

Lys Arg Phe Pro Val Ala Thr Phe Ile Arg Thr Pro Glu Glu Leu Asp
            100                 105                 110

Tyr Leu Gln Glu Pro Asp Ile Phe His Glu Ile Phe Gly His Cys Pro
        115                 120                 125

Leu Leu Thr Asn Pro Trp Phe Ala Glu Phe Thr His Thr Tyr Gly Lys
    130                 135                 140

Leu Gly Leu Ala Ala Thr Lys Glu Gln Arg Val Tyr Leu Ala Arg Leu
145                 150                 155                 160

Tyr Trp Met Thr Ile Glu Phe Gly Leu Met Glu Thr Ala Gln Gly Arg
                165                 170                 175

Lys Ile Tyr Gly Gly Gly Ile Leu Ser Ser Pro Lys Glu Thr Val Tyr
            180                 185                 190

Ser Leu Ser Asp Glu Pro Glu His Gln Ala Phe Asp Pro Ile Glu Ala
        195                 200                 205

Met Arg Thr Pro Tyr Arg Ile Asp Ile Leu Gln Pro Val Tyr Phe Val
    210                 215                 220

```
Leu Pro Asn Met Lys Arg Leu Phe Asp Leu Ala His Glu Asp Ile Met
225                 230                 235                 240

Gly Met Val His Lys Ala Met Gln Leu Gly Leu His Ala Pro Lys Phe
            245                 250                 255

Pro Pro Lys Val Ala Ala
            260

<210> SEQ ID NO 5
<211> LENGTH: 309
<212> TYPE: PRT
<213> ORGANISM: Ralstonia eutropha

<400> SEQUENCE: 5

Met Ser Ile Ala Thr Ala Thr Glu Ala Pro Gly Ala Phe Gln Gly Thr
1               5                   10                  15

Leu Thr Asp Lys Leu Lys Glu Gln Phe Asp Ala Gly Leu Leu Ser Gly
            20                  25                  30

Gln Glu Leu Arg Pro Asp Phe Thr Ile Ala Gln Pro Val His Arg Tyr
        35                  40                  45

Thr Ser Thr Asp His Ala Ile Trp Arg Lys Leu Tyr Glu Arg Gln Ala
50                  55                  60

Ala Met Leu Gln Gly Arg Val Ser Asp Glu Phe Leu Gln Gly Leu Ala
65                  70                  75                  80

Thr Leu Gly Met Asp Lys Asp Arg Val Pro Asp Phe Asp Gln Leu Asn
                85                  90                  95

Glu Thr Leu Met Arg Ala Thr Gly Trp Gln Val Val Ala Val Pro Gly
            100                 105                 110

Leu Val Pro Asp Gln Val Phe Phe Glu His Leu Ala Asn Arg Arg Phe
        115                 120                 125

Pro Ala Ser Trp Trp Met Arg Lys Pro Glu Gln Leu Asp Tyr Leu Gln
130                 135                 140

Glu Pro Asp Cys Phe His Asp Val Phe Gly His Val Pro Leu Leu Ile
145                 150                 155                 160

Asn Pro Val Phe Ala Asp Tyr Met Glu Ala Tyr Gly Lys Gly Gly Leu
                165                 170                 175

Lys Ala Asn Gly Leu Gly Ala Leu Asp Met Leu Ser Arg Leu Tyr Trp
            180                 185                 190

Tyr Thr Val Glu Phe Gly Leu Ile Arg Thr Ala Gln Gly Leu Arg Ile
        195                 200                 205

Tyr Gly Ala Gly Ile Leu Ser Ser Gln Gly Glu Ser Ile Tyr Ser Leu
210                 215                 220

Asp Ser Ala Ser Pro Asn Arg Ile Gly Phe Asp Val Arg Arg Ile Met
225                 230                 235                 240

Arg Thr Arg Tyr Arg Ile Asp Thr Phe Gln Lys Thr Tyr Phe Val Ile
                245                 250                 255

Asp Ser Phe Glu Gln Leu Phe Asp Ala Thr Arg Pro Asp Phe Ala Pro
            260                 265                 270

Leu Tyr Glu Glu Leu Arg Ala Gln Pro Thr Leu Gly Ala Gly Asp Val
        275                 280                 285

Ala Pro Gly Asp Gln Val Leu Asn Val Gly Thr Arg Glu Gly Trp Ala
290                 295                 300

Asp Thr Glu Asp Ile
305
```

```
<210> SEQ ID NO 6
<211> LENGTH: 490
<212> TYPE: PRT
<213> ORGANISM: Homo sapiens

<400> SEQUENCE: 6

Met Gln Pro Ala Met Met Met Phe Ser Ser Lys Tyr Trp Ala Arg Arg
1               5                   10                  15

Gly Phe Ser Leu Asp Ser Ala Val Pro Glu Glu His Gln Leu Leu Gly
                20                  25                  30

Ser Ser Thr Leu Asn Lys Pro Asn Ser Gly Lys Asn Asp Asp Lys Gly
            35                  40                  45

Asn Lys Gly Ser Ser Lys Arg Glu Ala Ala Thr Glu Ser Gly Lys Thr
50                  55                  60

Ala Val Val Phe Ser Leu Lys Asn Glu Val Gly Gly Leu Val Lys Ala
65                  70                  75                  80

Leu Arg Leu Phe Gln Glu Lys Arg Val Asn Met Val His Ile Glu Ser
                85                  90                  95

Arg Lys Ser Arg Arg Arg Ser Ser Glu Val Glu Ile Phe Val Asp Cys
            100                 105                 110

Glu Cys Gly Lys Thr Glu Phe Asn Glu Leu Ile Gln Leu Leu Lys Phe
        115                 120                 125

Gln Thr Thr Ile Val Thr Leu Asn Pro Pro Glu Asn Ile Trp Thr Glu
130                 135                 140

Glu Glu Glu Leu Glu Asp Val Pro Trp Phe Pro Arg Lys Ile Ser Glu
145                 150                 155                 160

Leu Asp Lys Cys Ser His Arg Val Leu Met Tyr Gly Ser Glu Leu Asp
                165                 170                 175

Ala Asp His Pro Gly Phe Lys Asp Asn Val Tyr Arg Gln Arg Arg Lys
            180                 185                 190

Tyr Phe Val Asp Val Ala Met Gly Tyr Lys Tyr Gly Gln Pro Ile Pro
        195                 200                 205

Arg Val Glu Tyr Thr Glu Glu Glu Thr Lys Thr Trp Gly Val Val Phe
210                 215                 220

Arg Glu Leu Ser Lys Leu Tyr Pro Thr His Ala Cys Arg Glu Tyr Leu
225                 230                 235                 240

Lys Asn Phe Pro Leu Leu Thr Lys Tyr Cys Gly Tyr Arg Glu Asp Asn
                245                 250                 255

Val Pro Gln Leu Glu Asp Val Ser Met Phe Leu Lys Glu Arg Ser Gly
            260                 265                 270

Phe Thr Val Arg Pro Val Ala Gly Tyr Leu Ser Pro Arg Asp Phe Leu
        275                 280                 285

Ala Gly Leu Ala Tyr Arg Val Phe His Cys Thr Gln Tyr Ile Arg His
290                 295                 300

Gly Ser Asp Pro Leu Tyr Thr Pro Glu Pro Asp Thr Cys His Glu Leu
305                 310                 315                 320

Leu Gly His Val Pro Leu Leu Ala Asp Pro Lys Phe Ala Gln Phe Ser
                325                 330                 335

Gln Glu Ile Gly Leu Ala Ser Leu Gly Ala Ser Asp Glu Asp Val Gln
            340                 345                 350

Lys Leu Ala Thr Cys Tyr Phe Phe Thr Ile Glu Phe Gly Leu Cys Lys
        355                 360                 365

Gln Glu Gly Gln Leu Arg Ala Tyr Gly Ala Gly Leu Leu Ser Ser Ile
370                 375                 380
```

-continued

Gly Glu Leu Lys His Ala Leu Ser Asp Lys Ala Cys Val Lys Ala Phe
385                 390                 395                 400

Asp Pro Lys Thr Thr Cys Leu Gln Glu Cys Leu Ile Thr Thr Phe Gln
            405                 410                 415

Glu Ala Tyr Phe Val Ser Glu Ser Phe Glu Glu Ala Lys Glu Lys Met
        420                 425                 430

Arg Asp Phe Ala Lys Ser Ile Thr Arg Pro Phe Ser Val Tyr Phe Asn
    435                 440                 445

Pro Tyr Thr Gln Ser Ile Glu Ile Leu Lys Asp Thr Arg Ser Ile Glu
450                 455                 460

Asn Val Val Gln Asp Leu Arg Ser Asp Leu Asn Thr Val Cys Asp Ala
465                 470                 475                 480

Leu Asn Lys Met Asn Gln Tyr Leu Gly Ile
                485                 490

<210> SEQ ID NO 7
<211> LENGTH: 488
<212> TYPE: PRT
<213> ORGANISM: Mus musculus

<400> SEQUENCE: 7

Met Gln Pro Ala Met Met Phe Ser Ser Lys Tyr Trp Ala Arg Arg
1               5                   10                  15

Gly Leu Ser Leu Asp Ser Ala Val Pro Glu Asp His Gln Leu Leu Gly
            20                  25                  30

Ser Leu Thr Gln Asn Lys Ala Ile Lys Ser Glu Asp Lys Lys Ser Gly
        35                  40                  45

Lys Glu Pro Gly Lys Gly Asp Thr Thr Glu Ser Ser Lys Thr Ala Val
50                  55                  60

Val Phe Ser Leu Lys Asn Glu Val Gly Gly Leu Val Lys Ala Leu Arg
65                  70                  75                  80

Leu Phe Gln Glu Lys His Val Asn Met Leu His Ile Glu Ser Arg Arg
                85                  90                  95

Ser Arg Arg Arg Ser Ser Glu Val Glu Ile Phe Val Asp Cys Glu Cys
            100                 105                 110

Gly Lys Thr Glu Phe Asn Glu Leu Ile Gln Leu Leu Lys Phe Gln Thr
        115                 120                 125

Thr Ile Val Thr Leu Asn Pro Pro Glu Ser Ile Trp Thr Glu Glu Glu
    130                 135                 140

Asp Leu Glu Asp Val Pro Trp Phe Pro Arg Lys Ile Ser Glu Leu Asp
145                 150                 155                 160

Arg Cys Ser His Arg Val Leu Met Tyr Gly Thr Glu Leu Asp Ala Asp
                165                 170                 175

His Pro Gly Phe Lys Asp Asn Val Tyr Arg Gln Arg Arg Lys Tyr Phe
            180                 185                 190

Val Asp Val Ala Met Gly Tyr Lys Tyr Gly Gln Pro Ile Pro Arg Val
        195                 200                 205

Glu Tyr Thr Glu Glu Glu Thr Lys Thr Trp Gly Val Val Phe Arg Glu
    210                 215                 220

Leu Ser Lys Leu Tyr Pro Thr His Ala Cys Arg Glu Tyr Leu Lys Asn
225                 230                 235                 240

Leu Pro Leu Leu Thr Lys Tyr Cys Gly Tyr Arg Glu Asp Asn Val Pro
                245                 250                 255

Gln Leu Glu Asp Val Ser Met Phe Leu Lys Glu Arg Ser Gly Phe Thr
            260                 265                 270

Val Arg Pro Val Ala Gly Tyr Leu Ser Pro Arg Asp Phe Leu Ala Gly
    275                 280                 285

Leu Ala Tyr Arg Val Phe His Cys Thr Gln Tyr Val Arg His Gly Ser
290                 295                 300

Asp Pro Leu Tyr Thr Pro Glu Pro Asp Thr Cys His Glu Leu Leu Gly
305                 310                 315                 320

His Val Pro Leu Leu Ala Asp Pro Lys Phe Ala Gln Phe Ser Gln Glu
                325                 330                 335

Ile Gly Leu Ala Ser Leu Gly Ala Ser Asp Glu Asp Val Gln Lys Leu
                340                 345                 350

Ala Thr Cys Tyr Phe Phe Thr Ile Glu Phe Gly Leu Cys Lys Gln Glu
                355                 360                 365

Gly Gln Leu Arg Ala Tyr Gly Ala Gly Leu Leu Ser Ser Ile Gly Glu
    370                 375                 380

Leu Lys His Ala Leu Ser Asp Lys Ala Cys Val Lys Ser Phe Asp Pro
385                 390                 395                 400

Lys Thr Thr Cys Leu Gln Glu Cys Leu Ile Thr Thr Phe Gln Asp Ala
                405                 410                 415

Tyr Phe Val Ser Asp Ser Phe Glu Glu Ala Lys Glu Lys Met Arg Asp
                420                 425                 430

Phe Ala Lys Ser Ile Thr Arg Pro Phe Ser Val Tyr Phe Asn Pro Tyr
            435                 440                 445

Thr Gln Ser Ile Glu Ile Leu Lys Asp Thr Arg Ser Ile Glu Asn Val
    450                 455                 460

Val Gln Asp Leu Arg Ser Asp Leu Asn Thr Val Cys Asp Ala Leu Asn
465                 470                 475                 480

Lys Met Asn Gln Tyr Leu Gly Ile
                485

<210> SEQ ID NO 8
<211> LENGTH: 489
<212> TYPE: PRT
<213> ORGANISM: Gallus gallus

<400> SEQUENCE: 8

Met Gln Pro Ala Met Met Met Phe Ser Ser Lys Tyr Trp Ala Arg Arg
1               5                   10                  15

Gly Phe Ser Leu Asp Ser Ala Leu Pro Glu Glu Arg Pro Gly Gly Leu
                20                  25                  30

Thr Ile Asn Arg Ser Ser Ser Gly Lys Asn Glu Asp Lys Lys Gly Asn
            35                  40                  45

Lys Gly Asn Gly Lys Gly Glu Ser Val Ser Glu Gly Gly Lys Thr Ala
        50                  55                  60

Val Val Phe Ser Leu Lys Asn Glu Val Gly Gly Leu Val Lys Ala Leu
65                  70                  75                  80

Arg Leu Phe Gln Glu Lys His Val Ser Met Val His Ile Glu Ser Arg
                85                  90                  95

Lys Ser Lys Arg Arg Asn Ser Glu Val Glu Ile Phe Val Asp Cys Asp
                100                 105                 110

Cys Ser Lys Lys Glu Phe Asn Glu Leu Ile Gln Leu Leu Lys Phe Gln
            115                 120                 125

Thr Asn Ile Val Ser Leu Asn Pro Pro Glu Asn Ile Trp Thr Asp Glu
    130                 135                 140

Glu Asp Leu Asp Cys Val Pro Trp Phe Pro Arg Lys Ile Ser Glu Leu

```
                145                 150                 155                 160
Asp Lys Cys Ser Gln Arg Val Leu Met Tyr Gly Ser Glu Leu Asp Ala
                165                 170                 175

Asp His Pro Gly Phe Lys Asp Asn Val Tyr Arg Gln Arg Lys Tyr
            180                 185                 190

Phe Val Asp Val Ala Met Ser Tyr Lys Tyr Gly Gln Pro Ile Pro Arg
        195                 200                 205

Val Glu Tyr Thr Ala Glu Ile Lys Thr Trp Gly Val Val Phe Arg
    210                 215                 220

Glu Leu Ser Lys Leu Tyr Pro Thr His Ala Cys Arg Glu Tyr Leu Lys
225                 230                 235                 240

Asn Phe Pro Leu Leu Thr Lys Tyr Cys Gly Tyr Arg Glu Asp Asn Val
                245                 250                 255

Pro Gln Leu Glu Asp Val Ser Ile Phe Leu Lys Glu Arg Ser Gly Phe
            260                 265                 270

Thr Val Arg Pro Val Ala Gly Tyr Leu Ser Pro Arg Asp Phe Leu Ala
        275                 280                 285

Gly Leu Ala Tyr Arg Val Phe His Cys Thr Gln Tyr Val Arg His Gly
    290                 295                 300

Ser Asp Pro Leu Tyr Thr Pro Glu Pro Asp Thr Cys His Glu Leu Leu
305                 310                 315                 320

Gly His Val Pro Leu Leu Ala Asp Pro Lys Phe Ala Gln Phe Ser Gln
                325                 330                 335

Glu Ile Gly Leu Ala Ser Leu Gly Ala Ser Asp Glu Asp Val Gln Lys
            340                 345                 350

Leu Ala Thr Cys Tyr Phe Phe Thr Ile Glu Phe Gly Leu Cys Lys Gln
        355                 360                 365

Glu Gly Gln Leu Arg Ala Tyr Gly Ala Gly Leu Leu Ser Ser Ile Gly
    370                 375                 380

Glu Leu Lys His Ala Leu Ser Asp Lys Ala Lys Val Lys Thr Phe Asp
385                 390                 395                 400

Pro Lys Thr Thr Cys Leu Gln Glu Cys Leu Ile Thr Thr Phe Gln Glu
                405                 410                 415

Ala Tyr Phe Val Ser Glu Ser Phe Glu Glu Ala Lys Glu Lys Met Arg
            420                 425                 430

Asp Phe Ala Lys Ser Ile Asn Arg Pro Phe Ser Val Tyr Phe Asn Pro
        435                 440                 445

Tyr Thr Gln Ser Ile Glu Ile Leu Lys Asp Thr Arg Ser Ile Glu Asn
    450                 455                 460

Val Val Gln Asp Leu Arg Ser Asp Leu Asn Thr Val Cys Asp Ala Leu
465                 470                 475                 480

Ser Lys Met Asn Arg Tyr Leu Gly Ile
                485

<210> SEQ ID NO 9
<211> LENGTH: 444
<212> TYPE: PRT
<213> ORGANISM: Bos taurus

<400> SEQUENCE: 9

Met Ile Glu Asp Asn Lys Glu Asn Lys Asp His Ser Phe Glu Arg Gly
1               5                   10                  15

Arg Ala Thr Leu Ile Phe Ser Leu Lys Asn Glu Val Gly Gly Leu Ile
            20                  25                  30
```

```
Lys Ala Leu Lys Ile Phe Gln Glu Lys His Val Asn Leu His Ile
            35                  40                  45
Glu Ser Arg Lys Ser Arg Arg Ser Ser Phe Glu Ile Phe Val
 50                  55                  60
Asp Cys Asp Ile Ser Arg Glu Gln Leu Asn Asp Ile Phe His Leu Leu
 65                  70                  75                  80
Lys Ser His Ser Asn Ile Leu Ser Val Asn Leu Pro Asp Asn Phe Thr
                 85                  90                  95
Val Lys Glu Asp Gly Met Glu Thr Val Pro Trp Phe Pro Lys Lys Ile
            100                 105                 110
Ser Asp Leu Asp His Cys Ala Asn Arg Val Leu Met Tyr Gly Ser Glu
            115                 120                 125
Leu Asp Ala Asp His Pro Gly Phe Lys Asp Asn Val Tyr Arg Lys Arg
            130                 135                 140
Arg Lys Tyr Phe Ala Asp Leu Ala Met Asn Tyr Lys His Gly Asp Pro
145                 150                 155                 160
Ile Pro Arg Val Glu Phe Thr Glu Glu Ile Arg Thr Trp Gly Thr
                 165                 170                 175
Val Phe Arg Glu Leu Asn Lys Leu Tyr Pro Thr His Ala Cys Arg Glu
                 180                 185                 190
Tyr Leu Lys Asn Leu Pro Leu Leu Ser Lys Tyr Cys Gly Tyr Arg Glu
            195                 200                 205
Asp Asn Ile Pro Gln Leu Glu Asp Val Ser Asn Phe Leu Lys Glu Arg
            210                 215                 220
Thr Gly Phe Ser Ile Arg Pro Val Ala Gly Tyr Leu Ser Pro Arg Asp
225                 230                 235                 240
Phe Leu Ser Gly Leu Ala Phe Arg Val Phe His Cys Thr Gln Tyr Val
                 245                 250                 255
Arg His Ser Ser Asp Pro Leu Tyr Thr Pro Glu Pro Asp Thr Cys His
                 260                 265                 270
Glu Leu Leu Gly His Val Pro Leu Leu Ala Glu Pro Ser Phe Ala Gln
            275                 280                 285
Phe Ser Gln Glu Ile Gly Leu Ala Ser Leu Gly Ala Ser Glu Glu Ala
            290                 295                 300
Val Gln Lys Leu Ala Thr Cys Tyr Phe Phe Thr Val Glu Phe Gly Leu
305                 310                 315                 320
Cys Lys Gln Glu Gly Gln Leu Arg Val Phe Gly Ala Gly Leu Leu Ser
                 325                 330                 335
Ser Ile Ser Glu Leu Lys His Ala Leu Ser Gly His Ala Lys Val Lys
            340                 345                 350
Pro Phe Asp Pro Lys Ile Thr Cys Lys Gln Glu Cys Leu Ile Thr Thr
            355                 360                 365
Phe Gln Asp Val Tyr Phe Val Ser Glu Ser Phe Glu Asp Ala Lys Glu
            370                 375                 380
Lys Met Arg Glu Phe Thr Lys Thr Ile Lys Arg Pro Phe Gly Val Lys
385                 390                 395                 400
Tyr Asn Pro Tyr Thr Arg Ser Ile Gln Ile Leu Lys Asp Thr Arg Ser
                 405                 410                 415
Ile Thr Ser Ala Met Asn Glu Leu Gln His Glu Leu Asp Val Val Ser
            420                 425                 430
Asp Ala Leu Ala Lys Val Ser Arg Gln Leu Ser Ile
            435                 440
```

<210> SEQ ID NO 10
<211> LENGTH: 444
<212> TYPE: PRT
<213> ORGANISM: Homo sapiens

<400> SEQUENCE: 10

```
Met Ile Glu Asp Asn Lys Glu Asn Lys Asp His Ser Leu Glu Arg Gly
  1               5                  10                  15

Arg Ala Ser Leu Ile Phe Ser Leu Lys Asn Glu Val Gly Gly Leu Ile
             20                  25                  30

Lys Ala Leu Lys Ile Phe Gln Glu Lys His Val Asn Leu Leu His Ile
         35                  40                  45

Glu Ser Arg Lys Ser Lys Arg Arg Asn Ser Glu Phe Glu Ile Phe Val
 50                  55                  60

Asp Cys Asp Ile Asn Arg Glu Gln Leu Asn Asp Ile Phe His Leu Leu
 65                  70                  75                  80

Lys Ser His Thr Asn Val Leu Ser Val Asn Leu Pro Asp Asn Phe Thr
                 85                  90                  95

Leu Lys Glu Asp Gly Met Glu Thr Val Pro Trp Phe Pro Lys Lys Ile
            100                 105                 110

Ser Asp Leu Asp His Cys Ala Asn Arg Val Leu Met Tyr Gly Ser Glu
        115                 120                 125

Leu Asp Ala Asp His Pro Gly Phe Lys Asp Asn Val Tyr Arg Lys Arg
130                 135                 140

Arg Lys Tyr Phe Ala Asp Leu Ala Met Asn Tyr Lys His Gly Asp Pro
145                 150                 155                 160

Ile Pro Lys Val Glu Phe Thr Glu Glu Ile Lys Thr Trp Gly Thr
                165                 170                 175

Val Phe Gln Glu Leu Asn Lys Leu Tyr Pro Thr His Ala Cys Arg Glu
            180                 185                 190

Tyr Leu Lys Asn Leu Pro Leu Leu Ser Lys Tyr Cys Gly Tyr Arg Glu
        195                 200                 205

Asp Asn Ile Pro Gln Leu Glu Asp Val Ser Asn Phe Leu Lys Glu Arg
    210                 215                 220

Thr Gly Phe Ser Ile Arg Pro Val Ala Gly Tyr Leu Ser Pro Arg Asp
225                 230                 235                 240

Phe Leu Ser Gly Leu Ala Phe Arg Val Phe His Cys Thr Gln Tyr Val
                245                 250                 255

Arg His Ser Ser Asp Pro Phe Tyr Thr Pro Glu Pro Asp Thr Cys His
            260                 265                 270

Glu Leu Leu Gly His Val Pro Leu Leu Ala Glu Pro Ser Phe Ala Gln
        275                 280                 285

Phe Ser Gln Glu Ile Gly Leu Ala Ser Leu Gly Ala Ser Glu Glu Ala
    290                 295                 300

Val Gln Lys Leu Ala Thr Cys Tyr Phe Phe Thr Val Glu Phe Gly Leu
305                 310                 315                 320

Cys Lys Gln Asp Gly Gln Leu Arg Val Phe Gly Ala Gly Leu Leu Ser
                325                 330                 335

Ser Ile Ser Glu Leu Lys His Ala Leu Ser Gly His Ala Lys Val Lys
            340                 345                 350

Pro Phe Asp Pro Lys Ile Thr Cys Lys Gln Glu Cys Leu Ile Thr Thr
        355                 360                 365

Phe Gln Asp Val Tyr Phe Val Ser Glu Ser Phe Glu Asp Ala Lys Glu
    370                 375                 380
```

```
Lys Met Arg Glu Phe Thr Lys Thr Ile Lys Arg Pro Phe Gly Val Lys
385                 390                 395                 400

Tyr Asn Pro Tyr Thr Arg Ser Ile Gln Ile Leu Lys Asp Thr Lys Ser
            405                 410                 415

Ile Thr Ser Ala Met Asn Glu Leu Gln His Asp Leu Asp Val Val Ser
            420                 425                 430

Asp Ala Leu Ala Lys Val Ser Arg Lys Pro Ser Ile
            435                 440

<210> SEQ ID NO 11
<211> LENGTH: 447
<212> TYPE: PRT
<213> ORGANISM: Mus musculus

<400> SEQUENCE: 11

Met Ile Glu Asp Asn Lys Glu Asn Lys Asp His Ser Ser
1               5                   10                  15

Glu Arg Gly Arg Val Thr Leu Ile Phe Ser Leu Glu Asn Glu Val Gly
            20                  25                  30

Gly Leu Ile Lys Val Leu Lys Ile Phe Gln Glu Asn His Val Ser Leu
        35                  40                  45

Leu His Ile Glu Ser Arg Lys Ser Lys Gln Arg Asn Ser Glu Phe Glu
50                  55                  60

Ile Phe Val Asp Cys Asp Ile Ser Arg Glu Gln Leu Asn Asp Ile Phe
65                  70                  75                  80

Pro Leu Leu Lys Ser His Ala Thr Val Leu Ser Val Asp Ser Pro Asp
                85                  90                  95

Gln Leu Thr Ala Lys Glu Asp Val Met Glu Thr Val Pro Trp Phe Pro
            100                 105                 110

Lys Lys Ile Ser Asp Leu Asp Phe Cys Ala Asn Arg Val Leu Leu Tyr
        115                 120                 125

Gly Ser Glu Leu Asp Ala Asp His Pro Gly Phe Lys Asp Asn Val Tyr
130                 135                 140

Arg Arg Arg Arg Lys Tyr Phe Ala Glu Leu Ala Met Asn Tyr Lys His
145                 150                 155                 160

Gly Asp Pro Ile Pro Lys Ile Glu Phe Thr Glu Glu Ile Lys Thr
                165                 170                 175

Trp Gly Thr Ile Phe Arg Glu Leu Asn Lys Leu Tyr Pro Thr His Ala
            180                 185                 190

Cys Arg Glu Tyr Leu Arg Asn Leu Pro Leu Leu Ser Lys Tyr Cys Gly
        195                 200                 205

Tyr Arg Glu Asp Asn Ile Pro Gln Leu Glu Asp Val Ser Asn Phe Leu
210                 215                 220

Lys Glu Arg Thr Gly Phe Ser Ile Arg Pro Val Ala Gly Tyr Leu Ser
225                 230                 235                 240

Pro Arg Asp Phe Leu Ser Gly Leu Ala Phe Arg Val Phe His Cys Thr
                245                 250                 255

Gln Tyr Val Arg His Ser Ser Asp Pro Leu Tyr Thr Pro Glu Pro Asp
            260                 265                 270

Thr Cys His Glu Leu Leu Gly His Val Pro Leu Leu Ala Glu Pro Ser
        275                 280                 285

Phe Ala Gln Phe Ser Gln Glu Ile Gly Leu Ala Ser Leu Gly Ala Ser
290                 295                 300

Glu Glu Thr Val Gln Lys Leu Ala Thr Cys Tyr Phe Phe Thr Val Glu
305                 310                 315                 320
```

```
Phe Gly Leu Cys Lys Gln Asp Gly Gln Leu Arg Val Phe Gly Ala Gly
            325                 330                 335

Leu Leu Ser Ser Ile Ser Glu Leu Lys His Ala Leu Ser Gly His Ala
            340                 345                 350

Lys Val Lys Pro Phe Asp Pro Lys Ile Ala Cys Lys Gln Glu Cys Leu
            355                 360                 365

Ile Thr Ser Phe Gln Asp Val Tyr Phe Val Ser Glu Ser Phe Glu Asp
            370                 375                 380

Ala Lys Glu Lys Met Arg Glu Phe Ala Lys Thr Val Lys Arg Pro Phe
385                 390                 395                 400

Gly Leu Lys Tyr Asn Pro Tyr Thr Gln Ser Val Gln Val Leu Arg Asp
                405                 410                 415

Thr Lys Ser Ile Thr Ser Ala Met Asn Glu Leu Arg Tyr Asp Leu Asp
            420                 425                 430

Val Ile Ser Asp Ala Leu Ala Arg Val Thr Arg Trp Pro Ser Val
            435                 440                 445
```

<210> SEQ ID NO 12
<211> LENGTH: 445
<212> TYPE: PRT
<213> ORGANISM: Gallus gallus

<400> SEQUENCE: 12

```
Met Ile Glu Asp Asn Lys Glu Asn Lys Asp His Ala Pro Glu Arg Gly
1               5                   10                  15

Arg Thr Ala Ile Ile Phe Ser Leu Lys Asn Glu Val Gly Gly Leu Val
            20                  25                  30

Lys Ala Leu Lys Leu Phe Gln Glu Lys His Val Asn Leu Val His Ile
            35                  40                  45

Glu Ser Arg Lys Ser Lys Arg Arg Asn Ser Glu Phe Glu Ile Phe Val
            50                  55                  60

Asp Cys Asp Ser Asn Arg Glu Gln Leu Asn Glu Ile Phe Gln Leu Leu
65                  70                  75                  80

Lys Ser His Val Ser Ile Val Ser Met Asn Pro Thr Glu His Phe Asn
                85                  90                  95

Val Gln Glu Asp Gly Asp Met Glu Asn Ile Pro Trp Tyr Pro Lys Lys
            100                 105                 110

Ile Ser Asp Leu Asp Lys Cys Ala Asn Arg Val Leu Met Tyr Gly Ser
            115                 120                 125

Asp Leu Asp Ala Asp His Pro Gly Phe Lys Asp Asn Val Tyr Arg Lys
            130                 135                 140

Arg Arg Lys Tyr Phe Ala Asp Leu Ala Met Asn Tyr Lys His Gly Asp
145                 150                 155                 160

Pro Ile Pro Glu Ile Glu Phe Thr Glu Glu Glu Ile Lys Thr Trp Gly
                165                 170                 175

Thr Val Tyr Arg Glu Leu Asn Lys Leu Tyr Pro Thr His Ala Cys Arg
            180                 185                 190

Glu Tyr Leu Lys Asn Leu Pro Leu Leu Thr Lys Tyr Cys Gly Tyr Arg
            195                 200                 205

Glu Asp Asn Ile Pro Gln Leu Glu Asp Val Ser Arg Phe Leu Lys Glu
            210                 215                 220

Arg Thr Gly Phe Thr Ile Arg Pro Val Ala Gly Tyr Leu Ser Pro Arg
225                 230                 235                 240

Asp Phe Leu Ala Gly Leu Ala Phe Arg Val Phe His Cys Thr Gln Tyr
```

```
            245                 250                 255
Val Arg His Ser Ser Asp Pro Leu Tyr Thr Pro Glu Pro Asp Thr Cys
            260                 265                 270

His Glu Leu Leu Gly His Val Pro Leu Leu Ala Glu Pro Ser Phe Ala
            275                 280                 285

Gln Phe Ser Gln Glu Ile Gly Leu Ala Ser Leu Gly Ala Ser Asp Glu
290                 295                 300

Ala Val Gln Lys Leu Ala Thr Cys Tyr Phe Phe Thr Val Glu Phe Gly
305                 310                 315                 320

Leu Cys Lys Gln Glu Gly Gln Leu Arg Val Tyr Gly Ala Gly Leu Leu
            325                 330                 335

Ser Ser Ile Ser Glu Leu Lys His Ser Leu Ser Gly Ser Ala Lys Val
            340                 345                 350

Lys Pro Phe Asp Pro Lys Val Thr Cys Lys Gln Glu Cys Leu Ile Thr
            355                 360                 365

Thr Phe Gln Glu Val Tyr Phe Val Ser Glu Ser Phe Glu Glu Ala Lys
            370                 375                 380

Glu Lys Met Arg Glu Phe Ala Lys Thr Ile Lys Arg Pro Phe Gly Val
385                 390                 395                 400

Lys Tyr Asn Pro Tyr Thr Gln Ser Val Gln Ile Leu Lys Asp Thr Lys
            405                 410                 415

Ser Ile Ala Ser Val Val Asn Glu Leu Arg His Glu Leu Asp Ile Val
            420                 425                 430

Ser Asp Ala Leu Ser Lys Met Gly Lys Gln Leu Glu Val
            435                 440                 445

<210> SEQ ID NO 13
<211> LENGTH: 452
<212> TYPE: PRT
<213> ORGANISM: Homo sapiens

<400> SEQUENCE: 13

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
    50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175
```

```
Val Glu Tyr Met Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
        355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu
        435                 440                 445

Gln Lys Ile Lys
    450

<210> SEQ ID NO 14
<211> LENGTH: 466
<212> TYPE: PRT
<213> ORGANISM: Oryctolagus cuniculus

<400> SEQUENCE: 14

Met Ser Ala Val Val Leu Glu Asn Gly Gly Leu Ser Arg Lys Phe Ser
1               5                   10                  15

Asp Phe Gly Gln Glu Thr Ser Tyr Ile Glu Asp Asn Ser Asn Glu Asn
            20                  25                  30

Ser Ala Ile Ser Leu Ile Phe Ser Leu Lys Glu Glu Val Gly Ala Leu
        35                  40                  45

Ala Lys Val Leu Arg Leu Phe Glu Glu Asn Asp Ile Asn Leu Thr His
    50                  55                  60

Ile Glu Ser Arg Pro Ser Arg Leu Lys Lys Asp Glu Tyr Glu Phe Phe
65                  70                  75                  80

Thr Tyr Leu Asp Lys Arg Ser Met Pro Ala Leu Glu Asp Ile Ile Gln
                85                  90                  95
```

```
Ile Leu Arg His Asp Ile Gly Ala Thr Val His Glu Leu Ser Arg Asp
                100                 105                 110

Lys Lys Lys Asp Thr Val Pro Trp Phe Pro Arg Thr Ile Gln Glu Leu
            115                 120                 125

Asp Arg Phe Ala Asn Gln Ile Leu Ser Tyr Gly Ala Glu Leu Asp Ala
        130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Thr Glu Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe Arg Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Phe Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Gly Lys Pro Lys Leu Leu Pro Leu Glu
        355                 360                 365

Leu Glu Lys Thr Ala Ile Gln Glu Tyr Pro Val Thr Glu Phe Gln Pro
    370                 375                 380

Leu Tyr Tyr Val Ala Glu Ser Phe Met Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Ile Leu Asp Asn Thr Gln Gln Leu Lys Ile
            420                 425                 430

Leu Ala Asp Ser Ile Asn Ser Glu Val Gly Ile Leu Cys Asn Ala Leu
        435                 440                 445

Gln Lys Asn Lys Ser Glu Ala Ile Tyr Arg Ile Gly Leu Ser Thr Asp
    450                 455                 460

His Cys
465

<210> SEQ ID NO 15
<211> LENGTH: 453
<212> TYPE: PRT
<213> ORGANISM: Mus musculus
```

<400> SEQUENCE: 15

```
Met Ala Ala Val Val Leu Glu Asn Gly Val Leu Ser Arg Lys Leu Ser
1               5                   10                  15

Asp Phe Gly Gln Glu Thr Ser Tyr Ile Glu Asp Asn Ser Asn Gln Asn
            20                  25                  30

Gly Ala Val Ser Leu Ile Phe Ser Leu Lys Glu Val Gly Ala Leu
        35                  40                  45

Ala Lys Val Leu Arg Leu Phe Glu Glu Asn Ile Asn Leu Thr His
50                  55                  60

Ile Glu Ser Arg Pro Ser Arg Leu Asn Lys Asp Glu Tyr Glu Phe Phe
65                  70                  75                  80

Thr Tyr Leu Asp Lys Arg Ser Lys Pro Val Leu Gly Ser Ile Ile Lys
                85                  90                  95

Ser Leu Arg Asn Asp Ile Gly Ala Thr Val His Glu Leu Ser Arg Asp
            100                 105                 110

Lys Glu Lys Asn Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Thr Glu Glu Glu Arg Lys Thr Trp Gly Thr Val Phe Arg
            180                 185                 190

Thr Leu Lys Ala Leu Tyr Lys Thr His Ala Cys Tyr Glu His Asn His
        195                 200                 205

Ile Phe Pro Leu Leu Glu Lys Tyr Cys Gly Phe Arg Glu Asp Asn Ile
210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Glu
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Asp Lys Pro Lys Leu Leu Pro Leu Glu
        355                 360                 365

Leu Glu Lys Thr Ala Cys Gln Glu Tyr Thr Val Thr Glu Phe Gln Pro
370                 375                 380

Leu Tyr Tyr Val Ala Glu Ser Phe Asn Asp Ala Lys Glu Lys Val Arg
385                 390                 395                 400

Thr Phe Ala Ala Thr Ile Pro Arg Pro Phe Ser Val Arg Tyr Asp Pro
                405                 410                 415
```

Tyr Thr Gln Arg Val Glu Val Leu Asp Asn Thr Gln Leu Lys Ile
            420                 425                 430

Leu Ala Asp Ser Ile Asn Ser Glu Val Gly Ile Leu Cys His Ala Leu
        435                 440                 445

Gln Lys Ile Lys Ser
    450

<210> SEQ ID NO 16
<211> LENGTH: 451
<212> TYPE: PRT
<213> ORGANISM: Bos taurus

<400> SEQUENCE: 16

Met Ser Ala Leu Val Leu Glu Ser Arg Ala Leu Gly Arg Lys Leu Ser
1               5                   10                  15

Asp Phe Gly Gln Glu Thr Ser Tyr Ile Glu Gly Asn Ser Asp Gln Asn
            20                  25                  30

Ala Val Ser Leu Ile Phe Ser Leu Lys Glu Glu Val Gly Ala Leu Ala
        35                  40                  45

Arg Val Leu Arg Leu Phe Glu Glu Asn Asp Ile Asn Leu Thr His Ile
    50                  55                  60

Glu Ser Arg Pro Ser Arg Leu Arg Lys Asp Glu Tyr Glu Phe Phe Thr
65                  70                  75                  80

Asn Leu Asp Gln Arg Ser Val Pro Ala Leu Ala Asn Ile Ile Lys Ile
                85                  90                  95

Leu Arg His Asp Ile Gly Ala Thr Val His Glu Leu Ser Arg Asp Lys
            100                 105                 110

Lys Lys Asp Thr Val Pro Trp Phe Pro Arg Thr Ile Gln Glu Leu Asp
        115                 120                 125

Asn Phe Ala Asn Gln Val Leu Ser Tyr Gly Ala Glu Leu Asp Ala Asp
    130                 135                 140

His Pro Gly Phe Lys Asp Pro Val Tyr Arg Ala Arg Arg Lys Gln Phe
145                 150                 155                 160

Ala Asp Ile Ala Tyr Asn Tyr Arg His Gly Gln Pro Ile Pro Arg Val
                165                 170                 175

Glu Tyr Thr Glu Glu Glu Lys Lys Thr Trp Gly Thr Val Phe Arg Thr
            180                 185                 190

Leu Lys Ser Leu Tyr Lys Thr His Ala Cys Tyr Glu His Asn His Ile
        195                 200                 205

Phe Pro Leu Leu Glu Lys Tyr Cys Gly Phe Arg Glu Asp Asn Ile Pro
    210                 215                 220

Gln Leu Glu Glu Val Ser Gln Phe Leu Gln Ser Cys Thr Gly Phe Arg
225                 230                 235                 240

Leu Arg Pro Val Ala Gly Leu Leu Ser Ser Arg Asp Phe Leu Gly Gly
                245                 250                 255

Leu Ala Phe Arg Val Phe His Cys Thr Gln Tyr Ile Arg His Gly Ser
            260                 265                 270

Lys Pro Met Tyr Thr Pro Glu Pro Asp Ile Cys His Glu Leu Leu Gly
        275                 280                 285

His Val Pro Leu Phe Ser Asp Arg Ser Phe Ala Gln Phe Ser Gln Glu
    290                 295                 300

Ile Gly Leu Ala Ser Leu Gly Ala Pro Asp Glu Tyr Ile Glu Lys Leu
305                 310                 315                 320

Ala Thr Ile Tyr Trp Phe Thr Val Glu Phe Gly Leu Cys Lys Gln Gly

-continued

```
                325                 330                 335
Asp Ser Ile Lys Ala Tyr Gly Ala Gly Leu Leu Ser Ser Phe Gly Glu
            340                 345                 350

Leu Gln Tyr Cys Leu Ser Asp Lys Pro Lys Leu Leu Pro Leu Glu Leu
        355                 360                 365

Glu Lys Thr Ala Val Gln Glu Tyr Thr Ile Thr Glu Phe Gln Pro Leu
370                 375                 380

Tyr Tyr Val Ala Glu Ser Phe Asn Asp Ala Lys Glu Lys Val Arg Asn
385                 390                 395                 400

Phe Ala Ala Thr Ile Pro Arg Pro Phe Ser Val His Tyr Asp Pro Tyr
            405                 410                 415

Thr Gln Arg Ile Glu Val Leu Asp Asn Thr Gln Gln Leu Lys Ile Leu
        420                 425                 430

Ala Asp Ser Ile Ser Ser Glu Val Glu Ile Leu Cys Ser Ala Leu Gln
            435                 440                 445

Lys Leu Lys
    450

<210> SEQ ID NO 17
<211> LENGTH: 446
<212> TYPE: PRT
<213> ORGANISM: Gallus gallus

<400> SEQUENCE: 17

Met Asp Ala Gln His Cys Lys Met Asn Gly Asp Ser Phe Gln Glu Ser
1               5                   10                  15

Thr Tyr Thr Glu Glu Pro Ser Asn Lys Asn Gly Val Ile Ser Leu Ile
            20                  25                  30

Phe Ser Leu Lys Glu Glu Val Gly Ala Leu Ala Lys Val Leu Arg Thr
        35                  40                  45

Phe Glu Glu Lys Gly Ile Asn Leu Thr His Ile Glu Ser Arg Pro Ser
    50                  55                  60

Arg Leu Asn Lys Asp Glu Tyr Glu Phe Phe Ile Asn Leu Glu Gly Lys
65                  70                  75                  80

Asn Val Pro Ala Leu Asp Lys Ile Ile Lys Ser Leu Arg Asn Asp Ile
                85                  90                  95

Gly Val Thr Val His Glu Leu Ser Arg Thr Lys Lys Lys Asp Thr Val
            100                 105                 110

Pro Trp Phe Pro Arg Ser Ile Gln Glu Leu Asp Arg Phe Ala Asn Gln
        115                 120                 125

Ile Leu Ser Tyr Gly Ala Glu Leu Asp Ala Asp His Pro Gly Phe Lys
    130                 135                 140

Asp Pro Val Tyr Arg Ala Arg Arg Lys Glu Phe Ala Asp Ile Ala Tyr
145                 150                 155                 160

Asn Tyr Arg His Gly Gln Pro Ile Pro Arg Val Thr Tyr Thr Glu Glu
                165                 170                 175

Glu Lys Lys Thr Trp Gly Thr Val Phe Arg Glu Leu Lys Asn Leu Tyr
            180                 185                 190

Pro Thr His Ala Cys Tyr Glu His Asn His Val Phe Pro Leu Leu Glu
        195                 200                 205

Lys Tyr Cys Gly Tyr Arg Glu Asp Asn Ile Pro Gln Leu Glu Asp Val
    210                 215                 220

Ser Lys Phe Leu Gln Thr Cys Thr Gly Phe Arg Leu Arg Pro Val Ala
225                 230                 235                 240
```

```
Gly Leu Leu Ser Ser Arg Asp Phe Leu Ala Gly Leu Ala Phe Arg Val
                245                 250                 255

Phe His Ser Thr Gln Tyr Ile Arg His Ala Ser Lys Pro Met Tyr Thr
                260                 265                 270

Pro Glu Pro Asp Ile Cys His Glu Leu Leu Gly His Val Pro Leu Phe
                275                 280                 285

Ala Asp Pro Ser Phe Ala Gln Phe Ser Gln Glu Ile Gly Leu Ala Ser
    290                 295                 300

Leu Gly Ala Pro Asp Asp Phe Ile Glu Lys Leu Ala Thr Val Tyr Trp
305                 310                 315                 320

Phe Thr Val Glu Phe Gly Leu Cys Lys Glu Gly Asp Ser Leu Lys Ala
                325                 330                 335

Tyr Gly Ala Gly Leu Leu Ser Ser Phe Gly Glu Leu Gln Tyr Cys Leu
                340                 345                 350

Ser Gly Lys Pro Glu Ile Arg Pro Leu Val Leu Glu Asn Thr Ser Val
            355                 360                 365

Gln Lys Tyr Ser Val Thr Glu Phe Gln Pro Thr Tyr Phe Val Ala Glu
    370                 375                 380

Ser Phe Asn Asp Ala Lys Glu Lys Leu Arg Lys Phe Ala Gln Thr Ile
385                 390                 395                 400

Pro Arg Pro Phe Ser Val Arg Tyr Asn Pro Tyr Thr Gln Arg Ile Glu
                405                 410                 415

Val Leu Asp Asn Ala Lys Gln Leu Lys Asn Leu Ala Asp Thr Ile Asn
            420                 425                 430

Ser Glu Met Gly Ile Leu Cys Asn Ala Leu Gln Lys Ile Lys
            435                 440                 445
```

UNITED STATES PATENT AND TRADEMARK OFFICE
CERTIFICATE OF CORRECTION

PATENT NO. : 10,023,889 B2
APPLICATION NO. : 15/310040
DATED : July 17, 2018
INVENTOR(S) : Yan et al.

Page 1 of 1

It is certified that error appears in the above-identified patent and that said Letters Patent is hereby corrected as shown below:

In the Claims

Column 64, Line 50: '(ii)' should read --(iii)--

Column 64, Line 50: 'P. puticia' should read --P. putida--

Column 65, Line 4: 'pterin-4a-carbinolamine' should read --pterin-4α -carbinolamine--

Signed and Sealed this
Eleventh Day of December, 2018

Andrei Iancu
*Director of the United States Patent and Trademark Office*